US008221981B2

(12) United States Patent
Tcherepanova et al.

(10) Patent No.: US 8,221,981 B2
(45) Date of Patent: Jul. 17, 2012

(54) PRIMERS AND PROBES FOR THE AMPLIFICATION AND DETECTION OF HIV GAG, REV AND NEF POLYNUCLEOTIDES

(75) Inventors: Irina Tcherepanova, Rougemont, NC (US); Aijing Starr, Durham, NC (US); Brad Lackford, Durham, NC (US)

(73) Assignee: Argos Therapeutics, Inc., Durham, NC (US)

( * ) Notice: Subject to any disclaimer, the term of this patent is extended or adjusted under 35 U.S.C. 154(b) by 86 days.

(21) Appl. No.: 12/452,580

(22) PCT Filed: Jul. 30, 2008

(86) PCT No.: PCT/US2008/009185
§ 371 (c)(1),
(2), (4) Date: Jan. 8, 2010

(87) PCT Pub. No.: WO2009/017743
PCT Pub. Date: Feb. 5, 2009

(65) Prior Publication Data
US 2010/0136631 A1 Jun. 3, 2010

Related U.S. Application Data

(60) Provisional application No. 60/962,510, filed on Jul. 30, 2007.

(51) Int. Cl.
*C07H 21/04* (2006.01)
*C12Q 1/68* (2006.01)
*C12P 19/34* (2006.01)

(52) U.S. Cl. ............ 435/6.12; 435/91.2; 536/22.1; 536/24.33

(58) Field of Classification Search ............ 435/6.12, 435/91.2; 536/22.1, 24.33
See application file for complete search history.

(56) References Cited

U.S. PATENT DOCUMENTS
5,908,743 A 6/1999 Christopherson et al.
(Continued)

FOREIGN PATENT DOCUMENTS
WO WO 2006/031870 3/2006

OTHER PUBLICATIONS

Christopherson et al., "PCR-Based Assay to Quantify Human Immunodeficiency Virus Type 1 DNA in Peripheral Blood Mononuclear Cells" *Journal of Clinical Microbiology* (Feb. 2000) pp. 630-634.

(Continued)

*Primary Examiner* — Kenneth R. Horlick
*Assistant Examiner* — Joyce Tung
(74) *Attorney, Agent, or Firm* — Elaine T. Sale

(57) ABSTRACT

The invention relates to improved methods and compositions for the nucleic acid amplification of one or multiple variants (strains) of Human Immunodeficiency Virus (HIV) present in a sample, and preferably in a sample from a pathogen infected individual. In particular, novel primers, methods and kits for the amplification of one or more species of HIV Rev, Gag and Nef nucleic acids are provided. The amplified HIV nucleic acid can be used to identify and/or quantitate HIV variants present in a sample. Nucleic acids produced by the methods of the invention or the proteins encoded thereby can also be used directly as vaccines or to transfect/load antigen presenting cells. The loaded antigen presenting cells can be used as a vaccine for the treatment or prevention of HIV infection.

12 Claims, 17 Drawing Sheets

U.S. PATENT DOCUMENTS

| | | | |
|---|---|---|---|
| 6,090,392 | A | 7/2000 | Berman |
| 6,194,142 | B1 | 2/2001 | Moncany et al. |
| 6,232,455 | B1 | 5/2001 | Kroeger et al. |
| 6,531,588 | B1 | 3/2003 | Johnston-Dow et al. |
| 2003/0148280 | A1 | 8/2003 | Harris et al. |
| 2004/0081962 | A1 | 4/2004 | Chen et al. |
| 2007/0054311 | A1 | 3/2007 | Kamberov et al. |
| 2007/0248578 | A1 | 10/2007 | Tcherepanova et al. |
| 2008/0311155 | A1 | 12/2008 | Nicolette et al. |

OTHER PUBLICATIONS

Christopherson et al., "The effects of internal primer-template mismatches on RT-PCR: HIV-1 model studies" *Nucleic Acids Research* vol. 25, No. 3 (1997) pp. 654-658.

Abravaya et al., "Performance of a Multiplex Qualitative PCR LCx Assay for Detection of Human Immunodeficiency Virus Type 1 (HIV-1) Group M Subtypes, Group O, and HIV-2" *Journal of Clinical Microbiology* (Feb. 2000) pp. 716-723.

Michael et al., "Development of Calibrated Viral Load Standards for Group M Subtypes of Human Immunodeficiency Virus Type 1 and Performance of an Improved Amplicor HIV-1 Monitor Test with Isolates of Diverse Subtypes" *Journal of Clinical Microbiology*, (Aug. 1999) pp. 2557-2563.

Weissman et al., "HIV Gag mRNA Transfection of Dendritic Cells (DC) Delivers Encoded Antigen to MHC Class I and II Molecules, Causes DC Maturation, and Induces a Potent Human In Vitro Primary Immune Response" *Journal of Immunology* vol. 165 (2000) pp. 4710-4717.

Innis et al., "Optimaztion of PCRs" *PCR Protocols A Guide to Methods and Applications* (1990) pp. 3-12.

Compton et al., "Degenerate Primers for DNA Amplification" *PCR Protocols A Guide to Methods and Applications* (1990) pp. 39-45.

Candotti et al., "Multiplex real-time quantitative RT-PCR assay for hepatitis B virus, hepatitis C virus, and human immunodeficiency virus type I" *Journal of Virological Methods* vol. 118 (2004) pp. 39-47.

Berman et al., "Genetic and Immunologic Characterization of Viruses Infecting MN-RGPI20 Vaccinated Volunteers" *International Conference on AIDS* supplement 3, No. 10, Jul. 7, 1996, p. 10.

Kikuchi et al., "Dendritic cells genetically modified to express CD40 ligand and pulsed with antigen can initiate antigen-specific humoral immunity independent of CD4$^+$ T cells" *Nature Medicine* vol. 6, No. 10, pp. 1154-1159. Oct. 2000.

Machuca et al., "Human Immunodeficiency virus Type 2 Infection in Spain" *Intervirology* vol. 42, pp. 37-42 (1999).

Kellogg et al., "Detection of Human Immunodeficiency Virus" *PCR Protocols: A Guide to Methods and Applications* (1990) pp. 337-346.

```
QUERY                          GCTCTATTAGATACAGGAGCAGA
    REVERSE COMPLEMENT         ───────────────────────
                               ───────────────────────  GAG R1884
                               ───────────────────────  GAG R1883
                               ───────────────────────  GAG R1881
A1.KE.00.KNH1211               --C--------------------
A1.KE.99.KSM4021               ------C----------------
A.SN.01.DDJ369                 --G--------------------
B.US.88.WR27                   ---T-------------------  GAG R1881(3,4).1
B.US.97.1001                   -----G-----------------  GAG R1881(3,4).2
B.US.98.98USHVTN1925c1         ---------------------G--
C.AR.01.ARG4006                -----C-----C-----------  GAG R1884.3
C.BR.04.04BR021                -----T-----C-----------
```

FIG. 8

HAIRPIN: ΔG = -3.3 kcal/mol, LOOP = 16 nt, Tm = 52°

HAIRPIN: ΔG = -0.8 kcal/mol, LOOP = 9 nt, Tm = 40°

HAIRPIN: ΔG = -0.8 kcal/mol, LOOP = 9 nt, Tm = 40°

IVT Yield for 2.5 µg of cDNA
  G/G: 345 µg = 138 Fold
  G/A: 308 µg = 123 Fold
  G/C: 324 µg = 130 Fold
  G/T: 296 µg = 118 Fold

| Sample Number | Sample Acquired | Date of Plasma Draw | Viral Load Copies/ml | Volume Of Plasma Used | Clade | Copy/μl vRNA | Copy/μl RT RXN |
|---|---|---|---|---|---|---|---|
| 1 | North America | nd | 244,000 | 1 | B | 4880 | 610 |
| 2 | North America | 23-Mar-04 | 146,148 | 1 | B | 2922.96 | 365 |
| 3 | North America | 25-Mar-04 | 3,221,835 | 1 | B | 64436.7 | 8055 |
| 4 | North America | 6-May-03 | 22,155 | 3 | B | 1329.3 | 166 |
| 5 | North America | 3-Nov-04 | 38,663 | 3 | B | 2319.78 | 290 |
| 6 | North America | nd | 53,725 | 3 | B | 3223.5 | 403 |
| 7 | North America | 15-Oct-03 | 28,840 | 3 | B | 1730.4 | 432 |
| 8 | North America | 9-Apr-01 | 154,882 | 3 | AG | 9292.92 | 1162 |
| 9 | North America | 25-May-01 | 33,884 | 3 | B | 2033.04 | 508 |
| 10 | North America | 8-Apr-03 | 7,413 | 3 | B | 444.78 | 111 |
| 11 | North America | unknown | 1,138,560 | 3 | B | 68313.6 | 8539 |
| 12 | North America | 4-Oct-04 | 16,596 | 3 | B | 995.76 | 124 |
| 13 | North America | 10-Mar-03 | 45,709 | 3 | B | 2742.54 | 343 |
| 14 | North America | 12-Jan-04 | 38,905 | 3 | B | 2334.3 | 292 |
| 15 | Netherlands | 21-Dec-04 | 50,070 | 1 | nd | 1001.4 | 125 |
| 16 | Netherlands | 3-Jan-05 | 72,978 | 1 | nd | 1459.56 | 182 |
| 17 | North America | 9-Sept-04 | 50,119 | 3 | B | 3007.14 | 376 |
| 18 | North America | 28-Sept-04 | 50,119 | 3 | B | 3007.14 | 376 |
| 19 | North America | 25-Apr-03 | 134,000 | 3 | B | 8040 | 1005 |
| 20 | North America | 3-Nov-04 | 18,197 | 3 | B | 1091.82 | 273 |
| 21 | Netherlands | 10-Jan-05 | 72865 | 1 | nd | 1457.3 | 182 |
| 22 | North America | 3-Nov-04 | 1,479,108 | 3 | nd | 88746.48 | 11093 |
| 23 | Netherlands | 20-Dec-04 | 48,627 | 1 | nd | 972.54 | 122 |
| 24 | North America | 23-Mar-05 | 95,637 | 2 | B | 3825.48 | 478 |
| 25 | North America | 26-Mar-03 | 53,334 | 2 | B | 2133.36 | 267 |
| 26 | North America | 18-Mar-04 | 131826 | 3 | B | 7909.56 | 988.7 |
| 27 | North America | 5-Oct-04 | 158,489 | 3 | B | 9509.34 | 1189 |
| 28 | North America | 5-Feb-04 | 117,490 | 3 | B | 7049.4 | 881 |
| 29 | North America | 29-Apr-03 | 513,000 | 1.5 | nd | 15390 | 1924 |
| 30 | North America | 15-Sep-03 | 14,791 | 3 | B | 887.46 | 111 |

SEQUENCE LISTING

```
<160> NUMBER OF SEQ ID NOS: 77

<210> SEQ ID NO 1
<211> LENGTH: 9184
<212> TYPE: DNA
<213> ORGANISM: Human immunodeficiency virus

<400> SEQUENCE: 1
gaagcactca aggcaagctt tattgaggct taagcagtgg gttccctagt tagccagaga      60
gctcccaggc tcagatctgg tctaaccaga gagacccagt acaggcaaaa agcagctgct     120
tatatgcagg atctgagggc tcgccactcc ccagtcccgc ccaggccacg cctccctgga     180
aagtccccag cggaaagtcc cttgtagcaa gctcgatgtc agcagttctt gaagtactcc     240
ggatgcagct ctcgggccac gtgatgaaat gctaggcggc tgtcaaacct ccactctaac     300
acttctctct ccgggtcatc catcccatgc aggctcacag ggtgtaacaa gctggtgttc     360 tctccttat tggcctcttc tatcttatct ggctcaactg gtactagctt gtagcaccat      420
ccaaaggtca gtggatatct gacccctggc cctggtgtgt agttctgcta atcagggaag     480
tagccttgtg tgtggtagat ccacagatca aggatatctt gtcttctttg ggagtgaatt     540
agcccttcca gtccccctt ttcttttaaa aagtggctaa gatctacagc tgccttgtaa     600
gtcattggtc ttaaaggtac ctgaggtgtg actggaaaac ccacctcctc ctcctcttgt     660
gcttctagcc aggcacaagc agcattggta gctgctgtat tgctacttgt gattgctcca     720
```

```
tgttttttcca ggtctcgaga tgctgctccc accctatctg ctgctggctc agctcgtctc   780
attctttccc ttacagtagg ccatccaatc acactacttt tgaccactt gccacccatc    840
ttatagcaaa atcctttcca agccctgtct tattcttcta ggtatgtggc aatagctct    900
acaagctcct tgtactactt ctataaccct atctgtcccc tcagctactg ctatggctgt    960
ggcattgagc aagctaacag cactattctt tagttcctga ctccaatact gtaggagatt   1020
ccaccaatat ttgagggctt cccacccccct gcgtcccaga agttccacaa tcctcgttac  1080
aatcaagagt aagtctctca agcggtggta gctgaagagg cacaggctcc gcagatcgtc   1140
ccagataagt gccaaggatc cgttcactaa tcgaatggat ctgtctctgt ctctctctcc   1200
accttcttct tctattcctt cgggcctgtc gggtcccctc ggggttggga ggtgggtctg   1260
aaacgataat ggtgaatatc cctgcctaac tctattcact atagaaagta cagcaaaaac   1320
tattcttaaa cctaccaagc ctcctactat cattatgaat aattttatat accacagcca   1380
atttgttatg ttaaaccaat tccacaaact tgcccattta tctaattcca ataattcttg   1440
ttcattcttt tcttgctggt tttgcgattc ttcaattaag gagtgtatta agcttgtgta   1500
attgttaatt tctctgtccc actccatcca ggtcgtgtga ttccaaatct gttccagaga   1560
tttattactc caactagcat tccaaggcac agcagtggtg caaatgagtt ttccagagca   1620
accccaaatc cccaggagct gttgatcctt taggtatctt tccacagcca ggattcttgc   1680
ctggagctgc ttgatgcccc agactgtgag ttgcaacaga tgctgttgcg cctcaatagc   1740
cctcagcaaa ttgttctgct gctgcactat accagacaat aattgtctgg cctgtaccgt   1800
cagcgtcatt gaggctgcgc ccatagtgct tcctgctgct cccaagaacc caaggaacaa   1860
agctcctatt cccactgctc ttttttctct ctgcaccact cttctctttg ccttggtggg   1920
tgctactcct aatggttcaa tttttactac tttatattta tataattcac ttctccaatt   1980
gtccctcata tctcctcctc caggtctgaa gatctcggac tcattgttgc tattaccacc   2040
atctcttgtt aatagcagcc ctgtaatatt tgatgaacat ctaatttgtc cactgatggg   2100
aggggcatac attgcttttc ctactttctg ccacatgttt ataatttgtt ttattctgca   2160
tgggagggtg attgtgtcac ttccttcagt gttatttgac ccttcagtac tccaagtact   2220
attaaaccaa gtactattaa acagttgtgt tgaattacag tagaaaaatt cccctccaca   2280
attaaaactg tgcgttacaa tttctgggtc ccctcctgag gattgcttaa agattattgt   2340
tttattattt ccaaattgtt ctcttaattt gctagctatc tgttttaaag tgttattcca   2400
ttttgctcta ctaatgttac aatgtgcttg tctcatattt cctattttc ctattgtaac    2460
aaatgctctc cctggtcctc tctggatacg gattctttt cttgtattgt tgttgggtct    2520
tgtacaatta atttctacag atgtgttcag ctgtactatt atggttttag cattgtccgt   2580
gaaattgaca gatctaatta ctacctcttc ttctgctaga ctgccattta acagcagttg   2640
agttgatact actggcctaa ttccatgtgt acattgtact gtgctgacat tgtacatgg    2700
tcctgttcca ttgaacgtct tattattaca ttttagaatc gcaaaccag ccggggcaca    2760
ataatgtatg ggaattggct caaaggatac ctttggacag gcctgtgtaa tgactgaggt   2820
gttacaactt gtcaacttat agctggtagt atcattatct attggtatta tatcaagttt   2880
ataaaaaaat gcatattctt tctgcacctt acctcttatg cttgtgctga tattgaaaga   2940
gcagtttttt atctctcctt tctccattat cattctcccg ctactactat tggtattagt   3000
atcattcttc aaatcagtgc actttaaact aacacagagt ggggttaatt ttacacatgg   3060
ctttaggctt tgatcccata aactgattat atcctcatgc atctgttcta ccatgtcatt   3120
```

```
tttccacatg ttaaaatttt ctgtcacatt taccaatact acttcttgtg ggttggggtc    3180
tgtgggtaca caggcatgtg tggcccaaac attatgtacc tctgtatcat atgctttagc    3240
atctgatgca caaaatagag tggtggttgc ttccttccac acaggtaccc cataatagac    3300
tgtgacccac aattttctg tagcactaca gatcatcaac atcccaagga gcatggtgcc     3360
ccatctccac ccccatctcc acaagtgctg atatttctcc ttcactctca ttgccactgt    3420
cttctgctct ttctattagt ctatcaatta acctgtctat ttttctttgt cttaatattt    3480
tcctatattc tatgattact atggaccaca caactattgc tattattatt gctactacta    3540
atgctactat tgctactatt ggtataggtt gcattacatg tactacttac tgctttgata    3600
gagaagcttg atgagtctga ctgttctgat gagctcttcg tcgctgtctc cgcttcttcc    3660
tgccatagga gatgcctaag cttttgtta tgaaacaaac ttggcaatga agcaacact     3720 ttttacaata gcaattggta caagcagttt taggctgact tcctggatgc ttccagggct    3780
ctagtctagg atctactggc tccatttctt gctctcctct gtcgagtaac gcctattctg    3840
ctatgtcgac acccaattct gaaaatggat aaacagcagt tgttgcagaa ttcttattat    3900
ggcttccact cctgcccaag tatccccata agtttcatag atatgttgcc ctaagccatg    3960
gagccaaatc ctaggaaaat gtctaacagc ttcattctta agctcctcta aaagctctag    4020
tgtccattca ttgtgtggct ccctctgtgg cccttggtct tctggggctt gttccatcta    4080
tcctctgtca gtttcgtaac actaggcaaa ggtggcttta tctttttgg tgttattaat     4140 gctgctagtg ccaagtattg tagagatcct accttgttat gtcctgcttg atattcacac    4200
ctagggctaa ctatgtgtcc taataaggcc tttcttatag cagagtctga aaaacagtca    4260
aagtaataca gatgaattag ttggtctgct agttcagggt ctacttgtgt gctatatctc    4320
tttttcctcc attctatgga gactccctga cccaaatgcc agtctctttc tcctgtatgc    4380 agacccaat atgttgttat taccaatcta gcatccccta gtgggatgtg tacttctgaa     4440
cttattcttg gatgagggct ttcatagtga tgtctataaa accatcccct agctttccct    4500
gaaacataca tatggtgttt tactaaactt ttccatgttc taatcctcat cctgtctact    4560
tgccacacaa tcatcacctg ccatctgttt tccataatcc ctaatgatct ttgcttttct    4620
tcttggcact acttttatgt cactattatc ttgtattact actgccccct caccttccca    4680
gaggagcttt gctggtcctt tccaaagtgg atttctgctg tccctgtaat aaacccgaaa    4740
attttgaatt tttgtaattt gttttttgtaa ttctttagtt tgtatgtctg ttgctattat    4800
gtctactatt ctttcccctg cactgtaccc cccaatcccc ccttttcttt taaaattgtg    4860
gatgaatact gccatttgta ctgctgtctt aagatgttca gcctgatctc ttacctgtcc    4920
tataattttc tttaattctt tattcataga ttctactact ccttgacttt ggggattgta    4980
gggaattcca aattcctgct tgattcccgc ccaccaacag gcggccctaa ccgtagcacc    5040
ggtgaaattg ctgccattgt cagtatgtat tgttttact ggccatcttc ctgctaattt      5100
taaaagaaaa tatgctgttt cctgccctgt ttctgctgga ataacttctg cttctatata    5160
tccactggct acatgaactg ctaccaggat aacttttcct tctaaatgtg tacaatctag    5220
ttgccatatt cctggactac agtctacttg tccatgcatg gcttctcctt ttagctgaca    5280
tttatcacag ctggctacta tttcttttgc tactacaggt ggcaggttaa aatcactagc    5340
cattgctctc caattactgt gatatttctc atgttcatct tgggccttat ctattccatc    5400
taaaaatagt actttcctga ttccagcact gactaattta tctacttgtt catttcctcc    5460
aattcctttg tgtgctggta cccatgccag atagaccttt tccttttta ttaactgctc     5520
```

```
tattatttga ttgactaact ctgattcact ttgatctggt tgtgcttgaa tgattcctaa    5580
tgcatattgt gagtctgtta ctatgtttac ttctaatccc gaatcctgca aagctagata    5640
aattgcttgt aactcagtct tctgatttgt tgtgtcagtt agggtgacaa cttttttgtct   5700
tcctctatta gtaacatatc ctgcttttcc taatttagtc tccctgttag ctgcccatc     5760
tacatagaag gtttctgctc ctactatggg ttctttctct aactggtacc ataatttcac    5820
taagggaggg gtattaacaa actcccactc aggaatccag gtggcttgcc aatactctgt    5880
ccaccatgtt tcccatgttt cctttgtat gggcagttta aatttaggag tctttcccca     5940
tattactatg ctttctgtgg ttattttttg cactgcctct gttaattgtt ttacatcatt    6000
agtgtgggca cccctcattc ttgcatattt tcctgttttc agatttttaa atggctcttg    6060
ataaatttga tatgtccatt ggccttgccc ctgcttctgt atttctgcta ttaagtcttt    6120
tgatgggtca taatacactc catgtactgg ttcttttaga atctctctgt tttctgccag    6180
ttctagctct gcttcttctg ttagtggtat tacttctgtt agtgctttgg ttcctctaag    6240
gagtttacat aattgcctta ctttaatccc tgggtaaatc tgacttgccc aattcaattt    6300
ccccactaac ttctgtatgt cattgacagt ccagctgtct ttttctggca gcactatagg    6360
ctgtactgtc catttatcag gatggagttc ataacccatc caaggaatg gaggttcttt     6420
ctgatgtttt ttgtctggtg tggtaagtcc ccacctcaac agatgttgtc tcagctcctc    6480
tattttgtt ctatgctgcc ctatttctaa gtcagatcct acatacaaat catccatgta     6540
ttgatagata actatgtctg gattttgttt tctaaaaggc tctaagattt ttgtcatgct    6600
actttggaat attgctggtg atcctttcca tccctgtgga agcacattgt actgatatct    6660
aatccctggt gtctcattgt ttatactagg tatggtaaat gcagtatact tcctgaagtc    6720
ttcatctaag ggaactgaaa aatatgcatc acccacatcc agtactgtta ctgatttttt    6780
cttttttaac cctgcgggat gtggtattcc taattgaact tcccagaagt cttgagttct    6840
cttattaagt tctctgaaat ctactaattt tctccattta gtactgtctt ttttctttat    6900
ggcaaatact ggagtattgt atggattttc aggcccaatt tttgaaattt tcccttcctt    6960
ttccatctct gtacaaattt ctactaatgc ttttattttt tcttctgtca atggccattg    7020
tttaactttt gggccatcca ttcctggctt taattttact ggtacagtct caatagggct    7080
aatgggaaaa tttaaagtgc aaccaatctg agtcaacaga tttcttccaa ttatgttgac    7140
aggtgtaggt cctactaata ctgtacctat agctttatgt ccacagattt ctatgagtat    7200
ctgatcatac tgtcttactt tgataaaacc tccaattccc cctatcattt ttggtttcca    7260
tcttcctggc aaactcattt cttctaatac tgtatcatct gctcctgtat ctaatagagc    7320
ttccttagt tgccccccta tctttattgt gacgaggggt cgttgccaaa gagtgacctg      7380
agggaagtta aaggatacag ttccttgtct atcggctcct gcttctgagg gggagttgtt    7440
gtctctaccc cagacctgaa gctctcttct ggtggggctg ttggctctgg tctgctctga    7500
agaaaattcc ctggccttcc cttgtaggaa ggccagatct tccctaaaaa attagcctgt    7560
ctctcagtac aatctttcat ttggtgtcct tcctttccac atttccaaca gccctttttc    7620
ctaggggccc tgcaatttct ggctgtgtgc ccttctttgc cacaattgaa acacttaaca    7680
atctttcttt ggttcctaaa attgcctctc tgcatcatta tggtagctga atttgttact    7740
tggctcattg cttcagccaa aactcttgcc ttatggccgg gtcctcctac tccctgacat    7800
gctgtcatca tttcttctag tgtagccgct ggtcccaatg cttttaaaat agtcttacaa    7860
tctgggttcg catttttggac caacaaggtt tctgtcatcc aatttttttac ctcctgtgaa   7920
```

```
gcttgctcgg ctcttagagt tttatagaac cggtctacat agtctctaaa gggttccttt      7980
ggtccttgtc ttatgtccag aatgctggta gggctataca ttcttactat tttatttaat      8040
cccaggatta tccatctttt ataaatttct cctactggga taggtggatt atttgtcatc      8100
catcctattt gttcctgaag ggtactagta gttcctgcta tgtcacttcc ccttggttct      8160
ctcatctggc ctggtgcaat aggccctgca tgcactggat gcactctatc ccattctgca      8220
gcttcctcat tgatggtctc ttttaacatt tgcatgctg cttgatgtcc ccccactgtg       8280
tttagcatgg tgtttaaatc ttgtggggtg gctccttctg ataatgctga aaacatgggt      8340
atcacttctg ggctgaaagc cttctcttct actacttttta cccatgcatt taaagttcta     8400
ggtgatatgg cctgatgtac catttgcccc tggatgttct gcactatagg gtaattttgg      8460
ctgacctgat tgctgtgtcc tgtgtcagct gctgcttgct gtgcttttttt cttacttttg     8520 ttttgctctt cctctatctt gtctaaagct tccttggtgt cttttatctc tatcctttga      8580
tgcacacaat agagggttgc tactgtatta tataatgatc taagttcttc tgatcctgtc      8640
tgaagggatg gttgtagctg tcccagtatt tgtctacagc cttctgatgt ttctaacagg      8700
ccaggattaa ctgcgaatcg ttctagctcc ctgcttgccc atactatatg tttttaattta    8760 tattttttct ttccccctgg ccttaaccga atttttttccc atcgatctaa ttctcccccg    8820
cttaatactg acgctctcgc acccatctct ctccttctag cctccgctag tcaaaatttt     8880
tggcgtactc accagtcgcc gcccctcgcc tcttgccgtg cgcgcttcag caagccgagt     8940
cctgcgtcga gagagctcct ctggtttccc tttcgctttc aggtccctgt tcgggcgcca     9000
ctgctagaga ttttccacac tgactaaaag ggtctgaggg atctctagtt accagagtca     9060
cacaacagac gggcacacac tacttgaagc actcaaggca agctttattg aggcttaagc     9120
agtgggttcc ctagttagcc agagagctcc caggctcaga tctggtctaa ccagagagac      9180
ccct                                                                   9184

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2
gggatttggg gttgctctgg                                                    20

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
gggatttggg gctgctctgg                                                    20

<210> SEQ ID NO 4
<211> LENGTH: 22
<212> TYPE: DNA
<213> ORGANISM: Artificial sequence
<220> FEATURE:
<223> OTHER INFORMATION: Synthetic primer

<400> SEQUENCE: 4
tgatagtagg aggcttggta gg                                                 22
```

```
<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
tgatagtagg aggctttagg                                               20

<210> SEQ ID NO 6
<211> LENGTH: 22
<212> TYPE: DNA
<213> ORGANISM: Artificial sequence
<220> FEATURE:
<223> OTHER INFORMATION: Synthetic primer

<400> SEQUENCE: 6
tgatagtagg aggcttggta gg                                            22

<210> SEQ ID NO 7
<211> LENGTH: 20
<212> TYPE: DNA
<213> ORGANISM: Artificial sequence
<220> FEATURE:
<223> OTHER INFORMATION: Synthetic primer

<400> SEQUENCE: 7
gttaggcagg gatattcacc                                               20

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
gttaggcagg gatactcacc                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic primer

<400> SEQUENCE: 9
ccctgtctta ttcttctagg                                               20

<210> SEQ ID NO 10
<211> LENGTH: 20
<212> TYPE: DNA
<213> ORGANISM: Artificial sequence
<220> FEATURE:
<223> OTHER INFORMATION: Synthetic primer

<400> SEQUENCE: 10
ccctgtctta ttcttacagg                                               20

<210> SEQ ID NO 11
<211> LENGTH: 20
<212> TYPE: DNA
<213> ORGANISM: Artificial sequence
<220> FEATURE:
<223> OTHER INFORMATION: Synthetic primer
```

<400> SEQUENCE: 11
ccctgtctta ttcttgtagg        20

<210> SEQ ID NO 12
<211> LENGTH: 43
<212> TYPE: DNA
<213> ORGANISM: Artificial sequence
<220> FEATURE:
<223> OTHER INFORMATION: Synthetic primer

<400> SEQUENCE: 12
taatacgact cactataggg agaccaccat ggacccacct ccc        43

<210> SEQ ID NO 13
<211> LENGTH: 43
<212> TYPE: DNA
<213> ORGANISM: Artificial sequence
<220> FEATURE:
<223> OTHER INFORMATION: Synthetic primer

<400> SEQUENCE: 13
taatacgact cactataggg agaccaccat ggacccgcct ccc        43

<210> SEQ ID NO 14
<211> LENGTH: 84
<212> TYPE: DNA
<213> ORGANISM: Artificial sequence
<220> FEATURE:
<223> OTHER INFORMATION: Synthetic primer

<400> SEQUENCE: 14
tttttttttt tttttttttt tttttttttt tttttttttt tttttttttt tttttttttt        60
ttttccctgt cttattcttc tagg        84

<210> SEQ ID NO 15
<211> LENGTH: 84
<212> TYPE: DNA
<213> ORGANISM: Artificial sequence
<220> FEATURE:
<223> OTHER INFORMATION: Synthetic primer

<400> SEQUENCE: 15
tttttttttt tttttttttt tttttttttt tttttttttt tttttttttt tttttttttt        60
ttttccctgt cttattctta cagg        84

<210> SEQ ID NO 16
<211> LENGTH: 84
<212> TYPE: DNA
<213> ORGANISM: Artificial sequence
<220> FEATURE:
<223> OTHER INFORMATION: Synthetic primer

<400> SEQUENCE: 16
tttttttttt tttttttttt tttttttttt tttttttttt tttttttttt tttttttttt        60
ttttccctgt cttattcttg tagg        84

<210> SEQ ID NO 17
<211> LENGTH: 48
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)

<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 17
nnnnntaata cgactcacta taggnagacc accatgtcag acccacct        48

<210> SEQ ID NO 18
<211> LENGTH: 48
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C, or T.

<400> SEQUENCE: 18
nnnnntaata cgactcacta taggnagacc accatgtcag acccgcct        48

<210> SEQ ID NO 19
<211> LENGTH: 48
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 19
nnnnntaata cgactcacta taggnagacc accatgtcag accctcct        48

<210> SEQ ID NO 20
<211> LENGTH: 48
<212> TYPE: DNA
<213> ORGANISM: Artificial sequence
<220> FEATURE:

```
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 20
nnnnntaata cgactcacta taggnagacc accatgtcag acccatac         48

<210> SEQ ID NO 21
<211> LENGTH: 48
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 21
nnnnntaata cgactcacta taggnagacc accatgtcag atccatac         48

<210> SEQ ID NO 22
<211> LENGTH: 48
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 22
nnnnntaata cgactcacta taggnagacc accatgtcag acccttac         48

<210> SEQ ID NO 23
```

```
<211> LENGTH: 48
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 23
nnnnntaata cgactcacta taggnagacc accatgtcag acccctac         48

<210> SEQ ID NO 24
<211> LENGTH: 52
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 24
nnnnntaata cgactcacta taggnagacc accatggacc cacctcccaa cc       52

<210> SEQ ID NO 25
<211> LENGTH: 52
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 25
```

```
nnnnntaata cgactcacta taggnagacc accatggacc cacctcccag cc        52
```

<210> SEQ ID NO 26
<211> LENGTH: 52
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 26

```
nnnnntaata cgactcacta taggnagacc accatggacc cacctcccag gt        52
```

<210> SEQ ID NO 27
<211> LENGTH: 52
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 27

```
nnnnntaata cgactcacta taggnagacc accatggacc cttaccccaa cc        52
```

<210> SEQ ID NO 28
<211> LENGTH: 52
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)

<223> OTHER INFORMATION: "n" is G, A, C or T.

<400> SEQUENCE: 28
nnnnntaata cgactcacta taggnagacc accatggacc cttaccccaa ac    52

<210> SEQ ID NO 29
<211> LENGTH: 52
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: "n" is G or absent.
<220> FEATURE:
<221> NAME/KEY: misc_feature
<222> LOCATION: (2)..(3)
<223> OTHER INFORMATION: "n" is A or absent.
<220> FEATURE:
<221> NAME/KEY: misc_feature
<222> LOCATION: (4)..(5)
<223> OTHER INFORMATION: "n" is T or absent.
<220> FEATURE:
<221> NAME/KEY: misc_feature
<222> LOCATION: (25)..(25)
<223> OTHER INFORMATION: "n" is G, A, C or T.

<400> SEQUENCE: 29
nnnnntaata cgactcacta taggnagacc accatggacc cttaccccaa gc    52

<210> SEQ ID NO 30
<211> LENGTH: 20
<212> TYPE: DNA
<213> ORGANISM: Artificial sequence
<220> FEATURE:
<223> OTHER INFORMATION: Synthetic primer

<400> SEQUENCE: 30
actctggtaa ctagagatcc    20

<210> SEQ ID NO 31
<211> LENGTH: 19
<212> TYPE: DNA
<213> ORGANISM: Artificial sequence
<220> FEATURE:
<223> OTHER INFORMATION: Synthetic primer

<400> SEQUENCE: 31
aattttgact agcggaggc    19

<210> SEQ ID NO 32
<211> LENGTH: 18
<212> TYPE: DNA
<213> ORGANISM: Artificial sequence
<220> FEATURE:
<223> OTHER INFORMATION: Synthetic primer

<400> SEQUENCE: 32
agatgggtgc gagagcgt    18

<210> SEQ ID NO 33
<211> LENGTH: 18
<212> TYPE: DNA
<213> ORGANISM: Artificial sequence
<220> FEATURE:
<223> OTHER INFORMATION: Synthetic primer

<400> SEQUENCE: 33
agatgggtgc gagaccgt                                             18

<210> SEQ ID NO 34
<211> LENGTH: 20
<212> TYPE: DNA
<213> ORGANISM: Artificial sequence
<220> FEATURE:
<223> OTHER INFORMATION: Synthetic primer

<400> SEQUENCE: 34
gctcctgtat ctaatagagc                                           20

<210> SEQ ID NO 35
<211> LENGTH: 20
<212> TYPE: DNA
<213> ORGANISM: Artificial sequence
<220> FEATURE:
<223> OTHER INFORMATION: Synthetic primer

<400> SEQUENCE: 35
gctcctgtat ctaataaagc                                           20

<210> SEQ ID NO 36
<211> LENGTH: 20
<212> TYPE: DNA
<213> ORGANISM: Artificial sequence
<220> FEATURE:
<223> OTHER INFORMATION: Synthetic primer

<400> SEQUENCE: 36
gctcctgtat ctaacagagc                                           20

<210> SEQ ID NO 37
<211> LENGTH: 20
<212> TYPE: DNA
<213> ORGANISM: Artificial sequence
<220> FEATURE:
<223> OTHER INFORMATION: Synthetic primer

<400> SEQUENCE: 37
tttggtttcc atcttcctgg                                           20

<210> SEQ ID NO 38
<211> LENGTH: 20
<212> TYPE: DNA
<213> ORGANISM: Artificial sequence
<220> FEATURE:
<223> OTHER INFORMATION: Synthetic primer

<400> SEQUENCE: 38
tttggtttcc atcttcctgc                                           20

<210> SEQ ID NO 39
<211> LENGTH: 20
<212> TYPE: DNA
<213> ORGANISM: Artificial sequence
<220> FEATURE:
<223> OTHER INFORMATION: Synthetic primer

<400> SEQUENCE: 39
tttcgtttcc atctccctgg                                           20

<210> SEQ ID NO 40
<211> LENGTH: 20
<212> TYPE: DNA
<213> ORGANISM: Artificial sequence
<220> FEATURE:

<223> OTHER INFORMATION: Synthetic primer

<400> SEQUENCE: 40
tttggtttcc atttccctgg                                               20

<210> SEQ ID NO 41
<211> LENGTH: 20
<212> TYPE: DNA
<213> ORGANISM: Artificial sequence
<220> FEATURE:
<223> OTHER INFORMATION: Synthetic primer

<400> SEQUENCE: 41
tttggtttcc attttcctgg                                               20

<210> SEQ ID NO 42
<211> LENGTH: 20
<212> TYPE: DNA
<213> ORGANISM: Artificial sequence
<220> FEATURE:
<223> OTHER INFORMATION: Synthetic primer

<400> SEQUENCE: 42
ctgctcctgt atctaataga                                               20

<210> SEQ ID NO 43
<211> LENGTH: 20
<212> TYPE: DNA
<213> ORGANISM: Artificial sequence
<220> FEATURE:
<223> OTHER INFORMATION: Synthetic primer

<400> SEQUENCE: 43
ctgctcctgt atctaataaa                                               20

<210> SEQ ID NO 44
<211> LENGTH: 20
<212> TYPE: DNA
<213> ORGANISM: Artificial sequence
<220> FEATURE:
<223> OTHER INFORMATION: Synthetic primer

<400> SEQUENCE: 44
ctgctcctgt atctaacaga                                               20

<210> SEQ ID NO 45
<211> LENGTH: 20
<212> TYPE: DNA
<213> ORGANISM: Artificial sequence
<220> FEATURE:
<223> OTHER INFORMATION: Synthetic primer

<400> SEQUENCE: 45
tctgctcctg tatctaatag                                               20

<210> SEQ ID NO 46
<211> LENGTH: 20
<212> TYPE: DNA
<213> ORGANISM: Artificial sequence
<220> FEATURE:
<223> OTHER INFORMATION: Synthetic primer

<400> SEQUENCE: 46
tctgctcctg tatctaataa                                               20

<210> SEQ ID NO 47

```
<211> LENGTH: 20
<212> TYPE: DNA
<213> ORGANISM: Artificial sequence
<220> FEATURE:
<223> OTHER INFORMATION: Synthetic primer

<400> SEQUENCE: 47
tctgctcctg tatctaacag                                               20

<210> SEQ ID NO 48
<211> LENGTH: 20
<212> TYPE: DNA
<213> ORGANISM: Artificial sequence
<220> FEATURE:
<223> OTHER INFORMATION: Synthetic primer

<400> SEQUENCE: 48
tctgctcctg tgtctaagag                                               20

<210> SEQ ID NO 49
<211> LENGTH: 19
<212> TYPE: DNA
<213> ORGANISM: Artificial sequence
<220> FEATURE:
<223> OTHER INFORMATION: Synthetic primer

<400> SEQUENCE: 49
tagctgaggg gacagatag                                                19

<210> SEQ ID NO 50
<211> LENGTH: 19
<212> TYPE: DNA
<213> ORGANISM: Artificial sequence
<220> FEATURE:
<223> OTHER INFORMATION: Synthetic primer

<400> SEQUENCE: 50
tagctgaggg aacagatag                                                19

<210> SEQ ID NO 51
<211> LENGTH: 23
<212> TYPE: DNA
<213> ORGANISM: Artificial sequence
<220> FEATURE:
<223> OTHER INFORMATION: Synthetic primer

<400> SEQUENCE: 51
atgggtggca agtggtcaaa aag                                           23

<210> SEQ ID NO 52
<211> LENGTH: 23
<212> TYPE: DNA
<213> ORGANISM: Artificial sequence
<220> FEATURE:
<223> OTHER INFORMATION: Synthetic primer

<400> SEQUENCE: 52
atgggtggca agtggtcaaa acg                                           23

<210> SEQ ID NO 53
<211> LENGTH: 23
<212> TYPE: DNA
<213> ORGANISM: Artificial sequence
<220> FEATURE:
<223> OTHER INFORMATION: Synthetic primer

<400> SEQUENCE: 53
```

-continued

```
atgggtggca aatggtcaaa aag                                              23

<210> SEQ ID NO 54
<211> LENGTH: 23
<212> TYPE: DNA
<213> ORGANISM: Artificial sequence
<220> FEATURE:
<223> OTHER INFORMATION: Synthetic primer

<400> SEQUENCE: 54
atgggtggca agtggtcaaa agg                                              23

<210> SEQ ID NO 55
<211> LENGTH: 18
<212> TYPE: DNA
<213> ORGANISM: Artificial sequence
<220> FEATURE:
<223> OTHER INFORMATION: Synthetic primer

<400> SEQUENCE: 55
ccagtacagg caaaaagc                                                    18

<210> SEQ ID NO 56
<211> LENGTH: 17
<212> TYPE: DNA
<213> ORGANISM: Artificial sequence
<220> FEATURE:
<223> OTHER INFORMATION: Synthetic primer

<400> SEQUENCE: 56
cagtacaggc gaaaagc                                                     17

<210> SEQ ID NO 57
<211> LENGTH: 17
<212> TYPE: DNA
<213> ORGANISM: Artificial sequence
<220> FEATURE:
<223> OTHER INFORMATION: Synthetic primer

<400> SEQUENCE: 57
cagtacaggc aagaagc                                                     17

<210> SEQ ID NO 58
<211> LENGTH: 19
<212> TYPE: DNA
<213> ORGANISM: Artificial sequence
<220> FEATURE:
<223> OTHER INFORMATION: Synthetic primer

<400> SEQUENCE: 58
tagctggctg gacagatag                                                   19

<210> SEQ ID NO 59
<211> LENGTH: 44
<212> TYPE: DNA
<213> ORGANISM: Artificial sequence
<220> FEATURE:
<223> OTHER INFORMATION: Synthetic primer

<400> SEQUENCE: 59
taatacgact cactataggg agaccaccat gggtgcgaga gcgt                       44

<210> SEQ ID NO 60
<211> LENGTH: 44
<212> TYPE: DNA
<213> ORGANISM: Artificial sequence
<220> FEATURE:
```

<223> OTHER INFORMATION: Synthetic primer

<400> SEQUENCE: 60
taatacgact cactataggg agaccaccat gggtgcgaga ccgt        44

<210> SEQ ID NO 61
<211> LENGTH: 84
<212> TYPE: DNA
<213> ORGANISM: Artificial sequence
<220> FEATURE:
<223> OTHER INFORMATION: Synthetic primer

<400> SEQUENCE: 61
tttttttttt tttttttttt tttttttttt tttttttttt tttttttttt tttttttttt        60
ttttgctcct gtatctaata gagc        84

<210> SEQ ID NO 62
<211> LENGTH: 84
<212> TYPE: DNA
<213> ORGANISM: Artificial sequence
<220> FEATURE:
<223> OTHER INFORMATION: Synthetic primer

<400> SEQUENCE: 62
tttttttttt tttttttttt tttttttttt tttttttttt tttttttttt tttttttttt        60
ttttgctcct gtatctaata aagc        84

<210> SEQ ID NO 63
<211> LENGTH: 84
<212> TYPE: DNA
<213> ORGANISM: Artificial sequence
<220> FEATURE:
<223> OTHER INFORMATION: Synthetic primer

<400> SEQUENCE: 63
tttttttttt tttttttttt tttttttttt tttttttttt tttttttttt tttttttttt        60
ttttgctcct gtatctaaca gagc        84

<210> SEQ ID NO 64
<211> LENGTH: 51
<212> TYPE: DNA
<213> ORGANISM: Artificial sequence
<220> FEATURE:
<223> OTHER INFORMATION: Synthetic primer

<400> SEQUENCE: 64
taatacgact cactataggg agaccaccat gggtggcaag tggtcaaaaa g        51

<210> SEQ ID NO 65
<211> LENGTH: 51
<212> TYPE: DNA
<213> ORGANISM: Artificial sequence
<220> FEATURE:
<223> OTHER INFORMATION: Synthetic primer

<400> SEQUENCE: 65
taatacgact cactataggg agaccaccat gggtggcaag tggtcaaaac g        51

<210> SEQ ID NO 66
<211> LENGTH: 82
<212> TYPE: DNA
<213> ORGANISM: Artificial sequence
<220> FEATURE:
<223> OTHER INFORMATION: Synthetic primer -continued

<400> SEQUENCE: 66
tttttttttt tttttttttt tttttttttt tttttttttt tttttttttt tttttttttt    60
ttttccagta caggcaaaaa gc    82

<210> SEQ ID NO 67
<211> LENGTH: 81
<212> TYPE: DNA
<213> ORGANISM: Artificial sequence
<220> FEATURE:
<223> OTHER INFORMATION: Synthetic primer

<400> SEQUENCE: 67
tttttttttt tttttttttt tttttttttt tttttttttt tttttttttt tttttttttt    60
ttttcagtac aggcgaaaag c    81

<210> SEQ ID NO 68
<211> LENGTH: 82
<212> TYPE: DNA
<213> ORGANISM: Artificial sequence
<220> FEATURE:
<223> OTHER INFORMATION: Synthetic primer

<400> SEQUENCE: 68
tttttttttt tttttttttt tttttttttt tttttttttt tttttttttt tttttttttt    60
ttttccagta caggcaagaa gc    82

<210> SEQ ID NO 69
<211> LENGTH: 23
<212> TYPE: DNA
<213> ORGANISM: Human immunodeficiency virus

<400> SEQUENCE: 69
gctctattag atacaggagc aga    23

<210> SEQ ID NO 70
<211> LENGTH: 78
<212> TYPE: DNA
<213> ORGANISM: Human immunodeficiency virus

<400> SEQUENCE: 70
gagagtggtg gaacttctgg gacgcagcag tctcagggga ctacagaagg ggtgggaaac    60
ccttaaatat ctgggagg    78

<210> SEQ ID NO 71
<211> LENGTH: 57
<212> TYPE: DNA
<213> ORGANISM: Human immunodeficiency virus

<400> SEQUENCE: 71
gaggacggtg gagactctgg gacacagggg gtgggagatc ctcaaatacc tgaagaa    57

<210> SEQ ID NO 72
<211> LENGTH: 57
<212> TYPE: DNA
<213> ORGANISM: Human immunodeficiency virus

<400> SEQUENCE: 72

-continued gaggacagtg gagactctgg gacacagggg gtgggagatc ctcaaatacc tgaagaa                57

<210> SEQ ID NO 73
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 73
gggagaccac catgggaccc acctcccaat ccc                                          33

<210> SEQ ID NO 74
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 74
ggcagaccac catggaccca cctcccaatc cc                                           32

<210> SEQ ID NO 75
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 75
ggaagaccac catggaccca cctcccaatc cc                                           32

<210> SEQ ID NO 76
<211> LENGTH: 51
<212> TYPE: DNA
<213> ORGANISM: Artificial sequence
<220> FEATURE:
<223> OTHER INFORMATION: Synthetic primer

<400> SEQUENCE: 76
taatacgact cactataggg agaccaccat gggtggcaag tggtcaaaag g                      51

<210> SEQ ID NO 77
<211> LENGTH: 51
<212> TYPE: DNA
<213> ORGANISM: Artificial sequence
<220> FEATURE:
<223> OTHER INFORMATION: Synthetic primer

<400> SEQUENCE: 77
taatacgact cactataggg agaccaccat gggtggcaag tggtcaaaaa t                      51

PRIMERS AND PROBES FOR THE AMPLIFICATION AND DETECTION OF HIV GAG, REV AND NEF POLYNUCLEOTIDES

RELATED APPLICATIONS

This application is a 35 USC 371 national phase application of PCT/US2008/009185, filed Jul. 30, 2008, which claims benefit of U.S. Provisional Patent Application Ser. No. 60/962,510, filed Jul. 30, 2007, the contents of which are hereby incorporated by reference as if recited in full herein.

BACKGROUND OF THE INVENTION

Human immunodeficiency virus (HIV) infection rates and acquired immunodeficiency syndrome (AIDS) related death have reached pandemic proportions. According to the World Health Organization (WHO) and the joint United Nations Program on HIV/AIDS (UNAIDS), as of 2004, there were 39.4 million HIV infected adults and children, 4.9 million new infections (13,425 new infections every day), and 3.1 million AIDS related deaths had occurred worldwide. Recent projections from the WHO and UNAIDS, indicate that if the pandemic proceeds at its current rate there will be 45 million new HIV infections and 70 million deaths by 2020 (Stover et al., Lancet 2002 360:73-77).

Since its introduction in 1996, highly active antiretroviral therapy (3-drug combination therapy; "HAART") has significantly reduced HIV-associated morbidity and mortality. HAART is seen to have successfully suppressed viral replication long-term, facilitated partial immune restoration, and prolonged survival. However, the incidence of HAART induced drug toxicity and the emergence of drug resistance has increased every year since its introduction. In addition, HAART regimens are expensive, have complex dose schedules and have significant drug-drug interactions. Accordingly, a novel therapeutic intervention that could complement HAART, shorten time on HAART, or even replace HAART in some HIV-infected subjects, would be a significant addition the anti-HIV armamentarium.

Given the inadequacy of HAART, there is a need for new treatment options. An immune-based therapy that can boost an HIV-infected subject's immune response and specifically enhance a CTL responses against HIV-1 has been proposed as possible strategy to limit the use and/or need for anti-retroviral medication (Kinloch-de Loes (2004) J. Antimicrob. Chemother. 53:562-566). Although several cell-based immunotherapeutics have been developed using consensus sequences of the HIV-1 viral genome as immunogens in viral vectors, the results of these clinical trials have been disappointing in their ability to suppress viral replication.

HIV immunotherapies based on clade-specific consensus antigens have been investigated in over 80 clinical trials, however, the results demonstrate a consistent lack of efficacy (Garber et al. (2004) The Lancet 4:397-413; McMichael (2006) Annual Rev. Immunol 24:227-255; and Nabel (2001) Nature 410:1002-1007). While augmentation of immune responses to consensus sequences used for immunization was demonstrated, these therapies did not result in reduction of viral loads. Evidence suggests that the lack of HIV-protective immunity is due to sequence divergence between autologous and consensus antigens. Studies with overlapping peptides demonstrated that CTL recognizing autologous peptides encoded within a known HIV virus did not cross react with corresponding consensus sequences (Altfeld et al. (2001) J. Exp. Med. 193:169-180). In addition, HIV's high mutation rate results in novel mutant variants that encode point mutations within CTL epitopes and escape recognition by specific T cells. Studies on humans and non-human primates correlate virus escape from CTL with progression to AIDS (Goulder et al. (1999) Mature Medicine 5:1233-1235; Goulder et al. (2004) Nature 4:630-640; and Barouch et al. (2002) Nature 415:335-339). In addition, each patient creates a unique environment for its own viral evolution. Consequently, there is substantial mutational variation between the virus infecting the patient and the reference sequences upon which most HIV immunotherapies are based. Since virus sequence diversity defines HIV clades, therapies based on consensus antigens from one clade may have limited ability to cross control evolutionally divergent viruses from other clades. Accordingly, therapies based on autologous viral antigens would have broader applicability since the therapy would be perfectly matched to the virus species infecting each subject.

To date, the successful dendritic cell (DC)-based immunotherapies for HIV infected patients used an autologous virus as a source of immunogen. One clinical study demonstrated that an AT-inactivated whole autologous HIV virus particle-loaded autologous DC therapy prolonged suppression of viral load by more than 90% in 8 patients for at least one year (Lu et al. (2004) Nature Medicine 10:1359-13565). All 8 of the enrolled subjects also maintained CD4+ T-cell counts. More recently, a second independent clinical study confirmed the benefit of immunizing patients against autologous virus (Garcia et al. (2005) J.I.D. 191:1680-1685). Patients in the later study were immunized with DC pulsed with autologous plasma-derived heat-inactivated virus. After immunization and interruption of HAART, set-point plasma viral load decreased by at least 0.5 log(10) copies/mL relative to baseline in 4 of 12 patients. This response was associated with changes in HIV-1-specific CD4+ lymphoproliferative and CD8+ T cell responses. Although these clinical studies demonstrated the potential utility of an autologous DC therapy, the choice of whole inactivated HIV virus as an immunogen is not ideal and may have significant safety and practical limitations.

Commonly owned PCT Publication WO2006/031870, the contents of which are incorporated by reference, discloses a method for strain-independent RT-PCR amplification of selected HIV antigens (such as Gag, Rev, Nef and Vpr) to generate templates for in vitro transcribed (IVT) RNA. The IVT RNA can be used to transfect dendritic cells or other antigen presenting cells (APCs) to produce an autologous RNA-loaded APC based HIV therapy with far lower regulatory hurdles (as the final formulation lacks infectious virus) in comparison to inactivated virus or total RNA vaccines.

Due to the high mutation rate of HIV, a major obstacle to RT-PCR amplification of autologous viral sequences was the design of PCR primers capable of amplifying variant HIV strains present in an individual without prior knowledge of the variant target sequences. PCT Publication WO2006/031870 solves this problem by disclosing a multiplex RT-PCR strategy that allows reliable strain-independent amplification of highly polymorphic target antigens from any patient without the requirement of custom designing the primers for each of the variant viral sequences present in a particular individual. This approach to amplify HIV sequences in a clade-independent manner rests on the principles of multiplex RT-PCR technology. Pools of forward and reverse primers for each target gene (e.g., Gag, Rev, Vpr and Nef) are utilized such that most HIV strains will react with at least one forward and one reverse primer. Specifically, the amplification reactions use primer groups composed of primers that are complementary to a consensus target sequence as well as additional primers carrying compensatory mutations. A schematic diagram showing an embodiment of the RT-RCR amplification and in vitro transcription of HIV sequences strategy disclosed in WO2006/031870, using Rev as an example, is shown in FIG. 1. In FIG. 1, a Rev cDNA is made by reverse transcription using Rev specific primer group R8300, which contains multiple primer sequences. (Alternatively, the cDNA could be made using random primers to initiate reverse transcription.) The Rev cDNA is then amplified using three primary PCR reactions. Each primary PCR in this example utilizes the Rev R8300 reverse primer group, and one of three Rev forward primer groups (Rev F7750, Rev F7830, or Rev F7911). During the annealing step, the most complementary primer-template combination gives rise to a primary cDNA product. The primary cDNA is then amplified further in a secondary PCR reaction using groups of nested primers (the Rev T7 primer group and the Rev 64T primer groups are shown). Each 5' nested primer contains a promoter (e.g., a T7 promoter) for subsequent in vitro transcription of the resulting cDNA product, while each 3' nested primer preferably contains a 3' polyT tract that can be transcribed into a polyA tail. The HIV cDNA produced by this multiplex RT-PCR-mediated amplification of autologous RNA encoding HIV antigens from small volumes of infectious plasma encode a complex mixture representing multiple quasispecies present within a given subject. The HIV cDNA produced by the secondary PCR can then be used for in vitro transcription to produce mRNA encoding the variant viral antigens.

DCs transfected with this IVT mRNA processed and presented multiple autologous HIV antigens and induce antigen-specific CD8+ T cells. The simultaneous use of autologous viral antigens and DCs provide for a broad patient-specific immune response that could potentially have a better control of residual virus or a rebound of virus following the cessation of therapy. This strategy can induce broad immune responses and the simultaneous assault on all relevant epitopes may have the added benefit of driving the virus into a state of poor replicative fitness and potentially eventual clearance. In addition, using specific RNAs to encode the antigens of interest instead of whole virus-circumvents safety concerns. Furthermore, preliminary results from a Phase I/II clinical trial have demonstrated the safety of this approach in HIV patients.

Notwithstanding the success of the HIV amplification strategy disclosed in PCT Publication WO2006/031870, there is a need for primers that result in improved amplification of samples containing multiple quasispecies of HIV non-Clade B or Clade B nucleotides. In addition, it would be useful to develop primers that increase the yield of PCR products and/or in vitro transcripts. The present invention addresses these needs and provides additional advantages as well.

SUMMARY OF THE INVENTION

The inventors have discovered novel primers, methods and kits for the amplification of multiple species of HIV Rev, Gag and Nef nucleic acids. In one embodiment, the invention provides a composition comprising a Rev T7 promoter primer selected from the group consisting of:

(SEQ ID NO: 24)
$N_1N_2N_3N_4N_5$TAATACGACTCACTATAGGX6AGACCACCATGGACCCACC
TCCCAACC, (SEQ ID NO: 25)
$N_1N_2N_3N_4N_5$TAATACGACTCACTATAGGX6AGACCACCATGGACCCACC
TCCCAGCC, (SEQ ID NO: 26)
$N_1N_2N_3N_4N_5$TAATACGACTCACTATAGGX6AGACCACCATGGACCCACC
TCCCAGTT, (SEQ ID NO: 27)
$N_1N_2N_3N_4N_5$TAATACGACTCACTATAGGX6AGACCACCATGGACCCTTA
CCCCAACC, (SEQ ID NO: 28)
$N_1N_2N_3N_4N_5$TAATACGACTCACTATAGGX6AGACCACCATGGACCCTTA
CCCCAAAC, (SEQ ID NO: 29)
$N_1N_2N_3N_4N_5$TAATACGACTCACTATAGGX6AGACCACCATGGACCCTTA
CCCCAAGC, (SEQ ID NO: 17)
$N_1N_2N_3N_4N_5$TAATACGACTCACTATAGGX6AGACCACCATGTCAGACCC
ACCT, (SEQ ID NO: 18)
$N_1N_2N_3N_4N_5$TAATACGACTCACTATAGGX6AGACCACCATGTCAGACCC
GCCT, (SEQ ID NO: 19)
$N_1N_2N_3N_4N_5$TAATACGACTCACTATAGGX6AGACCACCATGTCAGACCC
TCCT, (SEQ ID NO: 20)
$N_1N_2N_3N_4N_5$TAATACGACTCACTATAGGX6AGACCACCATGTCAGACCC
ATAC, (SEQ ID NO: 21)
$N_1N_2N_3N_4N_5$TAATACGACTCACTATAGGX6AGACCACCATGTCAGATCC
ATAC, (SEQ ID NO: 22)
$N_1N_2N_3N_4N_5$TAATACGACTCACTATAGGX6AGACCACCATGTCAGACCC
TTAC,
and (SEQ ID NO: 23)
$N_1N_2N_3N_4N_5$TAATACGACTCACTATAGGX6AGACCACCATGTCAGACCC
CTAC,
or any combination thereof;

Wherein $N_6$ is G, A, C or T; and either $N_1$ is G, $N_2$ is A, $N_3$ is A and $N_4$ and $N_5$ are T or each of $N_1$ through $N_5$ are absent.

Such Rev T7 primer compositions can be combined with one or more Rev reverse primers in order to amplify HIV Rev sequences. Preferred Rev reverse primers are Rev 64T primers selected from the group consisting of SEQ ID NO:14, SEQ ID NO:15 and SEQ ID NO:16, or any combination thereof.

In another embodiment, the invention provides a composition comprising a Gag reverse primer selected from the group consisting of SEQ ID NO:42, SEQ ID NO:43, SEQ ID NO:44, SEQ ID NO:45, SEQ ID NO:46, SEQ ID NO:47 and SEQ ID NO:48, or any combination thereof. Such Gag reverse primer compositions can be combined with one or more Gag forward primers in order to amplify HIV Gag sequences. Preferred Gag forward primers include SEQ ID NO:30, SEQ ID NO:31, SEQ ID NO:32 and SEQ ID NO:33.

In another embodiment, the invention provides a Nef forward primer composition comprising the NEF forward primer F8235.2 of SEQ ID NO:58. In a preferred embodiment, this Nef forward primer composition further comprises the Nef F8235 forward primers of SEQ ID NO:49 and SEQ ID NO:50. Such Nef forward primer compositions can be combined with one or more Nef reverse primers in order to amplify HIV Nef sequences. Preferred Nef reverse primers include Nef R9069 reverse primers selected from the group consisting of SEQ ID NO:55, SEQ ID NO:56 and SEQ ID NO:57, or any combination thereof.

The primer compositions of the invention can be used for the amplification and/or detection of HIV nucleic acids. The invention further provides methods and kits for amplification of HIV nucleic acids. HIV nucleic acids amplified by the methods of the invention and RNA transcribed therefrom have many uses, including, but not limited to nucleic acid vaccines and for transfection of antigen presenting cells, which can then be used in immunotherapy.

BRIEF DESCRIPTION OF THE DRAWINGS

FIG. 8 shows the sequence alignment of Rev secondary amplicons from non-Clade-B patients IDR-099 and IDR-103. Sequences in dashed box in IDR-099 show the insertion; dashed lines in IDR-103 show deletion. Nucleotides in solid rectangles are mutations between IDR-099 and IDR-103. IDR-099 Clones 2, 3, 4, 6, 8, 9 and 10 (SEQ ID NO:70); IDR-103 Clones 6, 8, 9 and 10 (SEQ ID NO:71).

FIG. 22 shows successful amplification HIV Nef RNA from the plasma of subjects infected with diverse clades of HIV. Panels A-C show agarose gel resolution of Nef secondary cDNA amplified from the plasma of patient HTM 367 (Clade B, panel A), ICR-085 (Clade C, panel B) and HND 022 (Clade AG, panel C). The molecular weight marker in panels A and B is a 100 bp DNA ladder (Invitrogen). The molecular weight marker in panel C is the AmpliSize™ DNA ladder (BioRad). After reverse transcription reactions, the cDNAs were amplified in a primary PCR reaction using following groups: lane 1: Nef F8235 forward primer group together with the Nef R9069 reverse primer group; lane 2: Nef F8343 primer group together with the Nef R9069 reverse primer group. After the primary PCR reaction the primary amplicon was amplified with secondary PCR primer groups Nef T7 8343 and Nef 906964T. Panel D shows agarose gel resolution of cDNA obtained in preparative scale secondary PCR reactions corresponding to Gag, Vpr, Rev, and Nef antigens. M: 100 bp DNA ladder (Invitrogen). The molecular weight of representative DNA bands is indicated on the left. Panel E shows agarose gel resolution of IVT RNA corresponding to Gag (G), Vpr (V), Rev (R), and Nef (N) obtained by in vitro transcription using amplified PCR products from subjects plasma. M: molecular weight RNA ladder (Promega), representative marker sizes are indicated on the left.

FIG. 23 summarizes the productive amplification of Nef, Gag, Rev and Vpr from 30 HIV subjects. Samples were acquired as indicated in various geographical location; nd: data not available; viral load test was estimated by a clinical laboratory using either the Amplicor HIV Assay (Roche) or the bDNA assay (Bayer); copy/µL RNA: copy number of HIV RNA per microliter of purified eluate was calculated base on viral load assay assuming 100% recovery during RNA purification, the number of silica columns use and the volume of final eluate; copy/µL RT reaction calculated based on previous number.

BRIEF DESCRIPTION OF THE SEQUENCE LISTING

Figure 1:
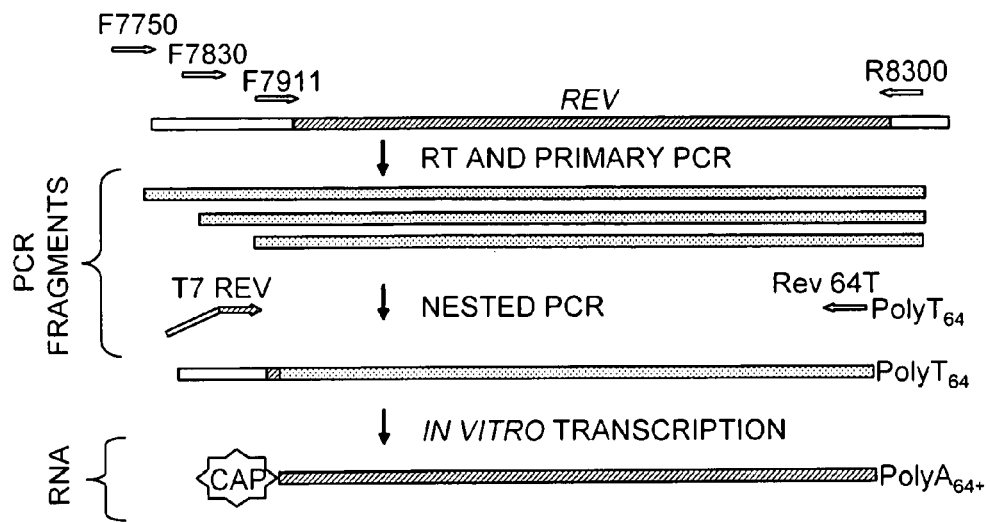
FIG. 1 is a Schematic overview of an RT-PCR amplification strategy, using Rev Exon 2 as an example. HIV RNA extracted from the plasma of a patient with HIV infection serves as a template for reverse transcriptase in a first strand cDNA reaction using a gene-specific group of primers. The first strand cDNA was divided among multiple PCR reactions containing multiplex groups of primers to produce a primary amplicon. The primary amplicons are then used as a template for secondary round of amplification. During the secondary PCR reaction, a T7 RNA polymerase binding site and an oligo dT stretch are incorporated into the secondary amplicon via the use oligonucleotides containing overhangs with these sequences. The Rev T7 forward primer contains an overhang encoding the sequence of a T7 RNA promoter, the bases ACC in a −3, −2 and −1 position of the initiator ATG codon for the antigen, as well as the ATG initiation codon that is not present in Rev exon 2. The 3' half of the nested Rev T7 forward primer was complimentary to the sequence immediately downstream of either the initiator ATG codon or the most 5' coding sequence amplified during the primary PCR amplification. The reverse primer also contained a poly$(T)_{64}$ overhang at its 5' end, which served as a template for a polyadenylation (polyA) sequence at the 3' end of the RNA molecule during transcription. The 3' half of the reverse primer was complementary to the sequence isolated in a primary PCR reaction. Open bar denotes regions outside of open reading frame of interest, hatched bar denotes RNA region exon 2 Rev, grey bar represent DNA intermediate products during amplification process

SEQ ID NO:1: HIV genome having the accession number NC_001802 in the Los Alamos National Laboratory HIV Sequence Database.
SEQ ID NO:2: Rev F7750 (a Rev forward primer).
SEQ ID NO:3: Rev F7750.1 (a Rev forward primer).
SEQ ID NO:4: Rev F7830 (a Rev forward primer).
SEQ ID NO:5: Rev F7830.1 (a Rev forward primer).
SEQ ID NO:6: Rev F7830.2 (a Rev forward primer).
SEQ ID NO:7: Rev F7911 (a Rev forward primer).
SEQ ID NO:8: Rev F7911.1 (a Rev forward primer).
SEQ ID NO:9: Rev R8300 (a Rev reverse primer).
SEQ ID NO:10: Rev R8300.1 (a Rev reverse primer).
SEQ ID NO:11: Rev R8300.2 (a Rev reverse primer).
SEQ ID NO:12: Rev T7 F7912 (a Rev forward T7 promoter primer).
SEQ ID NO:13: Rev T7 F7912.1 (a Rev forward T7 promoter primer).
SEQ ID NO:14: Rev R8300 64T (a Rev 64T reverse primer).
SEQ ID NO:15: Rev R8300.1 64T (a Rev 64T reverse primer).
SEQ ID NO:16: Rev R8300.2 64T (a Rev 64T reverse primer).
SEQ ID NO:17: REV T7 7912.2 (a Rev forward T7 promoter 9-overlap primer).
SEQ ID NO:18: REV T7 7912.3 (a Rev forward T7 promoter 9-overlap primer).
SEQ ID NO:19: REV T7 7912.4 (a Rev forward T7 promoter 9-overlap primer).
SEQ ID NO:20: REV T7 7912.5 (a Rev forward T7 promoter 9-overlap primer).
SEQ ID NO:21: REV T7 7912.6 (a Rev forward T7 promoter 9-overlap primer).
SEQ ID NO:22: REV T7 7912.7 (a Rev forward T7 promoter 9-overlap primer).
SEQ ID NO:23: REV T7 7912.8 (a Rev forward T7 promoter 9-overlap primer).
SEQ ID NO:24: REV T7 7912.15 (a Rev forward T7 promoter 16-overlap primer).
SEQ ID NO:25: REV T7 7912.16 (a Rev forward T7 promoter 16-overlap primer).
SEQ ID NO:26: REV T7 7912.17 (a Rev forward T7 promoter 16-overlap primer).
SEQ ID NO:27: REV T7 7912.18 (a Rev forward T7 promoter 16-overlap primer).
SEQ ID NO:28: REV T7 7912.19 (a Rev forward T7 promoter 16-overlap primer).
SEQ ID NO:29: REV T7 7912.20 (a Rev forward T7 promoter 16-overlap primer).
SEQ ID NO:30: Gag F124 (a Gag forward primer).
SEQ ID NO:31: Gag F304 (a Gag forward primer).
SEQ ID NO:32: Gag F334 (a Gag forward primer).
SEQ ID NO:33: Gag F334.1 (a Gag forward primer).
SEQ ID NO:34: Gag R1881 (a Gag reverse primer).
SEQ ID NO:35: Gag R1881.1 (a Gag reverse primer).
SEQ ID NO:36: Gag R1881.2 (a Gag reverse primer).
SEQ ID NO:37: Gag R1913 (a Gag reverse primer).
SEQ ID NO:38: Gag R1913.1 (a Gag reverse primer).
SEQ ID NO:39: Gag R1913.2 (a Gag reverse primer).
SEQ ID NO:40: Gag R1913.4 (a Gag reverse primer).
SEQ ID NO:41: Gag R1913.5 (a Gag reverse primer).
SEQ ID NO:42: Gag R 1883 (a Gag reverse primer).
SEQ ID NO:43: Gag R 1883.1 (a Gag reverse primer).
SEQ ID NO:44: Gag R 1883.2 (a Gag reverse primer).
SEQ ID NO:45: Gag R 1884 (a Gag reverse primer).
SEQ ID NO:46: Gag R 1884.1 (a Gag reverse primer).
SEQ ID NO:47: Gag R 1884.2 (a Gag reverse primer).
SEQ ID NO:48: Gag R 1884.3 (a Gag reverse primer).
SEQ ID NO:49: Nef F8235 (a Nef forward primer).
SEQ ID NO:50: Nef F8235.1 (a Nef forward primer).
SEQ ID NO:51: Nef F8343 (a Nef forward primer).
SEQ ID NO:52: Nef F8343.1 (a Nef forward primer).
SEQ ID NO:53: Nef F8343.2 (a Nef forward primer).
SEQ ID NO:54: Nef F8343.3 (a Nef forward primer).
SEQ ID NO:55: Nef R9069 (a Nef reverse primer).
SEQ ID NO:56: Nef R9069.1 (a Nef reverse primer).
SEQ ID NO:57: Nef R9069.2 (a Nef reverse primer).
SEQ ID NO:58: Nef F8235.2 (a Nef forward primer).
SEQ ID NO:59: Gag T7 F334 (a Gag T7 promoter primer).
SEQ ID NO:60: Gag T7 F334.1 (a Gag T7 promoter primer).
SEQ ID NO:61: Gag R1881 64T (a Gag 64T reverse primer).
SEQ ID NO:62: Gag R1881.1 64T (a Gag 64T reverse primer).

SEQ ID NO:63: Gag R1881.2 64T (a Gag 64T reverse primer).
SEQ ID NO:64: Nef T7 8343 (a Nef T7 forward primer).
SEQ ID NO:65: Nef T7 8343.1 (a Nef T7 forward primer).
SEQ ID NO:66: Nef 9069 64T (a Nef 64T reverse primer).
SEQ ID NO:67: Nef 9069.1 64T (a Nef 64T reverse primer).
SEQ ID NO:68: Nef 9069.2 64T (a Nef 64T reverse primer).
SEQ ID NO:69: Query sequence corresponding to a region of Gag.
SEQ ID NO:70: Portion of Rev from IDR-099 clones.
SEQ ID NO:71: portion of Rev from IDR-103 clones.
SEQ ID NO:72: portion of HIV.
SEQ ID NO:73: 5' end of Rev IVT NRAs produced from secondary Rev amplicons made using a Rev Hi T7 7912 primer group (corresponding to the primers of SEQ ID NO:24-29, wherein $N_1$ is G, $N_2$ is A, $N_3$ is A, $N_4$ and $N_5$ are T and $N_6$=G) together with the Rev 8300 64T primer group.
SEQ ID NO:74: Same as SEQ ID NO:73, except $N_6$=C (C is substituted for the +3 G).
SEQ ID NO:75: Same as SEQ ID NO:73, except $N_6$=A (A is substituted for the +3 G).
SEQ ID NO:76: New HIV primer annealing region shown in Table 13.
SEQ ID NO:77: New HIV primer annealing region shown in Table 13.

DETAILED DESCRIPTION

The invention disclosed herein relates to novel nucleic acid primers for amplification and/or detection of HIV nucleic acids, and related methods. The practice of the present invention employs, unless otherwise indicated, conventional techniques of molecular biology (including recombinant techniques), microbiology, cell biology, biochemistry and immunology, which are within the skill of the art. Such techniques are explained fully in the literature. These methods are described in the following publications. See, e.g., Sambrook et al. Molecular Cloning: A Laboratory Manual, 3rd edition (2001); Current Protocols in Molecular Biology (F. M. Ausubel et al. eds. (1987)); the series Methods in Enzymology (Academic Press, Inc.); PCR: A Practical Approach (M. MacPherson et al. IRL Press at Oxford University Press (1991)); and PCR 2: A Practical Approach (M. J. MacPherson, B. D. Hames and G. R. Taylor eds. (1995)).

As used herein, certain terms may have the following defined meanings. The singular forms "a," "an" and "the" include plural references unless the context clearly dictates otherwise. For example, the term "a primer" includes a plurality of primers, including mixtures thereof.

"Amplification" refers to nucleic acid amplification procedures using primers and nucleic acid polymerase that generate multiple copies of a target nucleic acid-sequence. Such amplification reactions are known to those of skill in the art, and include, but are not limited to, the polymerase chain reaction ("PCR", see U.S. Pat. Nos. 4,682,195, 4,683,202 and 4,965,188), RT-PCR (see U.S. Pat. Nos. 5,322,770 and 5,310,652) the ligase chain reaction ("LCR", see EP 0 320 308), NASBA or similar reactions such as TMA described in U.S. Pat. No. 5,399,491 and gap LCR ("GLCR", see U.S. Pat. No. 5,427,202). If the nucleic acid target is RNA, RNA may first be copied into a complementary DNA strand using a reverse transcriptase (see U.S. Pat. Nos. 5,322,770 and 5,310,652). An "amplicon" refers to nucleic acids that were synthesized using amplification procedures.

The term "antigen presenting cells (APC)" refers to a class of cells capable of presenting one or more antigens in the form of antigen-MHC complex recognizable by specific effector T cells of the immune system. APCs include, but are not limited to, macrophages, B-cells and dendritic cells, such as immature dendritic cells, mature dendritic cells, plasmacytoid dendritic cells, Langerhans cells and artificial antigen presenting cells.

As used herein, the term "consisting essentially of" shall mean excluding other elements of any essential significance to the combination. Thus, a composition consisting essentially of the elements as defined herein would not exclude trace contaminants from the isolation and purification method, biological buffers and pharmaceutically acceptable carriers, such as phosphate buffered saline, preservatives, etc. When used in the context of a primer, the term "consisting essentially of" means the primer or oligonucleotide shall not have more than 10 additional nucleotide residues at the 5' end of a referenced sequence, nor more than 10 additional nucleotide residues at the 3' end of a referenced sequence. For example, a primer consisting essentially of an oligonucleotide of SEQ ID NO:X may have from 0 to 10 additional nucleotides at the 5' end of SEQ ID NO:X, and from 1 to 10 additional nucleotides at the 3' end of SEQ ID NO:X. Preferably, a primer consisting essentially of a reference oligonucleotide has no more than 5, 6, 7, 8 or 9 additional nucleotides at each of the 5' and 3' ends of the reference oligonucleotide. Most preferably, a primer consisting essentially of a reference oligonucleotide has no more than 1, 2, 3 or 4 additional nucleotides at each of the 5' and 3' ends of the reference oligonucleotide.

As used herein, a composition comprising a primer consisting essentially of an oligonucleotide selected from the group consisting of: SEQ ID NO:X, SEQ ID NO:Y and SEQ ID NO:Z, may contain one or any combination of the oligonucleotides of SEQ ID NO:X, SEQ ID NO:Y and SEQ-ID NO:Z, with from 0 to 10 additional nucleotides on either 5' and/or 3' end of each oligonucleotide. The composition itself comprises such primers, and so may contain additional element as well.

"HIV RNA" includes genomic (viral) HIV RNA and HIV mRNA (spliced or unspliced), as well as RNA produced by in vitro transcription of HIV amplicons prepared by the methods of the invention.

"HIV variants" or "variants of HIV" or "HIV strain" refers to any variety of HIV, and includes, but is not limited to, HIV-1 and HIV-2, HIV-1 Groups M, N and O, all HIV subtypes (clades), including HIV-1 subtypes A1, A2, B, C, C, F1, F2, G, H, J and K, variants of clades, all quasi-species thereof and circulating recombinant forms. As the term "strain" is used herein, two HIV isolates that differ by a single nucleotide would be considered two different "strains" of HIV. The term groups is commonly used to refer to the HIV-1 lineages M, N and O. The term subtypes is used to refer to the major clades within a group. There is further sequence variability within subtypes. Circulating Recombinant Form (CRF) describes a recombinant lineage, which plays an important role in the HIV pandemic. The CRF members commonly share a similar or identical mosaic structure i.e., they descend from the same recombination event(s). Descriptions and maps of CRFs and links to HIV sequences can be found at hiv.lanl.gov/content/hiv-db/CRFs/CRF.html.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragment thereof can be isolated, purified, concentrated, etc., but does not require "isolation" to distinguish it from its naturally occurring counterpart. In addition, a "concentrated", "separated" or "diluted" polynucleotide, peptide, polypeptide, protein, antibody, or fragment(s) thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragment(s) thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as its glycosylation pattern.

"mRNA" means a translatable RNA. The mRNA will contain a ribosome binding site and start codon. Preferably, the mRNA will also contain a 5' cap, stop codon and polyA tail.

"Multiplex polymerase chain reaction" is a variation of PCR in which two or more target sequences are simultaneously amplified in a single amplification reaction using multiple pairs of primers. As non-limiting examples, multiplex amplification includes amplification reactions of different genes, different alleles of a single gene and/or different fragments of a single gene. Methods for optimizing multiplex PCR conditions are disclosed in Abravaya et al. J Clinical Microbiol 2000 38:716-723; Kremer at al. J Clin Microbiol 2004 42:3017-3022; Garcia-Canas et al. Electrophoresis 2004 25:2219-2226; and Markoulatos et al. J Clin Lab Anal 2003 17:108-12, the contents of which are incorporated by reference.

The terms "polynucleotide", "nucleic acid" and "nucleic acid molecule" are used interchangeably to refer to polymeric forms of nucleotides of any length. The polynucleotides may contain deoxyribonucleotides, ribonucleotides, and/or their analogs. Polynucleotides may have any three-dimensional structure, and include single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In addition to a native nucleic acid molecule, a nucleic acid molecule of the present invention may also comprise modified nucleic acid molecules.

By "primer" is meant an oligonucleotide of 9 to 150 nucleotides in length that can be used in an amplification reaction. A primer can be used for purposes other than amplification, such as reverse transcription, hybridization, detection, etc. By "forward primer" is meant a primer that can be extended by a RNA polymerase or DNA polymerase into a nucleic acid that corresponds to the sequence of a sense strand or translated mRNA. By "reverse primer" is meant a primer that can be extended by a RNA polymerase, reverse transcriptase or DNA polymerase into a nucleic acid that is complementary to the sense strand or translated mRNA. "Primer pair" refers to forward and reverse primers that can be used in amplification reactions to produce an amplicon.

The term "RNA" refers to polymeric forms of ribonucleotides of any length, wherein the ribonucleotides or ribonucleotide analogs are joined together by phosphodiester bonds. The term "RNA" includes, for example, single-stranded, double-stranded and triple helical molecules, primary transcripts, mRNA, tRNA, rRNA, in vitro transcripts, in vitro synthesized RNA, branched polyribonucleotides, isolated RNA of any sequence, and the like.

Improved HIV Rev Primers, Kits and Amplification Methods

As discussed above, commonly owned PCT publication WO2006/031870 discloses successful RT-PCR amplification of HIV Clade B RNA encoding Gag, Vpr, Rev, and Nef antigens. Primers disclosed in WO2006/031870 for amplification of Rev nucleic acids are reproduced in part in Table 1. The sequences of the primers in Table 1 were based on analysis of all 367 HIV genome sequences contained in the Los Alamos HIV database (www.hiv.lanl.gov/content/index) at the time of their design. The numbers in the primer names correspond to the position of their 5' nucleotide with respect to the HIV genome having accession number NC_001802 in the Los Alamos National Laboratory HIV Sequence Database (SEQ ID NO:1). An "F" or "T7" in a primer name designates a forward (sense strand) primer, while an "R" or "64T" in a primer name designates a reverse (antisense strand) primer.

The full length Rev mRNA is formed in the course of a trans-splicing reaction, which is not possible to reproduce in vitro. Since exon 2 of Rev is larger than exon 1, primers were to amplify exon 2 only. An ATG translational initiation codon was introduced in a context of secondary nested forward primer (see the underlined ATG sequence in Rev F7912 primers shown in Table 1).

TABLE 1*

| Rev primers disclosed in WO2006/031870 | | |
|---|---|---|
| Primer Group (PG) Primer Name | Sequence (5'->3') | SEQ ID NO: |
| PG: Rev F7750 | | |
| Rev F7750 | GGGATTTGGGGTTGCTCTGG | 2 |
| Rev F7750.1 | GGGATTTGGGGCTGCTCTGG | 3 |
| PG: Rev F7830 | | |
| Rev F7830 | TGATAGTAGGAGGCTTGGTAGG | 4 |
| Rev F7830.1 | TGATAGTAGGAGGCTTTAGG | 5 |
| Rev F7830.2 | TGATAGTAGGAGGCTTGgTAGG | 6 |
| PG: Rev F7911 | | |
| Rev F7911 | GTTAGGCAGGGATATTCACC | 7 |
| Rev F7911.1 | GTTAGGCAGGGATAcTCACC | 8 |

TABLE 1*-continued

Rev primers disclosed in WO2006/031870

| Primer Group (PG) Primer Name | Sequence (5'->3') | SEQ ID NO: |
|---|---|---|
| PG: Rev F8300 | | |
| Rev R8300 | CCCTGTCTTATTCTTCTAGG | 9 |
| Rev R8300.1 | CCCTGTCTTATTCTTacAGG | 10 |
| Rev R8300.2 | CCCTGTCTTATTCTTgTAGG | 11 |
| PG: Rev T7 F7912 | | |
| Rev T7 F7912 | TAATACGACTCACTATAGGGAGACCACC<u>ATG</u>GACCCACCTCCC | 12 |
| Rev T7 F7912.1 | TAATACGACTCACTATAGGGAGACCACC<u>ATG</u>GACCCgCCTCCC | 13 |
| PG: Rev R8300 64T | | |
| Rev R8300 647 | (T)$_{64}$CCCTGTCTTATTCTTCTAGG | 14 |
| Rev R8300.1 64T | (T)$_{64}$CCCTGTCTTATTCTTacAGG | 15 |
| Rev R8300.2 64T | (T)$_{64}$CCCTGTCTTATTCTTgTAGG | 16 |

*Nucleotides in upper case are complementary to predominant sequence within the region of interest. Nucleotides in lower case indicate compensatory point mutations complementary to described mutations within target region. The protein translation start codon ATG in T7 Rev F7912 is underlined.

In one Rev amplification protocol described in WO2006/031870 and schematically shown in FIG. 1, HIV viral RNA was isolated from patient serum and Rev cDNA was produced from the viral RNA by reverse transcription. The Rev cDNA was then amplified in three separate primary polymerase chain reactions (PCRs) using one of the following three forward and reverse primer group combinations: 1) the Rev F7750 primer group with the Rev R8300 primer group, 2) the Rev F7830 primer group with the Rev R8300 primer group and 3) the Rev F7911 primer group with the Rev R8300 primer group. An aliquot of the amplified cDNA from each primary PCR was amplified in a secondary PCR using forward primer group Rev T7 7912 and reverse primer group Rev R8300 64T. cDNA produced by the secondary PCR was then used as a template for in vitro transcription (IVT) to produce a Rev IVT mRNA. Transfection of dendritic cells with the Rev IVT mRNA resulted in expression of Rev protein in the transfected DC, antigen processing and presentation. However, the present inventors observed that this amplification protocol did not produce optimal amplification of Rev cDNA from the plasma of patients infected with Clade C HIV.

Analysis of the Rev primers in Table 1 using the Primalign module of the Los Alamos HIV database, which had expanded to contain 625 sequences as of June 2006, showed that the homology of HIV sequences to primer groups Rev F 7750, Rev F 7830, Rev F 7911, Rev R 8300, and Rev R 8300 64T was preserved despite the introduction of many new HIV genomes into the Los Alamos database since the design of these primers in 2004. However, the sequences of non-Clade B genomes corresponding to the Rev 7912 region were divergent from the Rev T7 7912 primers listed in Table 1.

Based on this analysis, two novel groups of Rev T7 7912 secondary primers, designated Rev T7 7912 9-overlap primers and Rev T7 7912 16-overlap primers, were designed to include prevalent mutations found in non-Clade B HIV genomes. The new primers and primer groups are listed in Table 2. The "9-overlap" and "16-overlap" nomenclature refers to the number of nucleotides of the primer that anneal to HIV genome (i.e., there are nine nucleotides at the 3' end of Rev T7 9-overlap primer that anneal to HIV viral template, sixteen nucleotides at the 3' end of Rev T7 16-overlap primer that anneal to HIV viral template).

TABLE 2**

Novel Rev primers

| Primer Groups (PG)/ Primer Name | Sequence (5'->3') | SEQ ID NO: |
|---|---|---|
| PG: Rev T7 7912 9-overlap | | |
| REV T7 7912.2 | N$_1$N$_2$N$_3$N$_4$N$_5$T<u>AATACGACTCACTATAGGX$_6$AGA</u>CCACC<u>ATG</u>CA <u>GACCCAC CT</u> | 17 |
| REV T7 7912.3 | N$_1$N$_2$N$_3$N$_4$N$_5$T<u>AATACGACTCACTATAGGX$_6$AGA</u>CCACC<u>ATG</u><u>GACCCgC CT</u> | 18 |
| REV T7 7912.4 | N$_1$N$_2$N$_3$N$_4$N$_5$T<u>AATACGACTCACTATAGGX$_6$AGA</u>CCACC<u>ATG</u>TCA<u>GACCCtC CT</u> | 19 |
| REV T7 7912.5 | N$_1$N$_2$N$_3$N$_4$N$_5$T<u>AATACGACTCACTATAGGX$_6$AGA</u>CCACC<u>ATG</u>CA <u>GACCCat aC</u> | 20 |

TABLE 2**-continued

Novel Rev primers

| Primer Groups (PG)/ Primer Name | Sequence (5'->3') | SEQ ID NO: |
|---|---|---|
| REV T7 7912.6 | $N_1N_2N_3N_4N_5$TAATACGACTCACTATAGGX$_6$AGACCACCATGTCAGAtCCatac | 21 |
| REV T7 7912.7 | $N_1N_2N_3N_4N_5$TAATACGACTCACTATAGGX$_6$AGACCACCATGCAGACCCttac | 22 |
| REV T7 7912.8 | $N_1N_2N_3N_4N_5$TAATACGACTCACTATAGGX$_6$AGACCACCATGCAGACCCctac | 23 |
| PG: Rev T7 7912 16-overlap | | |
| T7 REV 7912.15 | $N_1N_2N_3N_4N_5$TAATACGACTCACTATAGGX$_6$AGACCACCATGGACCCACCTCCCAACC | 24 |
| T7 REV 7912.16 | $N_1N_2N_3N_4N_5$TAATACGACTCACTATAGGX$_6$AGACCACCATGGACCCACCTCCCAgCC | 25 |
| T7 REV 7912.17 | $N_1N_2N_3N_4N_5$TAATACGACTCACTATAGGX$_6$AGACCACCATGGACCCACCTCCCAgtt | 26 |
| T7 REV 7912.18 | $N_1N_2N_3N_4N_5$TAATACGACTCACTATAGGX$_6$AGACCACCATGGACCCttacCCCAACC | 27 |
| T7 REV 7912.19 | $N_1N_2N_3N_4N_5$TAATACGACTCACTATAGGX$_6$AGACCACCATGGACCCttacCCCAAaC | 28 |
| T7 REV 7912.20 | $N_1N_2N_3N_4N_5$TAATACGACTCACTATAGGX$_6$AGACCACCATGGACCCttacCCCAAgC | 29 |

**Nucleotides in regular font represent the HIV consensus sequence within the region of interest. Nucleotide in lower case indicate point mutations of HIV sequences cataloged in the Los Alamos database. The protein translation start codon (ATG) present in the T7 Rev F 7912 primer groups is represented by a solid underline. The T7 promoter sequence is shown with a dotted underline. When $X_1$ through $X_5$ are absent, the −17 to +6 consensus sequence of the T7 promoter is present (when $X_6$ = G), wherein $X_5$ corresponds to position −17 of the T7 promoter. When $X_1$ = G, $X_2$ = A, $X_3$ = A, and $X_4$ and $X_5$ = T, the −22 to +6 of the 17 promoter is present, wherein $X_1$ through $X_5$ corresponds to position −22 to −18 of the T7 promoter. $X_6$ can be G, A, C or T). The "9-overlap" and "16 overlap" portion of these sequences are shown with a wavy underline.

The new primer groups were tested by amplification of Rev from HIV non-Clade B patient samples. The Rev T7 7912 9-overlap and 16-overlap primer groups (wherein $N_1$ through $N_5$ are absent and $N_6$=G), when combined with the Rev 88300 64T primer group, showed a substantial improvement in the secondary amplification and purity Rev non-Clade B cDNA in comparison to the Rev T7 F7912 primer group shown in Table 1. The Rev cDNA produced by these secondary amplifications was efficiently transcribed in vitro to produce IVT RNA. The expression of Rev protein encoded by the IVT RNA was examined both in vitro and in vivo translation systems; and Western blot analysis confirmed the identity of Rev protein. The new Rev secondary PCR primers were tested with Clade B samples, and the results demonstrate that the new primers work as well as if not better for amplification from plasma infected with Clade B HIV. Accordingly, the Rev T7 7912 9-overlap primers and the Rev T7 7912 16-overlap primers are useful for universal amplification and/or detection of all HIV Rev nucleic acids.

Additional modifications to the Rev T7 7912 9-overlap and 16-overlap primers further improved transcriptional or translational expression. For example, the addition of the −22 to −18 sequence (GAATT) of the T7 promoter to the 5' end of the new primer groups improves efficiency of transcription of Rev IVT NRA from the Rev cDNA template produced by amplification using such primers. In Rev T7 7912 9-overlap and 16-overlap primers shown in Table 2 above, when nucleotides $N_1$ through $N_5$ are absent, the −17 to +6 sequence of the T7 promoter is present. When $N_1$ is G, $N_2$ is A, $N_3$ is A and $N_4$ and $N_5$ are T, the −22 to +6 sequence of the T7 promoter is present.

Substitution of the G nucleotide at the +6 position of the T7 promoter for any other nucleotide (A, C or T) improves both the in vitro and in vivo translational efficiency of Rev IVT RNA transcribed from cDNA amplified using primers with this substitution. The +6 position of the 77 promoter shown by dashed underline in the Rev T7 7912 9-overlap and 16-overlap primers listed in Table 2 is represented by nucleotide $N_6$, which can be A, C, T or G.

Accordingly, in one aspect, the invention provides a composition, comprising at least one or a combination of Rev T7 promoter primers selected from the group consisting of:

(SEQ ID NO: 24)
$N_1N_2N_3N_4N_5$TAATACGACTCACTATAGGX6AGACCACCATGGACCCACC
TCCCAACC, (SEQ ID NO: 25)
$N_1N_2N_3N_4N_5$TAATACGACTCACTATAGGX6AGACCACCATGGACCCACC
TCCCAGCC, (SEQ ID NO: 26)
$N_1N_2N_3N_4N_5$TAATACGACTCACTATAGGX6AGACCACCATGGACCCACC
TCCCAGTT,

-continued

N₁N₂N₃N₄N₅TAATACGACTCACTATAGGX6AGACCACCATGGACCCTTA
CCCCAACC,
(SEQ ID NO: 27)

N₁N₂N₃N₄N₅TAATACGACTCACTATAGGX6AGACCACCATGGACCCTTA
CCCCAAAC,
(SEQ ID NO: 28)

N₁N₂N₃N₄N₅TAATACGACTCACTATAGGX6AGACCACCATGGACCCTTA
CCCCAAGC,
(SEQ ID NO: 29)

N₁N₂N₃N₄N₅TAATACGACTCACTATAGGX6AGACCACCATGTCAGACCC
ACCT,
(SEQ ID NO: 17)

N₁N₂N₃N₄N₅TAATACGACTCACTATAGGX6AGACCACCATGTCAGACCC
GCCT,
(SEQ ID NO: 18)

N₁N₂N₃N₄N₅TAATACGACTCACTATAGGX6AGACCACCATGTCAGACCC
TCCT,
(SEQ ID NO: 19)

N₁N₂N₃N₄N₅TAATACGACTCACTATAGGX6AGACCACCATGTCAGACCC
ATAC,
(SEQ ID NO: 20)

N₁N₂N₃N₄N₅TAATACGACTCACTATAGGX6AGACCACCATGTCAGATCC
ATAC,
(SEQ ID NO: 21)

N₁N₂N₃N₄N₅TAATACGACTCACTATAGGX6AGACCACCATGTCAGACCC
TTAC,
and
(SEQ ID NO: 22)

N₁N₂N₃N₄N₅TAATACGACTCACTATAGGX6AGACCACCATGTCAGACCC
CTAC;
(SEQ ID NO: 23)

In one embodiment, the composition comprises a combination of at least two, preferably at least three, four, five or six, Rev T7 F7912 16-overlap primers selected from the group consisting of SEQ ID NO:24, SEQ ID NO:25, SEQ ID NO:26, SEQ ID NO:27, SEQ ID NO:28 and SEQ ID NO:29. In another embodiment, the composition comprises a combination of at least two, preferably at least three, four, five, six or seven of the Rev T7 F7912 9-overlap primers selected from the group consisting of SEQ ID NO:17, SEQ ID NO:18, SEQ ID NO:19, SEQ ID NO:20, SEQ ID NO:21, SEQ ID NO:22 and SEQ ID NO:23.

For amplification of HIV nucleic acids, any of the Rev T7 primer compositions can be combined with a Rev reverse primer or primers, such as, but not limited to, one or more Rev R8300 64T primers selected from the group consisting of SEQ ID NO:14, SEQ ID NO:15 and SEQ ID NO:16.

Accordingly, in one embodiment, the invention provides a composition comprising:
a) at least one or a combination of Rev T7 7912 forward primers selected from the group consisting of SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28 and SEQ ID NO:29; and
b) at least one or a combination of Rev R8300 64T reverse primers selected from the group consisting of SEQ ID NO:14, SEQ ID NO:15 and SEQ ID NO:16.

Kits comprising the above forward and reverse primer compositions are provided, wherein the kit further comprises dNTPs, a buffer (1× or concentrated) suitable for amplification and/or a thermostabile DNA polymerase. In addition, the kit may also contain a reverse transcriptase and/or non-infectious HIV control templates for amplification. The kits are useful for the identification and quantitation of pathogen variants and for preparation of vaccines.

In another embodiment, the invention provides a method for amplifying an HIV Rev nucleic acid, comprising carrying out a polymerase chain reaction using at least one or a combination of Rev T7 7912 forward primers selected from the group consisting of SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28 and SEQ ID NO:29; and at least one or a combination of Rev R8300 64T reverse primers selected from the group consisting of SEQ ID NO:14, SEQ ID NO:15 and SEQ ID NO:16.

Improved HIV Gag Primers, Kits and Amplification Methods

Figure 2:
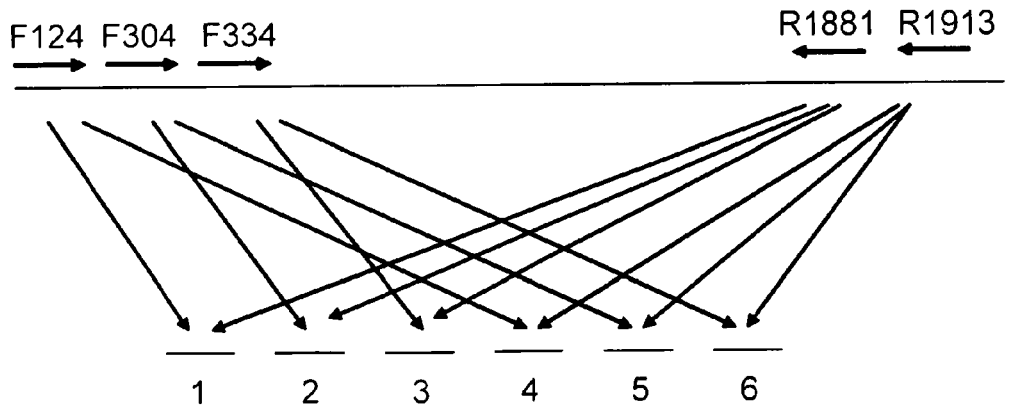
FIG. 2 is a schematic representation of primer group combinations for amplification of Gag cDNA in primary PCR.

PCT publication WO2006/031870 discloses a scheme for amplification of HIV Gag cDNA utilizing a combination of three primary forward groups of primers and two primary reverse groups of primers. The combination of each forward primer group with each reverse primer group results in six primary Polymerase Chain Reaction (PCR) amplification reactions (FIG. 2). The sequences of the Gag forward and reverse primers designated in FIG. 2 are shown in Table 3.

TABLE 3

Sequences of Selected Gag primers Disclosed in WO2006/031870

| Primer Group | Primer Name | Sequence (5' to 3') | SEQ ID NO: |
|---|---|---|---|
| | Gag F124 | ACTCTGGTAACTAGAGATCC | 30 |
| | Gag F304 | AATTTTGACTAGCGGAGGC | 31 |
| PG: Gag F334 | Gag F334 | AGATGGGTGCGAGAGCGT | 32 |
| | Gag F334.1 | AGATGGGTGCGAGAcCGT | 33 |
| PG: Gag R1881 | Gag R1881 | GCTCCTGTATCTAATAGAGC | 34 |
| | Gag R1881.1 | GCTCCTGTATCTAATAaAGC | 35 |
| | Gag R1881.2 | GCTCCTGTATCTAAcAGAGC | 36 |
| G: Gag R1913 | Gag R1913 | TTTGGTTTCCATCTTCCTGG | 37 |
| | Gag 1913.1 | TTTGGTTTCCATCTTCCTGc | 38 |
| | Gag R1913.2 | TTTcGTTTCCATCTcCCTGG | 39 |
| | Gag R1913.4 | TTTGGTTTCCATtTcCCTGG | 40 |
| | Gag R1913.5 | TTTGGTTTCCATtTTCCTGG | 41 |

The nucleotides in upper case font are complementary to the most common sequence within the HIV region of interest. The nucleotides in lower case font are complementary to mutations found within target region.

The present inventors found that amplification of HIV Clade C Gag nucleic acids was not always optimal when using the Gag R1881 primer group with any of the Gag F124, Gag F304 or the Gag F334 primer groups. This could be due to the GC nucleotides present at both the 5' and 3' ends of each primer in the Gag R1881 primer group, which may allow the primers to form relatively stable homodimer structures. In order to eliminate the possibility of stable primer dimer formation, two new primer groups, the Gag R1883 primer group and the Gag R1884 primer group (see Table 4), were designed to move the primer annealing site downstream two or three nucleotides so that the GC sequences excluded from the 5' and 3' ends of the primers (see FIG. 3). In addition, primer Gag R1884.3 contains degenerate mutations that are compensatory to Clade C sequences (FIG. 3) in order to allow for efficient amplification of more HIV genomes, including Clade C.

TABLE 4

Novel Reverse Primers for Amplification of Gag Nucleic Acids

| Primer Groups | Primer Name | Sequence (5' to 3') | SEQ ID NO: |
|---|---|---|---|
| Gag R1883 | Gag R 1883 | CTGCTCCTGTATCTAATAGA | 42 |
|  | Gag R 1883.1 | CTGCTCCTGTATCTAATAaA | 43 |
|  | Gag R 1883.2 | CTGCTCCTGTATCTAAcAGA | 44 |
| Gag R 1884 | Gag R 1884 | TCTGCTCCTGTATCTAATAG | 45 |
|  | Gag R 1884.1 | TCTGCTCCTGTATCTAATAa | 46 |
|  | Gag R 1884.2 | TCTGCTCCTGTATCTAAcAG | 47 |
|  | Gag R 1884.3 | TCTGCTCCTGTgTCTAAgAG | 48 |

Nucleotides in upper case are complementary to predominant sequence with the region of interest. Nucleotides in lower case indicate compensatory point mutations complementary to mutations within target region.

Both the Gag R1883 and Gag R1884 primer groups were tested with multiple subjects and demonstrated an enhanced amplification pattern as compared with Gag R1881 at the same concentrations. Accordingly, in one aspect, the invention provides a composition comprising a Gag reverse primer selected from the group consisting of SEQ ID NO:42, SEQ ID NO:43, SEQ ID NO:44, SEQ ID NO:45, SEQ ID NO:46, SEQ ID NO:47 and SEQ ID NO:48, or any combination thereof.

In one embodiment, a Gag R1883 reverse primer composition comprises SEQ ID NO:42, SEQ ID NO:43 and SEQ ID NO:44. In another embodiment, a Gag R1884 reverse primer composition comprises SEQ ID NO:45, SEQ ID NO:46, SEQ ID NO:47 and SEQ ID NO:48. The Gag R1884 primer group (SEQ ID NO:45, SEQ ID NO:46, SEQ ID NO:47 and SEQ ID NO:48) is preferred over the Gag R1883 primer group due to slightly better performance in Clade B, more noticeable improvement in C subjects, and theoretical broader coverage of quasispecies.

The Gag R1883 primers and the Gag R1884 primers of the invention can be combined with Gag forward primers in order to amplify Gag nucleic acids. Accordingly, in one embodiment, the invention provides a composition comprising:
 a) a Gag reverse primer selected from the group consisting of SEQ ID NO:42, SEQ ID NO:43, SEQ ID NO:44, SEQ ID NO:45, SEQ ID NO:46, SEQ ID NO:47 and SEQ ID NO:48, or any combination thereof; and
 b) a Gag forward primer selected from the group consisting of SEQ ID NO:30, SEQ ID NO:31, SEQ ID NO:32 and SEQ ID NO:33, or any combination thereof.

Preferred Gag primer compositions comprise the Gag R1884 primer group (SEQ ID NOs:45-48) with Gag F124 (SEQ ID NO:30); or the Gag R1884 primer group with Gag F304 (SEQ ID NO:31); or the Gag R1884 primer group with the Gag F334 primer group (SEQ ID NO:32-33). Alternatively, the Gag reverse primer group R1883 (SEQ ID NOs: 42-44) can be combined with any of the foregoing Gag forward primers or primer groups. The Gag primers and Gag primer groups of the invention are useful for amplification and detection of HIV Gag nucleic acids.

The invention further provides a kit comprising:
 a) a Gag reverse primer selected from the group consisting of SEQ ID NO:42, SEQ ID NO:43, SEQ ID NO:44, SEQ ID NO:45, SEQ ID NO:46, SEQ ID NO:47 and SEQ ID NO:48 or any combination thereof;
 b) a Gag forward primers selected from the group consisting of SEQ ID NO:30, SEQ ID NO:31, SEQ ID NO:32 and SEQ ID NO:33, or any combination thereof; and
 c) dNTPs, a buffer suitable for amplification and/or a thermostabile DNA polymerase.

The kit may also contain a reverse transcriptase and/or non-infectious HIV control templates for amplification. The kits are useful for the identification and quantitation of pathogen variants and for preparation of vaccines.

In another embodiment, the invention provides a method for amplifying an HIV Gag nucleic acid, comprising carrying out a polymerase chain reaction using at least one or a combination of Gag forward primers selected from the group consisting of SEQ ID NO:30, SEQ ID NO:31, SEQ ID NO:32 and SEQ ID NO:33; and at least one or a combination of Gag reverse primers selected from the group consisting SEQ ID NO:42, SEQ ID NO:43, SEQ ID NO:44, SEQ ID NO:45, SEQ ID NO:46, SEQ ID NO:47 and SEQ ID NO:48.

Novel Nef Primer and Amplification Methods

PCT publication WO2006/031870 discloses Nef forward primer group F8235 and Nef reverse primer group R9069, which are useful for the amplification and detection of Nef nucleic acids. The sequences of the primers in these groups are shown in Table 5.

TABLE 5

NEF Primer Groups Disclosed in PCT publication WO2006/031870

| Primer Group | Primer Name | Sequence 5'3' | SEQ ID NO: |
|---|---|---|---|
| Nef F8235 | Nef F8235 | TAGCTGAGGGGACAGATAG | 49 |
|  | Nef F8235.1 | TAGCTGAGGGaACAGATAG | 50 |
| Nef F8343 | Nef F8343 | ATGGGTGGCAAGTGGTCAAAAAG | 51 |
|  | Nef F8343.1 | ATGGGTGGCAAGTGGTCAAAAcG | 52 |
|  | Nef F8343.2 | ATGGGTGGCAAaTGGTCAAAAAG | 53 |
|  | Nef F8343.3 | ATGGGTGGCAAGTGGTCAAAAgG | 54 |
| Nef R9069 | Nef R9069 | CCAGTACAGGCAAAAAGC | 55 |
|  | Nef R9069.1 | CAGTACAGGCgAAAAGC | 56 |
|  | Nef R9069.2 | CAGTACAGGCAAgAAGC | 57 |

Nucleotides in upper case are complementary to predominant sequence within the region of interest. Nucleotides in lower case indicate compensatory point mutations complementary to mutations within target region.

The present inventors have discovered that amplification of Nef sequences is enhanced by the addition of a novel HIV Nef forward primer, Nef F8235.2 (5' TAGCTGgctGGACA-GATAG (SEQ ID NO:58)) to the Nef F8235 primer group shown in Table 5.

Accordingly, in one embodiment, the invention provides a composition comprising the Nef F8235.2 forward primer of SEQ ID NO:58. In another embodiment, the invention provides a Nef forward primer composition comprising SEQ ID NO:49, SEQ ID NO:50 and SEQ ID NO:58. In order to amplify Nef nucleic acids, these Nef forward primers can be combined with the Nef R9069 reverse primers.

Thus, in another aspect, the invention provides a composition comprising:
 a) the Nef F8235 primers of SEQ ID NO:49, SEQ ID NO:50 and SEQ ID NO:58; and
 b) at least one or a combination of the Nef R9069 primers of SEQ ID NO: 55, SEQ ID NO:56 and SEQ ID NO:57.

In another embodiment, the invention provides a method for amplifying an HIV Nef nucleic acid, comprising carrying out a polymerase chain reaction using at the Nef F8235 forward primers of SEQ ID NO:49, SEQ ID NO:50 and SEQ ID NO:58, together with at least one or a combination of Nef R9069 reverse primers selected from the group consisting SEQ ID NO:55, SEQ ID NO:56 and SEQ ID NO:57.

HIV polynucleotides are the template or the source of the template for reverse transcription and/or amplification of the nucleic acids encoding one or more HIV antigens or epitopes. The HIV polynucleotide may be either DNA or RNA. Non-limiting examples of HIV DNAs include HIV integrated provirus DNA, HIV cDNA present in a cell prior to viral integration into the host genome, HIV cDNA made in vitro by reverse transcription, amplified HIV DNA, cloned HIV DNA, etc. HIV DNA can be used directly as a template for amplification according to the methods of the invention. HIV RNA includes, but is not limited to, HIV viral genomes (e.g., viral RNA isolated from viral particles or from host cells during viral replication), HIV primary RNA transcripts, HIV spliced mRNA, IVT RNA, etc.

In a preferred embodiment, HIV genomic RNA is isolated from HIV virions, such as those present in blood or serum. HIV RNA can be reversed transcribed to produce a cDNA, which can then serve as a template for nucleic acid amplification. The open reading frames of env and rev partially overlap in the HIV genome, and in the normal course of HIV expression, the first and second rev exons in the rev-primary RNA transcript are spliced to result in a processed rev mRNA. Because the preferred HIV template is HIV genomic RNA, it is most practical to amplify the first or second exon of Rev, rather than the entire rev gene, which is only completely in-frame after splicing.

In one embodiment, the HIV polynucleotide is from, or is derived from, multiple HIV variants present in an infected individual. In this context, by "derived from" is meant that the nucleic acid is at least partially purified from the virion or cell(s) containing pathogen nucleic acid, or that the nucleic acid is reverse transcribed or amplified from pathogen nucleic acid. By deriving the nucleic acid from multiple HIV variants present in an individual, the amplified nucleic acid and or IVT RNA, or an antigen presenting cell transfected (loaded) with the amplified nucleic acid or IVT RNA, can elicit an immune response to potentially all of the variants of HIV present in an individual. In addition, the DNA can be sequenced in order to identify the variants of HIV present in a sample or a patient.

Methods for isolating integrated HIV DNA, HIV genomic RNA and HIV mRNA from an infected individual are known to those skilled in the art. Preferably the HIV nucleic acid is isolated or derived from a biological sample from an individual infected with HIV who will be treated with a vaccine comprising an mRNA prepared by in vitro transcription of a nucleic acid amplified using the methods of the invention. "Biological sample" as used herein, refers to any biological sample that may contain HIV, HIV-infected cells or HIV nucleic acid, and includes, but is not limited to, blood, plasma, serum, peripheral blood mononuclear cells (PBMC), seminal fluid, vaginal secretions, ocular lens fluid, cerebral spinal fluid, saliva, milk, ascites fluid, synovial fluid, peritoneal fluid, amniotic fluid, tissue, tissue culture and the like.

Preferably, HIV virions containing HIV genomic RNA are isolated from blood or serum. For autologous therapeutic applications, the HIV virions are preferably present at a copy number of at least 15,000/mL of patient serum. The genomic RNA obtained from the virions can be subjected to reverse transcription to produce an HIV cDNA. Methods of isolating HIV virions from infected patients, as well as methods of making cDNA are known to those skilled in the art. Reverse transcription of HIV RNA can be primed using random hexamers or HIV specific oligonucleotide primers. The HIV cDNA can then be used as a template for amplification of HIV sequences.

DNA amplified from a pathogen template or cDNA copy thereof in a first PCR (or other amplification reaction) is referred to as a "primary amplicon". The primary amplicon produced by the methods of the invention can be used in a nucleic acid vaccine without further modifications. Alternatively, the primary amplicon can be inserted into an expression cassette, expression vector or viral vector for use in a nucleic acid vaccine, viral vaccine or for loading into APCs. In a preferred embodiment, the primary DNA amplicon is modified to function as a template for in vitro transcription. Such methods are known to those of skill in the art. The primary and secondary amplicons of the invention and IVT RNA produced therefrom can be used directly as nucleic acid vaccines or transfected into cells (e.g., antigen presenting cells) for use as an immunotherapeutic. Methods for formulating and delivering nucleic acid vaccines to a subject are known to those of skill in the art. See, for example, Scheel et al. Eur. J. Immunol. (2204) 34:537-547; Hoerr et al. (2000) Eur. J. Immunol. 30:1-7; Liu et al. (2002) Vaccine 20:42-48; Riedl et al. (2002) J. Immunol. 168:4951; Riedel et al. (2004) J. Mol. Med. 82:144; U.S. Pat. No. 5,783,567; U.S. Pat. No. 6,603,998; EP0880360; EP1083232. Routes of administration include, but are not limited to, topical delivery, electroporation of the skin, as well as cutaneous, subcutaneous, intradermal, mucosal and intramuscular administration and the like. Methods of making antigen presenting cell vaccines/immunotherapeutics are known to those of skill in the art. See, for example, U.S. Pat. No. 5,853,719, WO2006/031870, U.S. Pub. No. 2007/0082400 and WO2006/127150, the contents of which are incorporated by reference.

In a preferred embodiment, the primary amplicon is subjected to a second round of amplification using nested primers containing transcription and translation signals suitable for either expression in vitro and/or expression in vivo. The second amplification reaction is also referred to as secondary amplification, secondary PCR, etc., and produces a secondary amplicon. Preferably, the primary amplicon is subjected to a second round of amplification using a forward nested primer containing a promoter suitable for in vitro transcription (such as the T7 or SP6 promoter) and an optimized Kozak sequence including an ATG codon; in combination with a reverse nested primer containing a complement of a translational stop codon and a polyT tail. The secondary amplicon resulting from the nested round of amplification can be used as a template for in vitro transcription to produce IVT RNA. Preferably, the IVT RNA is capped and further polyadenlyated. The resulting capped and polyadenylated mRNA can then be used in a nucleic acid vaccine, or to load antigen presenting cells, which can then be used as a vaccine (cellular immunotherapeutic).

Methods for capping and polyadenylating RNA are known to those of skill in the art. For example, the mRNA can be cotranscriptionally capped in the presence of $m^7G$ cap or an analogue thereof, such as ARCA (see U.S. 2003/0194759) or post-transcriptionally capped. In preferred embodiments, the mRNA is polyadenylated. In one embodiment, polyA tails are added by amplification with a reverse primer containing a 5' polyT tract. Subsequent transcription (in vitro or in vivo) results in an mRNA containing a polyA tails. Alternatively, or in addition, polyA can be added post transcription by a polyadenylation reaction. Preferred polyA tail lengths are in the range of 50-1000 nucleotides, more preferably 64-900 nucleotides, and most preferably 101-600 nucleotides.

In one non-limiting example, HIV RNA isolated from virions is reverse transcribed into single-stranded cDNA using a reverse transcriptase, appropriate reaction buffers, and random hexamers. The single-stranded cDNA is then amplified to produce a double-stranded DNA (primary amplicon) in a primary PCR reaction using multiplex primers. The primary amplicon product from this primary PCR reaction is then used as a template for a secondary PCR with nested primers to produce a secondary amplicon. In this secondary round of amplification, the forward primer(s) preferably contain a 5' overhang comprising T7 RNA polymerase binding sequences, while the reverse primer(s) preferably contains a 5' overhang with poly T stretches. ("Overhang" refers to 5' regions of the secondary primers that do not hybridize with the primary amplicon.) The modifications introduced by overhanging regions in a nested round of PCR enable transcription of the PCR product in vitro and successful translation upon delivery of the IVT RNA into cells (e.g., antigen presenting cells, such as dendritic cells). The process can be interrupted after either step of PCR amplification and PCR products can be stored (preferably frozen) for further processing. Purification of cDNA material (e.g., initial cDNA produced by reverse transcription, primary and secondary amplicons) can be performed using the QIAquick® PCR Purification Kit components (QIAquick® Columns, PB buffer, PE buffer, and EB buffer). The secondary amplicon, a double-stranded DNA, can be used as a template in an in vitro transcription reaction. Preferably, the IVT RNA is capped and polyadenylated. The capping can be performed cotranscriptionally or post-transcriptionally. Clean-up of the in vitro-transcribed RNA can be performed using components in the RNeasy® Kit (RNeasy® Column, RLT buffer, and RPE buffer). The RNA is eluted in nuclease-free water. (If desired, the RNA can be concentrated by ethanol precipitation and re-suspended in nuclease-free water.) The IVT RNA is preferably passed through a 0.8/0.2 μm polyethersulfone (PES) filter, dispensed into 0.5 mL safe-lock polypropylene tubes, and cryopreserved at −150° C. for long-term storage.

Capped and polyadenylated HIV IVT RNAs made using the primers and methods of the invention can be transfected into dendritic cells or other antigen presenting cells, either in vitro or in situ. Such in vitro transfected antigen presenting cells can then be used as a vaccine. Alternatively, capped and polyadenylated RNA can be translated in vitro to produce proteins that can be loaded into antigen presenting cells in vitro, or used directly in a vaccine. Thus, in another embodiment, the invention provides a method of loading an antigen presenting cell, comprising contacting an antigen presenting cell with an RNA produced by the method of the invention.

The antigen presenting cells can be made by and in the mammalian subject, or can be derived from cells isolated from the mammalian subject. In a preferred embodiment, the antigen presenting cell is a dendritic cell. The term "dendritic cells (DC)" refers to a diverse population of morphologically similar cell types found in a variety of lymphoid and non-lymphoid tissues (Steinman (1991) Ann. Rev. Immunol. 9:271-296) or derived from dendritic cell precursors in vitro. Dendritic cells are the most potent of the APCs, and provide the signals necessary for T cell activation and proliferation. Dendritic cells can be derived from bone marrow progenitor cells, circulate in small numbers in the peripheral blood and appear either as immature Langerhans' cells or terminally differentiated mature cells. Preferably, dendritic cells are differentiated from monocytes. Methods for the isolation of antigen presenting cells (APCs), and for producing dendritic cell precursors and mature dendritic cells are known to those skilled. See, for example, Berger et al. J. Immunol. Methods 2002 268:131-140, U.S. Patent Applications 20030199673, 20020164346 and 60/522,512, and WO 93/20185. In a some embodiments, dendritic cells are prepared from CD14+ peripheral blood monocytic cells (PBMCs) by methods described in Romani et al. (J. Exp. Med. 1994 180:83-93), Sallusto et al. (J. Exp. Med. 1994 179:1109-1118), WO2006/031870, U.S. Pub. No. 2007/0082400 and WO2006/127150, the contents of which are incorporated by reference. Alternatively, dendritic cells can be prepared from CD34+ cells by the method of Caux et al. (J. Exp. Med. 1996 184:695-706).

Methods for loading antigen presenting cells are known to those of skill in the art, and include, but are not limited to, electroporation, passive uptake, lipofection, cationic reagents, viral transduction, $CaPO_4$ and the like. See, for example, PCT/US05/22705 and U.S. Ser. No. 60/583,579; U.S. Pub. No. 2007/0082400; 2003/0143743; U.S. Pub. No. 2005/0008622; U.S. Pub. No. 2004/0235175; and U.S. Pub. No. 20040214333. In preferred embodiments, the antigen presenting cells are loaded with both CD40L mRNA and RNA encoding multiple strains of HIV polypeptides.

In a further embodiment, antigen presenting cells are loaded with polypeptides made by in vitro translation of the RNAs encoding pathogen polypeptides from multiple strains of a pathogen. The pathogen polypeptides may be loaded into antigen presenting cells with CD40L mRNA. Dendritic cells can be loaded in vitro when mature or immature. Loaded immature dendritic cells can be matured in vitro prior to vaccination or in vivo (with or without an exogenous maturation stimulus) following vaccination. Alternatively, nucleic acids can be delivered to antigen presenting cells in situ. See, for example Liu et al. (Vaccine 2002 20:42-48), Lisziewics et al. (Vaccine 2003 21:620-623), O'Hagen (Curr Drug Targets Infect Disord 2001 1:273-286) and U.S. Pat. No. 7,015,204.

Preferably, the antigen presenting cell in the above composition is a dendritic cell. The loaded dendritic cell can then be used as a vaccine to treat the pathogen infection in a patient. Preferably, the pathogen and antigen presenting cell (e.g., dendritic cell) are autologous to the treated patient.

Methods of isolating, preparing, transfecting, formulating and administering antigen presenting cells to patients is known in the art. See, for example, Fay et al. Blood 2000 96:3487; Fong et al. J. Immunol. 2001b 166:4254-4259; Ribas et al. Proc Am Soc Clin One 2001 20:1069; Schuler-Thurner et al. J. Exp. Med. 2002 195:1279-88. Erratum in: J. Exp. Med. 2003 197:395; and Stift et al. J. Clin. Oncol 2003 21: 135-142.

The following examples are intended to illustrate, rather than to limit, the invention. It also is to be understood, although not always explicitly stated, that the reagents described herein are merely exemplary and that equivalents of such are known in the art.

EXAMPLES

Methods

Isolation of HIV RNA from Patient Plasma Samples

HIV viral RNA was isolated from 1 to 3 mL of archived frozen plasma of HIV patients using a NucliSens™ kit (BioMerieux), according to the manufacturer's instructions. (Plasma samples were kindly provided by Dr. Rafick Pierre-Sekaly).

Formulation of HIV Primer Groups

Each individual primer was HPLC-purified and reconstituted at a concentration of 100 mM. The Rev primer groups were formulated as follows, using the indicated volume of 100 mM primer stock:

| REV R8300 RT primer group for reverse transcription (20 μM) | |
|---|---|
| Rev R8300 | 13.3 ul |
| Rev R8300.1 | 13.3 ul |

| -continued | |
|---|---|
| Rev R8300.2 | 13.3 ul |
| MilliQ Water | 160 ul |
| REV F7750 primer group (5 µM) | |
| Rev F7750 | 5 ul |
| Rev F7750.1 | 5 ul |
| MilliQ Water | 190 ul |
| REV F7830 primer group (5 µM) | |
| Rev F7830 | 3.33 ul |
| Rev F7830.1 | 3.33 ul |
| Rev F7830.2 | 3.33 ul |
| MilliQ Water | 190 ul |
| REV F7911 primer group (5 µM) | |
| Rev F7911 | 5 ul |
| Rev F7911.1 | 5 ul |
| MilliQ Water | 190 ul |
| REV R8300 primer group (5 µM) | |
| Rev R8300 | 3.33 ul |
| Rev R8300.1 | 3.33 ul |
| Rev R8300.2 | 3.33 ul |
| MilliQ Water | 190 ul |
| REV T7 F7912 primer group (5 µM) | |
| Rev T7 F7912 | 5 ul |
| Rev T7 F7912.1 | 5 ul |
| MilliQ Water | 190 ul |
| HiT7 REV F7912 primer group (5 µM) | |
| Rev T7 F7912.15 | 1.67 ul |
| Rev T7 F7912.16 | 1.67 ul |
| Rev T7 F7912.17 | 1.67 ul |
| Rev T7 F7912.18 | 1.67 ul |
| Rev T7 F7912.19 | 1.67 ul |
| Rev T7 F7912.20 | 1.67 ul |
| MilliQ Water | 190 ul |
| REV R8300 64T primer group (5 µM) | |
| Rev R8300 64T | 3.33 ul |
| Rev R8300.1 64T | 3.33 ul |
| Rev R8300.2 64T | 3.33 ul |
| MilliQ Water | 190 ul |

The Gag primer groups were formulated as follows, using the indicated volume of 100 mM primer stock:

| Anchored Oligo dT$_{(20)}$ for reverse transcription (50 µM) | |
|---|---|
| 370 um dT$_{(20)}$ stock | 13.52 ul |
| MilliQ Water | 86.48 ul |
| GAG R1913 primer group for Reverse Transcription (5 µM) | |
| Gag R1913 | 8.0 ul |
| Gag R1913.1 | 8.0 ul |
| Gag R1913.2 | 8.0 ul |
| Gag R1913.4 | 8.0 ul |
| Gag R1913.5 | 8.0 ul |
| MilliQ Water | 160 ul |
| GAG F124 (5 µM) | |
| Gag F124 | 10 ul |
| MilliQ Water | 190 ul |
| GAG F304 (5 µM) | |
| Gag F304 | 10 ul |
| MilliQ Water | 190 ul |
| GAG F334 primer group (5 µM) | |
| Gag F334 | 5 ul |
| Gag F334.1 | 5 ul |
| MilliQ Water | 190 ul |
| GAG R1881 primer group (5 µM) | |
| Gag R1881 | 3.33 ul |
| Gag R1881.1 | 3.33 ul |
| Gag R1881.2 | 3.33 ul |
| MilliQ Water | 190 ul |
| GAG R1884 primer group (5 µM) | |
| Gag R1884 | 2.5 ul |
| Gag R1884.1 | 2.5 ul |
| Gag R1884.2 | 2.5 ul |
| Gag R1913.3 | 2.5 ul |
| MilliQ Water | 190 ul |
| GAG R1913 primer group (5 µM) | |
| Gag R1913 | 2.0 ul |
| Gag R1913.1 | 2.0 ul |
| Gag R1913.2 | 2.0 ul |
| Gag R1913.4 | 2.0 ul |
| Gag R1913.5 | 2.0 ul |
| MilliQ Water | 190 ul |
| GAG F T7 primer group (5 µM) | |
| Gag T7 F334 | 5 ul |
| Gag T7 F334.1 | 5 ul |
| MilliQ Water | 190 ul |
| HiT7 GAG F primer group (5 µM) | |
| HiT7 Gag F334 | 5 ul |
| HiT7 Gag F334.1 | 5 ul |
| MilliQ Water | 190 ul |
| GAG R1881 64T (5 µM) | |
| Gag R1881 64T | 3.33 ul |
| Gag R1881.1 64T | 3.33 ul |
| Gag R1881.2 64T | 3.33 ul |
| MilliQ Water | 190 ul |

The Nef primers were formulated as follows:

| Anchored Oligo dT$_{(20)}$ for reverse transcription (50 µM) | |
|---|---|
| 370 um dT$_{(20)}$ stock | 13.52 ul |
| MilliQ Water | 86.48 ul |
| NEF F8235 primer group | |
| Nef F8235 | 3.33 ul |
| Nef F8235.1 | 3.33 ul |
| Nef F8235.2 | 3.33 ul |
| MilliQ Water | 190 ul |
| NEF F8343 primer group | |
| Nef F8343 | 2.5 ul |
| Nef F8343.1 | 2.5 ul |
| Nef F8343.2 | 2.5 ul |
| Nef F8343.3 | 2.5 ul |
| MilliQ Water | 190 ul |
| NEF R9069 primer group | |
| Nef R9069 | 3.33 ul |
| Nef R9069.1 | 3.33 ul |
| Nef R9069.2 | 3.33 ul |
| MilliQ Water | 190 ul |
| NEF T7 8343 primer group | |
| Nef T7 8343 | 5 ul |
| Nef T7 8343.1 | 5 ul |
| MilliQ Water | 190 ul |
| NEF R9069 64T primer group | |
| Nef R9069 64T | 3.33 ul |
| Nef R9069.1 64T | 3.33 ul |
| Nef R9069.2 64T | 3.33 ul |
| MilliQ Water | 190 ul |

Reverse Transcription

HIV viral RNA isolated from the plasma of HIV patients was used as a template for reverse transcription. The GAG R1913 primer group (SEQ ID Nos: 37-41) was used for reverse transcription of Gag RNA. (However, in one embodiment (data not shown), an Oligo $dT_{(20)}$ primer was used for reverse transcription of HIV RNA to produce a Gag cDNA, wherein the oligo dT primer hybridizes to an internal polyA sequence downstream of Gag.) The REV 8300 RT primer group (SEQ ID Nos:9-11) were used for reverse transcription of Rev RNA. An Oligo $dT_{(20)}$ primer was used for reverse transcription of Nef RNA. Each 20 μL reverse transcription reaction contained ≦10 μL Patient RNA, 1 μL of 20 μM reverse primers or oligo $dT_{(20)}$, 1 μL dNTPs (10 mM each), and water to bring the total volume to 12 μL. The RNA/primer mix was incubated at 65° C. for 5 minutes, briefly centrifuged, and then placed on ice at least 1 minute. 8 μL of a 1st stand synthesis reaction mix (containing 4 μL, 5×1st strand buffer (Invitrogen Superscript III), 1 μL 100 mM DTT, 1 μL RNaseout (40 U/μL, Invitrogen) and 2 μL Superscript III (200 U/μL, Invitrogen) was added to the RNA/primer mix, the reaction was mixed, briefly centrifuged and incubated at 55° C. for 60 minutes then 70° C. for 15 minutes, and then briefly centrifuged.

HIV Primary PCR Amplifications to Produce Primary Amplicons

Rev primary PCR reactions contained 5 μL PFU 10× buffer (Stratagene), 0.4 μL 100 mM dNTPs, 2 μL PFU Ultra Hotstart™ polymerase (2.5 U/μL, Stratagene), 1 μL of a Rev primary forward primer group (e.g., Rev F7750, Rev F7830 or Rev F7911), 1 μL of the Rev R8300 reverse primer group, 2.5 μL of the cDNA template produced by reverse transcription, and 38.1 μL MilliQ water. This PCR reaction was vortexed, quickly centrifuged, denatured at 95° C. for 2 minutes, and then subjected to 40 cycles of 95° C. for 30 seconds, 54° C. for 30 seconds, 72° C. for 2 minutes. After 40 PCR cycles, the reaction was allowed to elongate at 72° C. for 10 minutes and then stored at 4° C. until further use.

Gag primary PCR reactions contained 5 μL PFU 10× buffer (Stratagene), 0.4 μL 100 mM dNTPs, 2 μL PFU Ultra Hotstart™ polymerase (2.5 U/μL, Stratagene), 2 μL of a Gag primary forward primer group (e.g., Gag F124, Gag F304 or Gag F334), 1 μL of a Gag reverse primer group (e.g., Gag R1881, Gag R1883 or Gag R1884), 2.5 μL of the cDNA template produced by reverse transcription, and 36.1 μL MilliQ water. This PCR reaction was vortexed, quickly centrifuged, denatured at 95° C. for 2 minutes, and then subjected to 40 cycles of 95° C. for 30 seconds, 54° C. for 30 seconds, 72° C. for 2 minutes. After 40 PCR cycles, the reaction was allowed to elongate at 72° C. for 10 minutes and then stored at 4° C. until further use.

Nef primary PCR reactions contained 5 μL PFU 10× buffer (Stratagene), 0.4 μL 100 mM dNTPs, 2 μL PFU Ultra Hotstart™ polymerase (2.5 U/μL, Stratagene), 4 μL of a Nef primary forward primer group (e.g., Nef F8235 or Nef F8343), 4 μL of the Nef R9069 reverse primer group, 2.5 μL of the cDNA template produced by reverse transcription, and 32.1 μL MilliQ water. This PCR reaction was vortexed, quickly centrifuged, denatured at 95° C. for 2 minutes, and then subjected to 40 cycles of 95° C. for 30 seconds, 54° C. for 30 seconds, 72° C. for 2 minutes. After 40 PCR cycles, the reaction was allowed to elongate at 72° C. for 10 minutes and then stored at 4° C. until further use.

HIV Secondary PCR Reactions

Rev secondary PCR reactions contained 2.5 μL PFU 10× buffer (Stratagene), 0.2 μL 100 mM dNTPs, 1 μL PFU Ultra Hotstart™ polymerase (2.5 U/μL, Stratagene), 0.75 μL of a 5 μM Rev T7 primer group (e.g., Rev T7 7912, Rev T7 7912 9-overlap or Rev T7 7912 16-overlap), 0.75 μL of 5 μM Rev R8300 64T reverse primer group, 1 μL of a 1:10 dilution of the Rev cDNA amplicon produced by primary PCR, and 18.8 μL MilliQ water for a total volume of 25 μL. This PCR reaction was vortexed, quickly centrifuged, denatured at 95° C. for 2 minutes, and then subjected to 40 cycles of 95° C. for 30 seconds, 54° C. for 30 seconds, 72° C. for 2 minutes. After 40 PCR cycles, the reaction was allowed to elongate at 72° C. for 10 minutes and then stored at 4° C. until further use.

Gag secondary PCR reactions contained 2.5 μL PFU 10× buffer (Stratagene), 0.2 μL 100 mM dNTPs, 1 μL PFU Ultra Hotstart™ polymerase (2.5 U/μL, Stratagene), 0.5 μL of 5 μM Gag T7 F334 primer group, 0.5 μL of 5 μM Gag R1881 64T reverse primer group, 1 μL of a 1:10 dilution of the Gag cDNA amplicon produced by primary PCR, and 19.3 μL MilliQ water for a total volume of 25 μL. This PCR reaction was vortexed, quickly centrifuged, denatured at 95° C. for 2 minutes, and then subjected to 40 cycles of 95° C. for 30 seconds, 54° C. for 30 seconds, 72° C. for 2 minutes. After 40 PCR cycles, the reaction was allowed to elongate at 72° C. for 10 minutes and then stored at 4° C. until further use.

Nef secondary PCR reactions contained 2.5 μL PFU 10× buffer (Stratagene), 0.2 μL 100 mM dNTPs, 1 μL PFU Ultra Hotstart™ polymerase (2.5 U/μL, Stratagene), 1 μL 0.5 μM Nef T7 8343 primer group, 1 μL 0.5 μM Nef 9069 64T reverse primer group, 1 μL of a 1:10 dilution of the Rev cDNA amplicon produced by primary PCR, and 18.3 μL MilliQ water for a total volume of 25 μL. This PCR reaction was vortexed, quickly centrifuged, denatured at 95° C. for 2 minutes, and then subjected to 40 cycles of 95° C. for 30 seconds, 54° C. for 30 seconds, 72° C. for 2 minutes. After 40 PCR cycles, the reaction was allowed to elongate at 72° C. for 10 minutes and then stored at 4° C. until further use.

Preparative secondary PCR reactions were performed as above, except scaled up linearly to 100 μL reactions per 1.5 mL tube.

Cloning and Sequencing

Rev and Nef cDNA fragments were cloned into vector pCR®4Blunt-TOPO® from Invitrogen according to the manufacturer's recommended Protocol. 500 ng of cDNA fragment was used in 6 μL of ligation reaction. 2 μL of the ligation reaction was transformed into 100 μL of DH5α competent cells (Invitrogen), and plated out on LB-Amp$^r$ plates. Ten colonies were inoculated into 5 mL liquid LB cultures and incubated overnight at 37° C. with agitation. Plasmid DNA was isolated using Qiagen mini prep columns (Qiaprep Spin Miniprep kit, Qiagen). The samples were sequenced using M13Forward primer or M13Reverse primer. The sequencing results were analyzed using DNAstar software.

In Vitro Transcription of HIV Antigens

Secondary PCR fragments modified with T7 primer and oligo dT sequences encoding the HIV antigen of choice served as templates for an in vitro transcription reaction using mMessage mMachine™ T7 Ultra kits and ARCA Kits. (Ambion). The transcription reactions were carried out according to the manufacturer's instructions, as described above. For large scale reactions, 25 μg cDNA template, 60 μL 10× reaction buffer, 300 μL 2×NTP/ARCA, 60 μL T7 polymerase and water to bring the total volume to 600 μL were mixed in a 1.5 mL tube and incubated in 1.5 mL tubes at 37° C. in a heat block for 5 hours. The cDNA template was then digested by adding 25 μL Turbo DNase and incubating at 37° C. for 30 minutes. The IVT RNA was purified over one RNeasy® Midi column (QIAGEN) and eluted in RNAse-free water according to the manufacturer's directions. The purified RNA was stored in liquid nitrogen as single-use aliquots until use.

In Vitro Translation in vitro translation of IVT RNAs was carried out using wheat germ extract (Wheat Germ Extract, Promega Cat# L4380) or Rabbit Reticulocyte lysate (Rabbit Reticulocyte Lysate System, Nuclease Treated, Promega Cat# L4960) and $^{35}$S-methionine. Briefly, 1 µg of RNA template was added to a total of 25 µL reaction volume. Translation reaction using wheat germ extract was incubated at 25° C. for 2 hours; translation reaction using reticulocyte lysate was incubated at 30° C. for 90 minutes. 3 µL of the translation reaction were mixed with sample buffer resolved by onto an 18% Tris-HCl denaturing polyacrylamide gel (BioRad Cat#345-0023). Proteins were separated by electrophoresis at 220 volts for 55 minutes and then transferred to a PVDF membrane. The membrane was exposed to a phosphoimager screen at room temperature for 60 minutes, and the screen was scanned using the Storm imager.

Isolation of Human Dendritic Cells

A leukapheresis sample from a healthy volunteer was collected on a COBE Spectra (Gambro BCT) using the AutoPBSC procedure described by Lifeblood (Memphis, Tenn.). Peripheral blood mononuclear cells were isolated using a Ficoll density gradient (Histopaque®-1007 Hybri-Max®, Sigma) and cultured for 1 to 2 hours to allow adherence of the monocytes. Non-adherent cells were removed and the remaining monocytes were cultured in X-VIVO 15™ (Cambrex) medium for 6 to 7 days, supplemented with 1000 U/mL each of GM-CSF (Berlex, Leukine® liquid) and IL-4 (R&D Systems). Immature DCs were electroporated with 2-5 µg of RNA per million cells. Electroporated DC were cultured overnight in X-VIVO™ 15 with 800 U/mL GM-CSF, 500 U/mL IL-4, and a maturation cocktail consisting of IL-1β, TNF-α, IL-6, and PGE$_2$.

Generation of DC for Functional Testing of HIV IVT RNAs for the Induction of Anti-HIV Immunity In Vitro Immature DCs were generated as described above from a leukapheresis product harvested from a successfully HAART-treated HIV donor with a viral plasma copy number of less than 200 copies per mL. To achieve DC maturation, immature DC were first cultured on day 5 with 10 ng/ml TNF-α, 1000 µg/ml IFN-γ, 1 µg/ml PGE$_2$. On Day 6, phenotypically mature DC were co-electroporated with RNA encoding CD40L (1 µg per million of DC), and HIV RNAs generated from a near full length non infectious clones pBKBH10S and p93TH253.3 or from RNA amplified from patient samples at 1 ug Gag, Rev, Vpr and 0.25 µg Nef per million DC. A negative control DC stimulator was generated in parallel by transfecting DC with CD40L RNA and 3.25 µg eGFP RNA, instead of HIV RNA mix. RNA-electroporated DC were further cultured for 4 hrs in X-VIVO-15 medium without additional cytokine supplements.

Western Blot Analysis

Total protein was extracted using M-PER mammalian protein extraction reagent (Pierce Cat#78503) according to the manufacturer's recommended Protocol. Protein concentration was determined by Bradford assay (Bio-Rad Cat#500-0006). Briefly, 40 µg of total protein extract was separated by SDS gel electrophoresis and transferred to PVDF membrane. The membrane was probed by mouse monoclonal Rev antibody (1:500 dilution in blocking buffer) from Fitzgerald (Clone# M612936; immunogen HIV REV amino acids 33-48) and the signal was developed using ECL Plus reagents (Amersham Cat# RPN2132) and scanned by Storm imager.

In Vitro Co-Culture of DC and PBMC from an HIV-Infected Subject to Induce Anti-HIV T-Cell Responses to Multiple HIV Antigens CFSE labeling: PBMCs from the HIV donor were enriched by Ficoll gradient separation, washed twice with PBS and re-suspended at $2.0 \times 10^7$/ml in PBS. CFSE was added to the cell suspension for a final working concentration of 1.0 µM. Cells were incubated for 8 minutes at room temperature with gentle mixing. The staining was quenched by the addition of an equal volume of Human AB Serum and incubation for 2 minutes.

Initial DC/PBMC co-culture: Cultures of HIV RNA-electroporated mature DC, and eGFP-RNA control DC were established in parallel with CFSE-labeled PBMC at a 1:10 ratio, 1 million total cells/mL in 5% Human AB serum for 6 days at 37° C., 5% CO$_2$.

Cell surface phenotyping of proliferating CFSE 'low' labeled cells: After 6 days of culture, PBMCs were harvested, washed once with 2 mL PBS containing 10% FBS and stained for surface antigens using CD45RA PE, CD8 PerCP-Cy5.5, CD28 APC or CD45RA PE, CD4 PerCP-Cy5.5, CD28 APC antibodies (BD Bioscience) at room temperature in the dark for 20 minutes. Samples were washed twice with cold PBS containing 10% FBS and re-suspended in 300 µL of 2% BD Cytofix (BD Bioscience) Samples were acquired on a BD FACSCalibur flow cytometer and analyzed using FlowJo software (Three Star, Inc.) Analysis gates were set on the basis of FSC v. SSC to define viable lymphocytes and lymphoblasts, and the frequency of proliferating cells determined by detection of CFSE 'low' cells, and their associated cell surface phenotype Measurement of anti-HIV specific activity by restimulation of PBMCs with individual DC populations expressing a single HIV genemmature DC were generated as described above, matured with TNF-α, IFN-γ and PGE$_2$ and cells split into 5 groups, allowing for DC populations to be generated expressing just a single HIV gene from the panel of four individual antigens, and a fifth DC population electroporated with eGFP RNA, as negative control. The four individual HIV-gene-loaded-DC populations, and the eGFP control, were co-cultured in parallel with CFSE-labeled PBMC harvested from the previous 6-day co-culture described above. One hour after re-stimulation with DCs, 0.25 µl of Golgi plug (BD Bioscience) was added to each sample and incubated for an additional 3 hours at 37° C., 5% CO$_2$ in RPMI containing 10% Human Serum. Samples were washed once with 1 ml PBS containing 10% FBS and stained for surface antigens using CD8 PerCP-Cy5.5 or CD4 PerCP-Cy5.5 antibodies at 4° C. in the dark for 20 minutes. Samples were washed twice with 1 ml cold PBS containing 2% FBS and re-suspended in 150 µl of 2% BD Cytofix and incubated at room temperature in the dark for 20 minutes. Samples were washed twice with 1 ml of Perm/Wash buffer (BD Bioscience) and incubated at room temperature in the dark for 20 minutes with 2 µl of purified Mouse IgG$_1$ antibody. Samples were stained for intra-cellular cytokines using IL-2 PE and IFN-γ APC antibodies at room temperature in the dark for 20 minutes. Samples were washed twice with 1 ml of BD Perm/Wash buffer and re-suspended in 150 µl of 2% BD Cytofix, acquired on a BD FACSCalibur flow cytometer and analyzed using FlowJo software. PBMC that had proliferated (CFSE 'low') during the previous 6-day co-culture were gated and analyzed for induced IFN-γ and IL-2 content.

Example 1

Figures 3, 4:
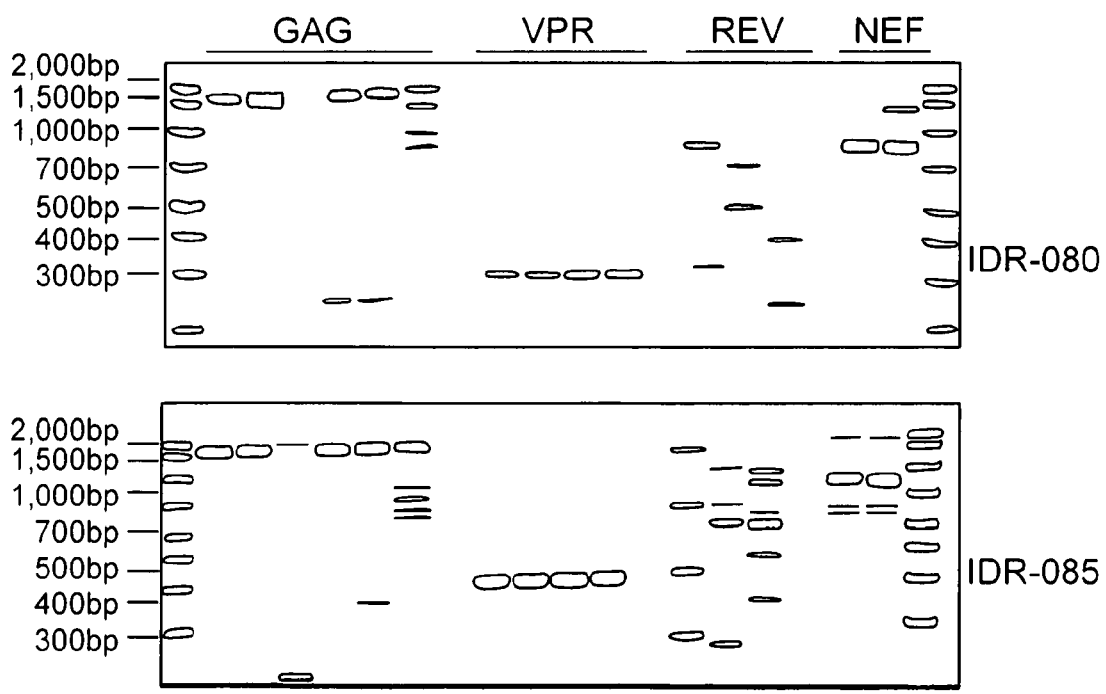
FIG. 3 shows representative results of annealing between primers and HIV genomes performed by PrimAlign module of HIV sequence database (Los Alamos National Laboratory). The alignment was performed using 625 sequences. The representative HIV sequences are shown in this figure that contains predominant point mutations in the target region for Gag R1881, 1883, and 1884 annealing. The QUERY sequence (SEQ ID NO:69) is 5' to 3' in relation to HIV genome. Primer sequences are reverse complements to the sequence shown. Refer to Tables 3 and 4 for primer sequences.
FIG. 4 shows 3% non-denaturing agarose gel resolution of 1 μl of secondary amplicons produced by amplification of two HIV Clade C patient samples, IDR-080 and IDR-085, using primers disclosed in PCT publication WO2006/031870.

Universal Rev T7 Primers for Improved Amplification of HIV Clade B and Non-Clade B Rev Sequences The protocol for amplification of Rev cDNA disclosed in PCT publication WO2006/031870 utilizes three primary PCR reactions followed by a secondary PCR reaction. The three primary PCR reactions combine one of the three Rev forward primer groups (Rev F 7750 primer group, Rev F 7830 primer group or Rev F 7911 primer group) with one reverse primer group (Rev R 8300 primer group). The secondary PCR reaction amplifies an aliquot of the primary PCR reaction utilizing the Rev T7 7912 primer group in combination with the Rev R8300 64 T primer group. However, the present inventors found that secondary amplification of Rev from HIV Clade 3 isolates using the previously designed Rev T7 7912 forward primer group with the Rev R8300 64T primer group did not always produce optimal results. Specifically, analysis of the secondary PCR products separated by 3% non-denaturing agarose gel electrophoresis revealed multiple bands in all three PCR reactions established for Rev (FIG. 4). Rev PCR products have lower purity in comparison to Gag, Vpr and Nef PCR products, and exhibited no single predominant secondary amplicon within the accepted size range for exon 2 of Rev, which is between 433 bp and 586 bp.

Accordingly, new Rev primer groups Rev T7 7912 9-overlap and Rev T7 7912 16-overlap (see Table 2), were designed in order to improve amplification of Clade C and non-Clade B Rev sequences. Amplification of Clade C Rev cDNA using the new T7 overlap primers was compared to the previously disclosed Rev T7 7912 primer group (see Table 1). As a preliminary step, Rev cDNA from patient sample IDR-099 (Clade C) was amplified in three primary PCR reactions that combined one of the three previously designed Rev forward primer groups (Rev F7750, Rev F7830 or Rev F7911 with the previously designed Rev R8300 reverse primer group. In order to test the new Rev T7 primers, the primary amplicons produced by these three PCRs were divided into three secondary amplification reactions using one of three Rev T7 primer groups (Rev T7 7912 9-overlap, Rev T7 7912 16-overlap or Rev T7 7912) in combination with the Rev R8300 64T primer group.

Figure 5:
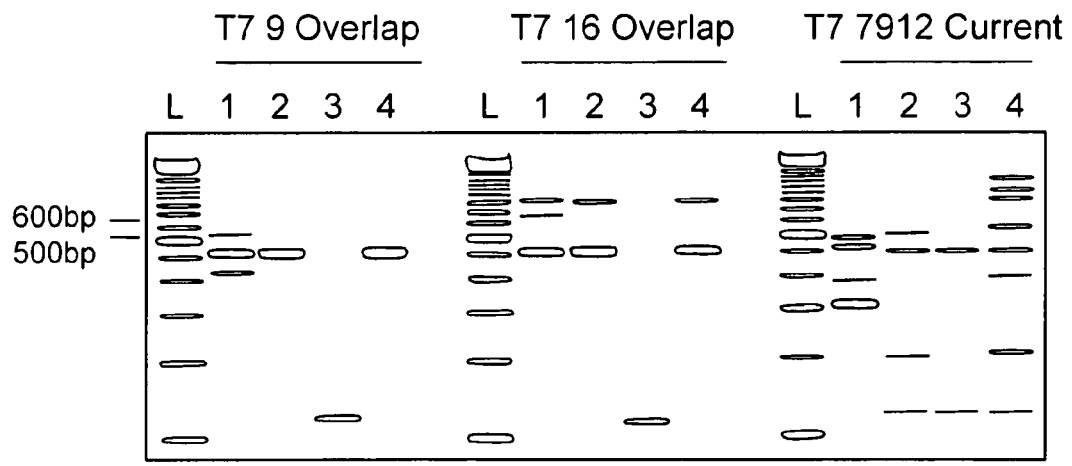
FIG. 5 shows 3% non-denaturing agarose gel resolution of 1 μL of secondary amplicons produced by amplification of HIV Clade C patient IDR-099 Rev viral RNA. The viral RNA was first amplified using RT-PCR with the following combination of primary primers: Lane 1: Rev F7750/Rev R8300; Lane 2: Rev F7830/Rev R8300; Lane 3: Rev F7912-new/Rev R8300; Lane 4: Rev F7911/Rev R8300. Each panel represents the primary PCR reactions listed above amplified using different sets of secondary primer groups: the Rev T7 7912 9-overlap primer group with the Rev R8300 64T primer group; the Rev T7 7912 16-overlap primer group with the Rev R8300 64T primer group; and the Rev T7 7912 from PCT publication WO2006/031870 (labeled as T7 current) with the Rev R8300 64T primer group. L: molecular weight marker, 100 bp DNA ladder (Invitrogen).
Figure 6:
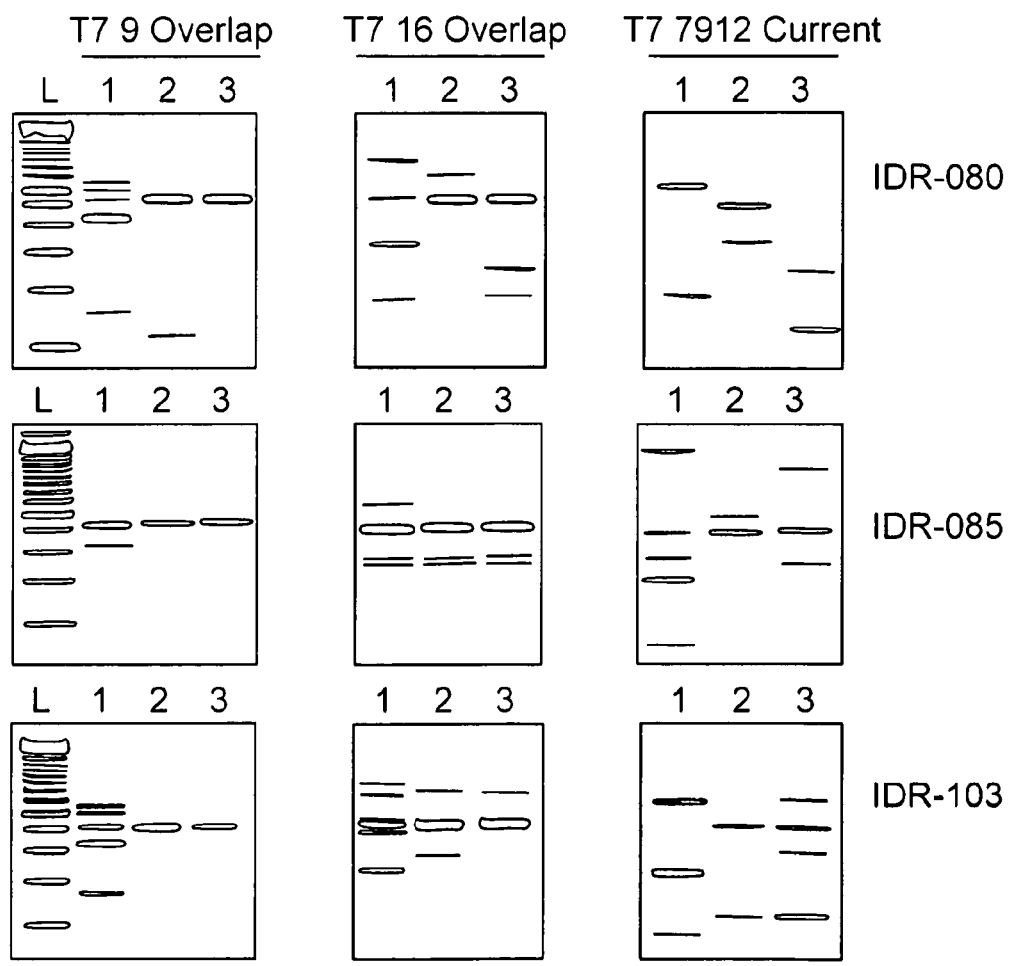
FIG. 6 shows 3% non-denaturing agarose gel resolution of 1 μL secondary PCR products produced by secondary amplification of Rev cDNA amplified from three patient samples IDR-080 (Clade C), IDR-085 (Clade C), and IDR-103 (Clade CRF-06). The viral RNA from each patient was first amplified using RT-PCR with the following combination of primary primers: Lane 1: Rev F7750/Rev R8300; Lane 2: Rev F7830/Rev R8300; Lane 3: Rev F7911/Rev R8300. Each panel represents the primary PCR reactions listed above amplified using different sets of secondary primer groups: the Rev T7 7912 9-overlap primer group with the Rev R8300 64T primer group; the Rev T7 7912 16-overlap primer group with the Rev R8300 64T primer group; and the Rev T7 7912 from PCT publication WO2006/031870 (labeled as T7 current) with the Rev R8300 64T primer group. L: molecular weight marker, 100 bp DNA ladder (Invitrogen).

As shown in FIG. 5, both of the newly designed secondary primer groups (Rev T7 7912 9-overlap or 16-overlap) amplify a specific band which falls within expected molecular weight range (lanes 1, 2, and 4) and produce an amplification pattern superior to the pattern obtained with the previous Rev T7 F7912 primer group. RT-PCR of three additional HIV Clade 3 patients confirmed the superiority of the Rev T7 7912 9-overlap and Rev T7 7912 16-overlap primer groups over the previous Rev T7 primer group (FIG. 6).

To assess the performance of these primers in a large scale cDNA amplification reaction, preparative scale secondary PCR reactions were performed as described above. The PCR products were pooled and purified using QIAquick PCR purification columns. The concentration of each cDNA sample was measured using the BioRad SMART300 spectrophotometer (Table 6). Yields were calculated by multiplying the concentration by the QIAquick column eluate, which is roughly 200 μL. The yields of Rev cDNA amplified with the Rev T7 7912 16-overlap primer group was greater than the yield obtained with the Rev T7 7912 9-overlap primer group in all four Clade C patient samples.

TABLE 6

Yields of Rev secondary amplicons obtained by amplification with various T7 Rev primers in four Clade C subjects

| Clade C Patient Samples/ T7 Primer | Initial Conc. (μg/μL) | Yield (μg) | MW |
| --- | --- | --- | --- |
| IDR-080/Rev T7 9-overlap | 0.220 | 44 | 564 |
| IDR-080/Rev T7 16-overlap | 0.248 | 50 | 571 |
| IDR-085/Rev T7 9-overlap | 0.285 | 57 | 577 |
| IDR-085/Rev T7 16-overlap | 0.340 | 68 | 571 |
| IDR-099/Rev T7 9-overlap | 0.285 | 57 | 577 |
| IDR-099/Rev T7 16-overlap | 0.387 | 77 | 577 |
| IDR-103/Rev T7 9-overlap | 0.123 | 25 | n/a |
| IDR-103/Rev T7 16-overlap | 0.231 | 46 | 558 |

Figure 7:
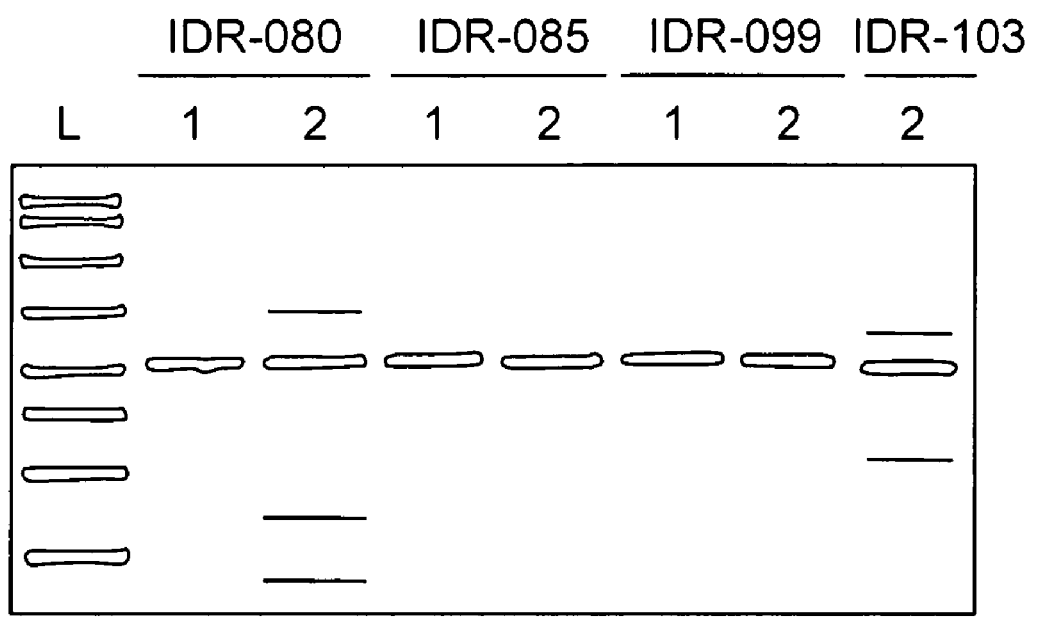
FIG. 7 shows 3% non-denaturing agarose gel resolution of 50 ng of purified Rev secondary amplicons produced on a preparative scale from four non Clade-B HIV subjects IDR-080 (Clade C), IDR-085 (Clade C), IDR-099 (Clade C), and IDR-103 (Clade CRF-06). Within each subject: Lane 1: Rev amplified using the Rev T7 7912 9-overlap primer group with the Rev R8300 64T primer group; Lane 2: Rev amplified using the Rev T7 7912 16-overlap primer group with the Rev R8300 64T primer group. L: molecular weight ladder, AmpliSize Molecular Ruler™ 50-2000 bp (BioRad).

In order to analyze the quality of the secondary Rev amplicons, 50 ng of Rev cDNA (except IDR-103/Rev T7 7912 9-overlap) was resolved by 3% non-denaturing agarose gel electrophoresis (FIG. 7). Molecular weights (MW) of Rev cDNAs were determined by alphaimager autoquery function (Table 6). Based on previous experience with Clade B samples, the expected size of Rev cDNA is typically between 433 and 586 bp. The observed molecular weights of Non-Clade B Rev cDNA fall within this range, but tend to cluster towards the upper end of the range.

Figure 8:
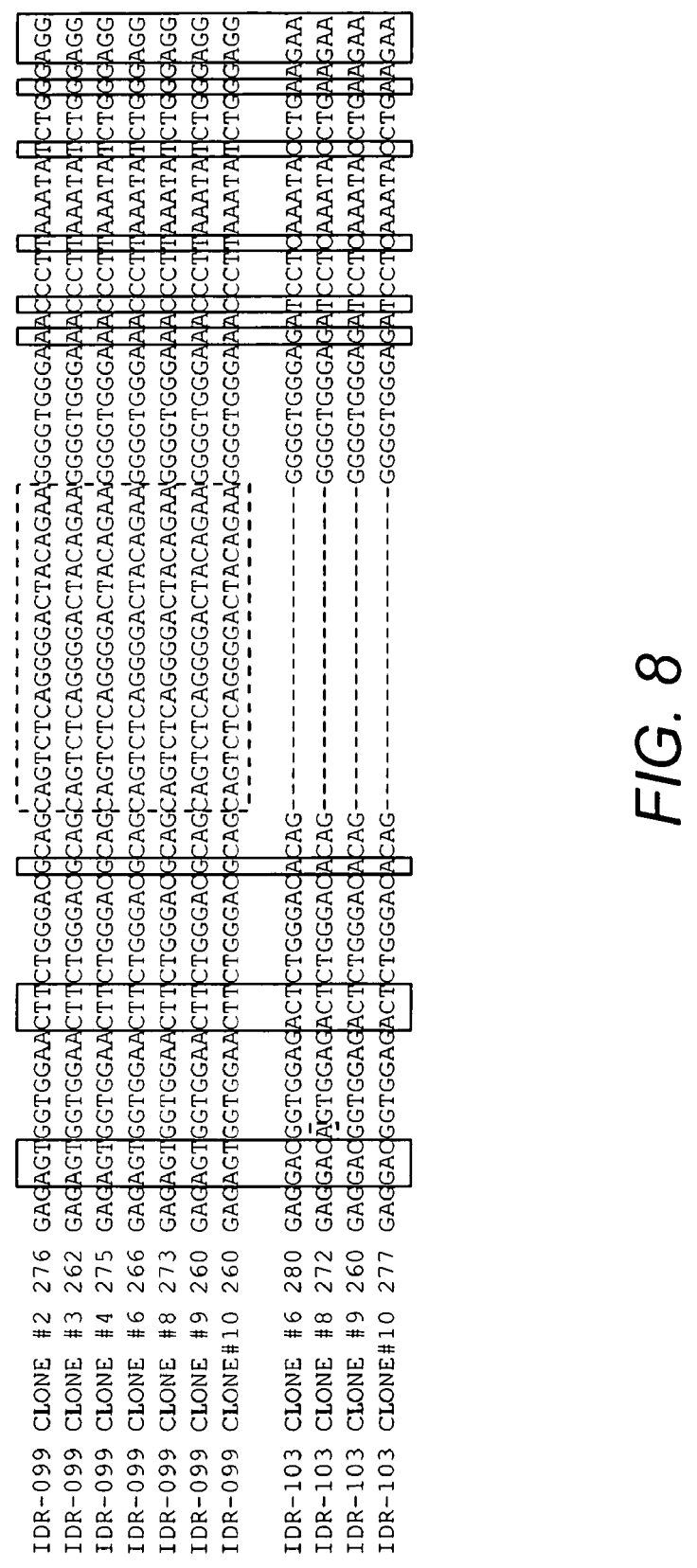

The IDR-103 Rev cDNA migrates slightly faster than Revs cDNAs from other three subjects, which would indicate a smaller molecular weight. According to alphaimager autoquery, there is a 20 nucleotide difference in the cDNA size of IDR-103 and its neighbor IDR-099. It is expected that same antigen cDNA amplified from various subject plasma may migrate differentially due to deletions or insertions in the HIV genome. This was confirmed by cloning the cDNAs from IDR-103 and IDR-099 into pCR®4Blunt-TOPO® (Invitrogen) and sequence analysis using M13 forward and M13 reverse sequencing primers. Seven out of ten colonies picked for IDR-099 contained inserts, and four out of ten colonies picked for IDR-103 contained inserts. The alignment of multiple individual clone sequences obtained for the two samples revealed a 21 nt deletion in IDR-103 Rev cDNA (FIG. 8). This observation is consistent with the difference in molecular weight observed on non-denaturing agarose gel.

The secondary amplicon produced by amplification of the IDR-103 Clade C sample using the Rev T7 7912 9-overlap primer group together with the Rev 8300 64T primer group was dilute, and therefore was concentrated by ethanol precipitation prior to analysis by non-denaturing gel electrophoresis. Gel analysis revealed two bands: a faint band that falls within the expected molecular weight limits and an intense band consisting of a low molecular weight species (primer dimers), evidence of inefficient PCR reactions (data not shown). This sample was not taken into in vitro transcription reaction.

Figure 9:
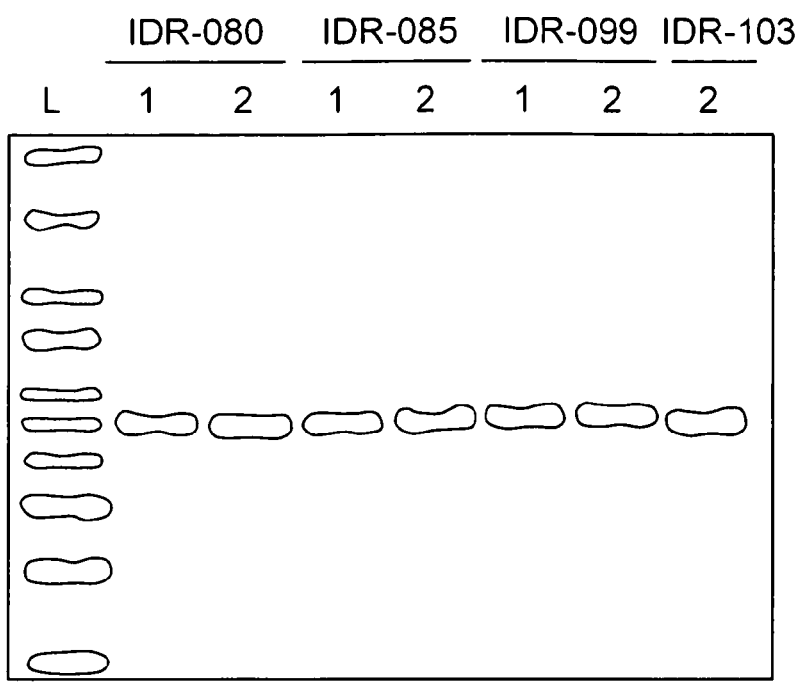
FIG. 9 shows 2% denaturing agarose gel resolution of 500 ng of purified Rev IVT RNA produced from four non-Clade B subjects (IDR-080, IDR-085, IDR-099, and IDR-103). For each subject: Lane 1: Rev amplified using the Rev T7 7912 9-overlap primer group with the Rev 8300 64T primer group; Lane 2: Rev amplified using the Rev T7 7912 16-overlap primer group with the Rev 8300 64T primer group. L: molecular weight ladder, 0.1-2 kb RNA ladder (Invitrogen).

IVT RNA was produced as described above for all cDNA samples except for the IDR-103 sample. The concentration of each IVT RNA sample was measured by spectrophotometry (Table 7). The RNA yields exceeded 400 μg for all samples. Amplification factors are in the range of 33 to 40. The yields of RNA obtained from cDNA amplified using either Rev T7 7912 9-overlap or Rev T7 7912 16-overlap primer groups were comparable. The quality of each IVT RNA sample was analyzed on denaturing gel electrophoresis (FIG. 9). The observed molecular weights of these non-B Rev IVT RNAs fall within the expected range of 407 and 550 bp.

TABLE 7

Rev IVT RNA yields

| Samples | Final Conc. (µg/µL) | Yield (µg) | MW |
|---|---|---|---|
| IDR-080 Rev T7 9 overlap | 1.014 | 837 | 468 |
| IDR-080 Rev T7 16 overlap | 1.044 | 800 | 459 |
| IDR-085 Rev T7 9 overlap | 1.080 | 798 | 468 |
| IDR-085 Rev T7 16 overlap | 1.035 | 824 | 478 |
| IDR-099 Rev T7 9 overlap | 1.069 | 924 | 487 |
| IDR-099 Rev T7 16 overlap | 1.090 | 896 | 487 |
| IDR-103 Rev T7 16 overlap | 1.043 | 841 | 468 |

Figure 10:
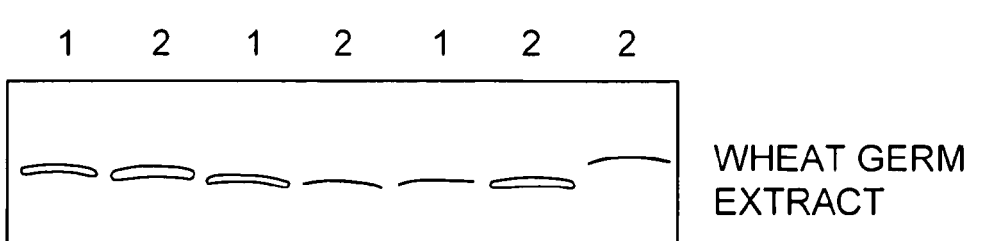
FIG. 10 shows SDS-PAGE resolution of in vitro translation of Rev protein using Rabbit Reticulocyte Lysate or Wheat Germ Extract. The in vitro translation system used is indicated to the left of the panel. Data on four non-B subjects IDR-080, IDR-085, IDR-099, and IDR-103 is shown as indicated at the top of the gel. Within each subject, Lane 1: Rev amplified using the Rev T7 7912 9-overlap primer with the Rev 8300 64T primer group. Lane 2: Rev amplified using Rev T7 7912 16-overlap primer group with the Rev 8300 64T primer group.

The Rev IVT RNAs were translated in vitro using either Rabbit Reticulocyte Lysate or Wheat Germ Extract and labeled with $^{35}$S-methione (FIG. 10). All bands migrated with molecular weight of about 15-16 kDa. The Rev protein produced from patient IDR-103 is slightly larger than Rev proteins from other three subjects. This is was unexpected result because the cDNA obtained for the same sample migrated faster than the cDNAs and RNAs of the other three subjects. Further analysis of sequencing data obtained for IDR-103 and IDR-099 Rev cDNA revealed a C to T mutation introducing a stop codon within the IDR-099 Rev coding sequence. This mutation introduces a premature stop codon, which in turn results in translation of a truncated protein. Sequence analysis and in silico translation of the cDNA predicted the length of IDR-103 Rev protein to be ninety-two amino acids, and IDR-099 Rev is 83 a.a. The difference of nine amino acids is roughly equal to a 1 kDa difference in molecular weight observed using SDS-PAGE analysis.

Figure 11:
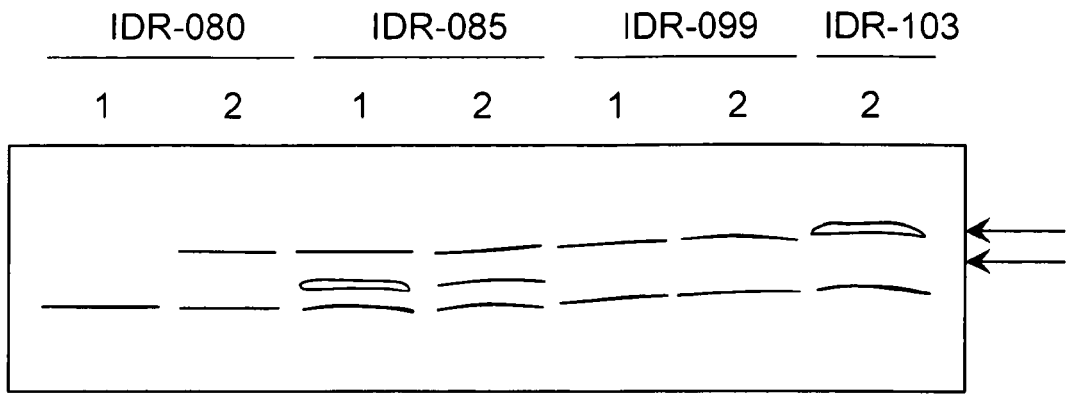
FIG. 11 shows a Western Blot of Rev proteins translated in vitro from IVT RNA produced from four non-Clade B subjects (IDR-080, IDR-085, IDR-099, and IDR-103). Within each subject, Lane 1: Rev amplified using the Rev T7 7912 9-overlap primer group with the Rev 8300 64T primer group. Lane 2: Rev amplified using the Rev T7 7912 16-overlap primer group with the Rev 8300 64T primer group.

The identity of the proteins translated from Rev IVT RNAs was tested in Western blot analysis using an anti-Rev antibody. 10×10$^6$ DC were transfected with 40 µg of Rev IVT RNA. Post-transfection, cells were seeded at 10$^6$ cells/mL in 6-well low adherence plate supplemented with 1000 U/mL of IL4 and 1000 U/mL of GM-CSF. Cells were harvested 4 hours post-transfection. Western blot analysis was performed on the membranes with resolved and transferred whole cell lysates prepared from the transfected DC. Using mouse monoclonal anti-Rev antibody (Mouse anti-HIV Rev mono IgG1 Ab, Fitzgerald) followed by binding of secondary antibody (Goat anti-mouse IgG-HRP, Santa Cruz). As shown in FIG. 11, the mouse monoclonal antibody recognizes a specific band in the lysates transfected with IDR-085 Rev and IDR-103 Rev RNAs. The specific bands migrated with 15 and 16 kDa. The intensity of the signal obtained in the lysate prepared from cells transfected with IDR-085 amplified using Rev T7 7912 16-overlap primer group is lower than that of obtained with Rev T7 7912 9-overlap primer group. This result is consistent with data obtained for this sample in the in vitro translation assay (FIG. 10).

No specific signal was produced in lysates generated from DC transfected with IDR-080 and IDR-099 Rev IVT RNA. The Rev cDNAs for all four samples were subcloned and analyzed by sequencing. Sequencing analysis of the epitope, which corresponds to the epitope used to raise this monoclonal antibody, has an arginine (R) to lysine (K) transition in IDR-080 and IDR-099. The mutation occurs in the middle of the epitope and most likely produces a conformational change within Rev protein, rendering it to be unrecognizable by the antibody (data not shown).

Figure 12:
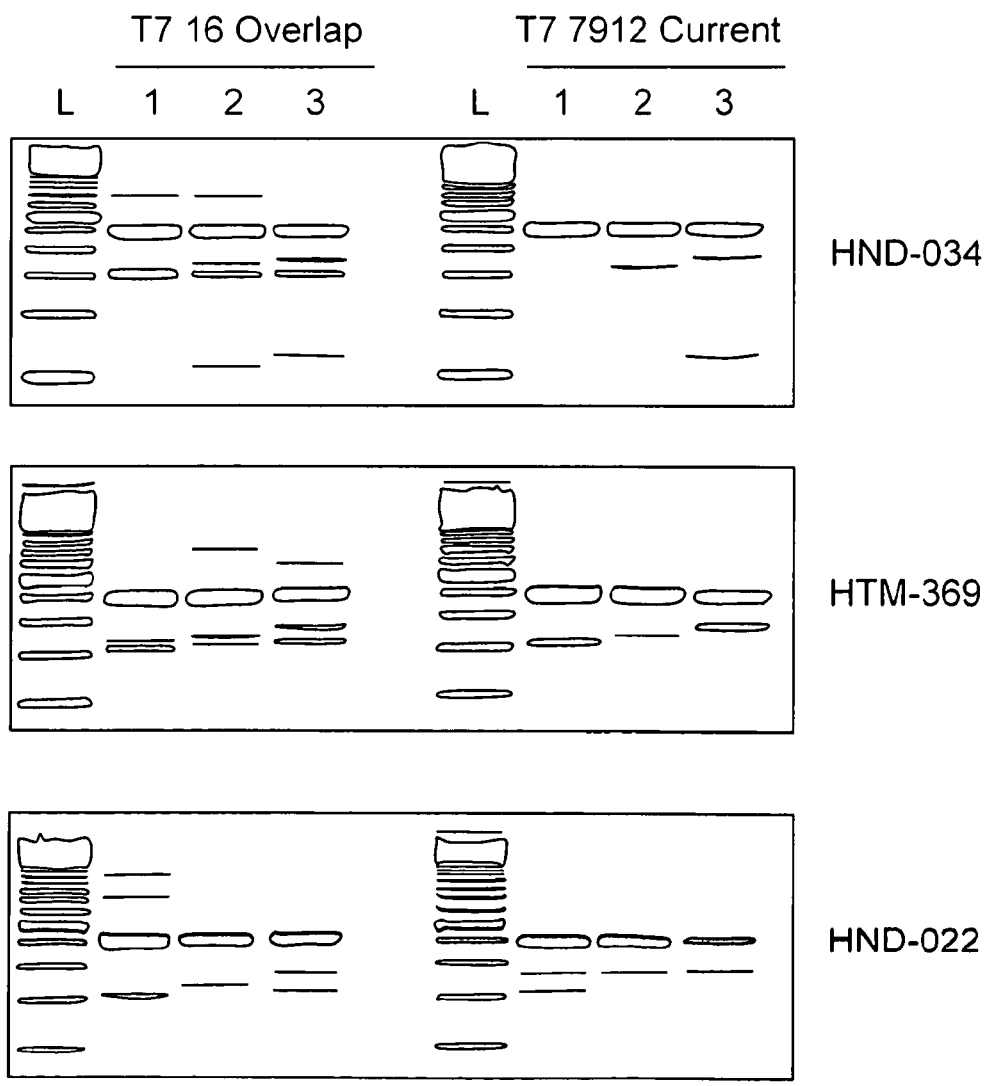
FIG. 12 shows Rev cDNAs and IVT RNAs amplified from three Clade B and Clade AG samples: HND-034 (Clade B), HTM-369 (Clade B) and HND-022 (Clade AG) using the Rev T7 7912 16-overlap primer group with the Rev 8300 64T primer group (left) or the Rev T7 7912 primer group with the Rev 8300 64T primer group. Each lane within the panel was amplified using the following combination of primary primer groups: Lane 1: Rev F7750/Rev R8300; Lane 2: Rev F7830/Rev R8300; Lane 3: Rev F7911/Rev R8300. L: molecular weight marker, 100 bp DNA ladder (Invitrogen).

The Rev T7 16-overlap primer group was designed to accommodate the amplification of non-Clade B sequences. We next verified that the new Rev T7 16-overlap primer group can also effectively amplify Clade B sequences. Three Clade B samples that had previously been successfully amplified using the Rev primers disclosed in Table 1 were tested with the Rev T7-overlap primer group. As shown in FIG. 12, the Rev T7 16-overlap primers amplified Clade B samples from all three patients as well or better than the Rev T7 7912 primers.

cDNA and IVT RNA were prepared from these three samples at a preparative scale. The yields of cDNA and IVT RNA are summarized in Table 5.

TABLE 8

Yields of Rev cDNA produced by amplification of three Clade B patient samples using the Rev T7 7912 16-overlap primer group and IVT RNA transcribed therefrom

| Samples | cDNA yield (µg) | IVT RNA yield (µg) |
|---|---|---|
| HND-034 | 48 | 1023 |
| HTM-367 | 39 | 825 |
| R04-26634 | 46 | 869 |

Figure 13:
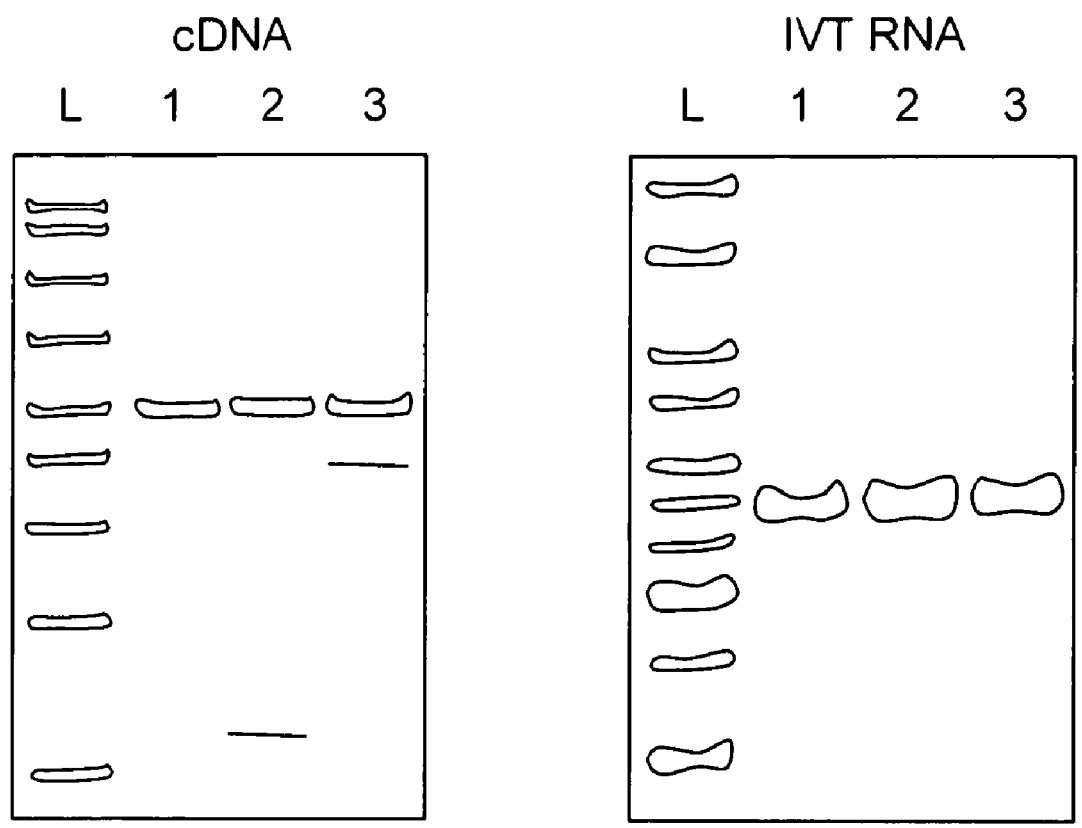
FIG. 13 show gel electrophoresis of Rev secondary amplicons prepared from three HIV Clade B subjects using the Rev T7 7912 16-overlap primer group together with the Rev 8300 64T primer group (left panel) and IVT RNA transcribed therefrom (right panel). Left panel: Non-denaturing gel electrophoresis of 50 ng of purified Rev cDNA. L: molecular weight ladder, AmpliSize DNA ruler 50-2000 bp (BioRad). Right panel: denaturing gel electrophoresis of 500 ng Rev IVT RNA. L: molecular weight ladder, 0.1-2 kb RNA ladder (Invitrogen). For both gels: Lane 1: HND-034 (Clade B), Lane 2: HTM-367 (Clade B) and Lane 3: R04-26634 (Clade B).

The quality of the Clade B Rev cDNAs and IVT RNAs prepared using the Rev T7 7912 16 overlap primer group were analyzed by agarose gel electrophoresis (FIG. 13). In all Clade B samples analyzed, Rev cDNA and IVT RNA migrate as a single band. The molecular weight of cDNA and IVT RNA fall within the expected range. Lack of smearing or other bands contaminating the IVT RNA samples indicates the high purity of the Rev amplified RNA.

Further Optimization of HIV Rev T7 Primers

Figure 14A:
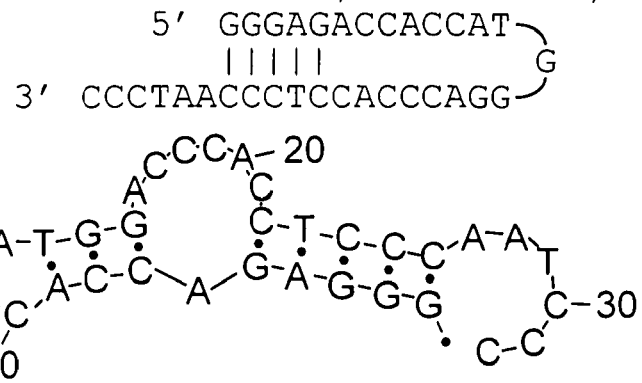
FIG. 14 shows mFold software models of the 5' end of Rev IVT RNAs produced from secondary Revc amplicons made using a Rev Hi T7 7912 primer group (corresponding to the primers of SEQ ID NO:24-29, wherein $N_1$ is G, $N_2$ is A, $N_3$ is A, $N_4$ and $N_5$ are T and $N_6$-A, C, or G) together with the Rev 8300 64T primer group. In the RNA's shown, $N_5$ corresponds to the third 5' nucleotide shown. Panel A: $N_6$=G (no substitution of the +3 G), SEQ ID NO:73 is shown; Panel B: $N_6$=C (C is substituted for the +3 G), SEQ ID NO:74 is shown; Panel C: $N_6$=A (A is substituted for the +3 G), SEQ ID NO:75 is shown.
Figure 14B:
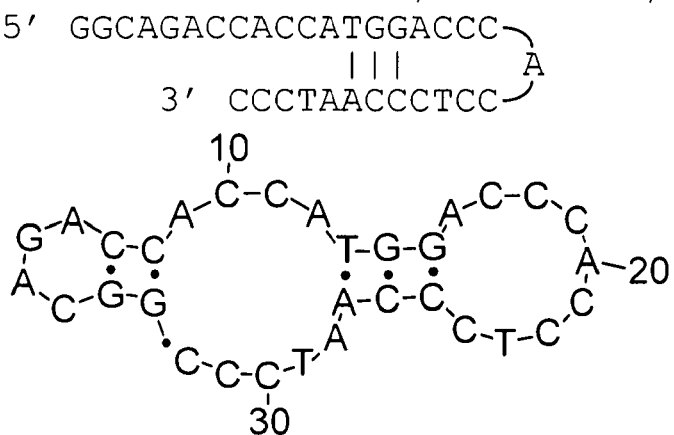
Figure 14C:
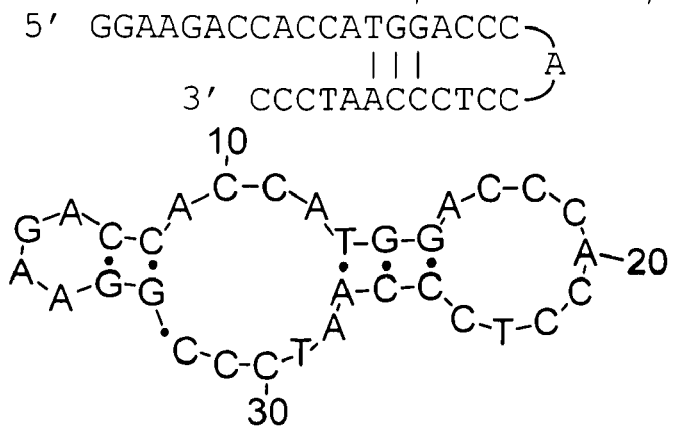

T7 promoters have a consensus sequence from −17 to +6, with +1 designated as the first transcribed nucleotide. The consensus sequence from +1 to +6 is 5' GGGAGA 3' (Tang et al. 2005 JBC 280:40704-40713). mFold software analysis of the 5' end of the Rev RNA transcribed from Rev cDNA amplified using the Rev T7 promoter primers predicted secondary structure that could interfere with translation (FIG. 14A). After study of the predicted structure, we proposed substitution of an A, C or U for the +3 G of the T7 promoter consensus sequence would result in secondary structure with a less favorable AG (see FIGS. 14B and C, where the third G is substituted with a C or A). Accordingly, Rev T7 7912 16-overlap primers were designed where the +3G position of an RNA transcribed from cDNA amplified with such primers was substituted with an A, C or U (The U in the RNA corresponds to a T in the primer). These primers correspond to SEQ ID NOs: 24-29 (see Table 2), wherein $N_6$=A, C or T. The version of these primers wherein $N_1$ is G, $N_2$ is A, $N_3$ is A, and $N_4$ and $N_5$ are T, so that the T7 promoter contained the −22 to −18 portion of the consensus sequence, was tested in the following amplification and expression experiments. These primers were termed "HiT7", because they contain more of the 5' consensus sequence of the T7 promoter than do the corresponding primers wherein each of the $N_1$ through $N_5$ are absent.

Figure 15:
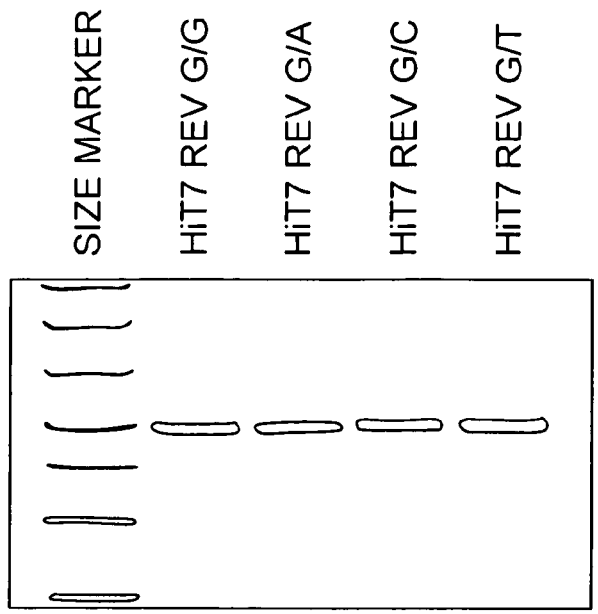
FIG. 15 shows agarose gel resolution of secondary Rev amplicons made using the PCR amplification of Rev cDNA using the indicated Rev Hi T7 7912 16-overlap primer group together with the Rev 8300 64T primer group. Hi T7 Rev G/G designates amplification with the Rev Hi T7 7912 primer group of SEQ ID NO:24-29, wherein $N_6$=G (no substitution of the +3 G) and $N_1$ is G, $N_2$ is A, $N_3$ is A and $N_4$ and $N_5$ are T (see Table 2), Hi T7 Rev G/A designates amplification with the Rev Hi T7 7912 primer group of SEQ ID NO:24-29, wherein $N_6$=A (A was substituted for the +3 G) and $N_1$ is G, $N_2$ is A, $N_3$ is A, $N_4$ and $N_5$ are T. Hi T7 Rev G/C designates amplification with the Rev Hi T7 7912 primer group of SEQ ID NO:24-29, wherein $N_6$=C (C was substituted for the +3 G) and $N_1$ is G, $N_2$ is A, $N_3$ is A, $N_4$ and $N_5$ are T. Hi T7 Rev G/T designates amplification with the Rev Hi T7 7912 primer group of SEQ ID NO:24-29, wherein $N_6$=T (T was substituted for the +3 G) and $N_1$ is G, $N_2$ is A, $N_3$ is A, and $N_4$ and $N_5$ are T.
Figure 16:
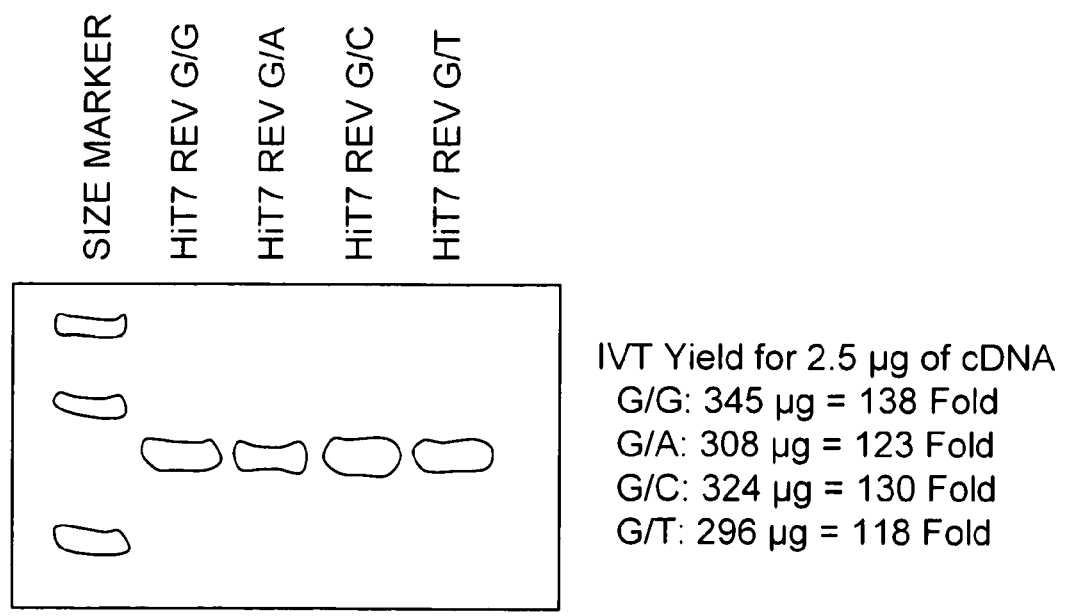
FIG. 16 shows agarose gel resolution of the Rev IVT RNA produced by in vitro transcription of the secondary amplicons indicated in FIG. 15.
Figure 17:
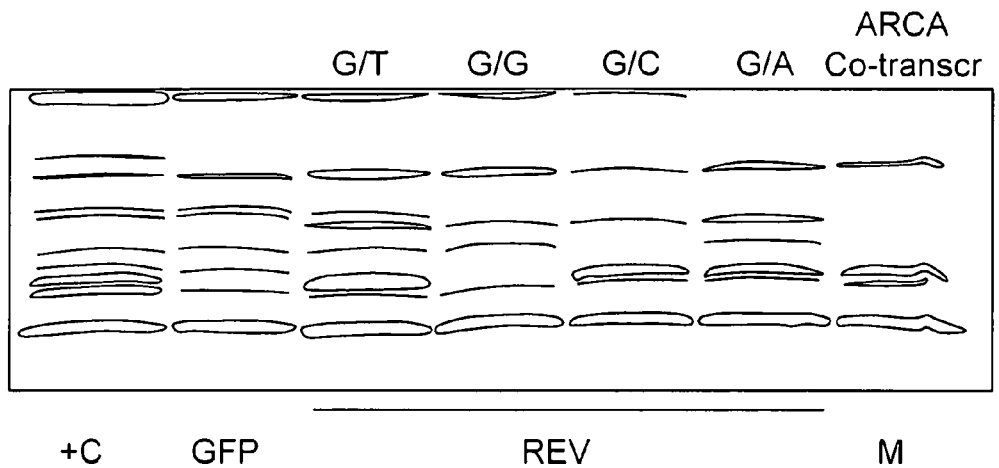
FIG. 17 shows a Western Blot analysis of the Rev proteins translated in DCs transfected with post-transcriptionally capped Rev IVT RNAs indicated in FIG. 16. Each of the RNAs was postranscriptionally capped (except for the RNA in the lane marked "ARCA co-transcr", which was co-transcriptionally capped using the ARCA m7G analog) and used to transfect DCs. The "+C" lane indicates a Rev positive control.

Secondary PCR amplification of Rev cDNA using the Rev HiT7 7912 16-overlap primers wherein $N_6$=G, A, C or T showed no difference in the cDNA yield or purity using primers that would alter the +3 position of subsequently transcribed RNA (FIG. 15). IVT RNA transcribed from cDNA amplified by the secondary PCR reactions showed good yields for all primers, indicating that a change at this position does not affect the binding of RNA polymerase or the initiation of transcription (FIG. 16). Each of the RNAs was post-transcriptionally capped and used to transfect DCs. Western Blot analysis shows that Rev protein expression was improved when the +3 G is substituted with T (U in the RNA), C or A (FIG. 17).

Example 2

Universal Primers for Amplification of HIV Clade B and Non-Clade B Gag Polynucleotides Commonly owned PCT publication WO2006/031870 discloses a scheme for amplification of HIV Gag cDNA utilizing a combination of three primary forward groups of primers and two primary reverse groups of primers. The combination of each three forward primer groups with each of the two reverse primer groups results in six primary Polymerase Chain Reaction (PCR) amplification reactions (FIG. 2).

Analysis of the Gag R1881 reverse primer group revealed that the two nucleotides at both the 5' and 3' ends of each primer are GC (see Table 3, above), which allows primers to form relatively stable homodimer structures. Accordingly, two new Gag reverse primer groups, designated the Gag R1883 primer group and the Gag R1884 primer group, were designed to circumvent such a problem (see Table 4). The new primers moved the primer annealing site downstream two or three nucleotides so that the GC sequence at 3' end is excluded from the primer sequence (FIG. 3).

Also, in order to efficiently amplify more HIV genomes, including Clade C, an additional primer (GAG R 1884.3) was designed for Gag R 1884 reverse primer group. This primer 1884.3 has degenerate mutations that would be compensatory to Clade C sequences (FIG. 3). The 1884 primer group was tested using secondary structure analysis from Oligo Etc. The homodimer formation was also analyzed using IDT Oligo Analyzer software and results are summarized in Table 9.

Analysis of the Gag R1883 and Gag R1884 primer groups using Oligo Tech software predicted no stable homodimers for three out of four primers designed. Primer 1884.2 is predicted to form a homodimer at temperature below or equal to 6.2° C. The homodimer formation therefore is not possible when primers are kept post-thaw at room temperature. The data summarized in Table 9 indicates that elimination of one terminal GC sequence from the end of the primer sequence would reduce the AG and prevent the formation of stable homodimers.

TABLE 9

Tm and Homodimer Stability of Gag R1883 and Gag R1884 Primer Groups

| Primer Groups | | Primer Tm (° C.) | Homodimer ΔG (IDT) (kcal/mole) | Homodimer Tm (OligoTech) (° C.) |
|---|---|---|---|---|
| Gag R1883 | Gag R 1883 | 64.2 | −4.13 | Not stable |
| | Gag R 1883.1 | 62.1 | −3.14 | 2.1 |
| | Gag R 1883.2 | 66.2 | −4.89 | 6.2 |
| Gag R1884 | Gag R 1884 | 64.2 | −3.14 | Not stable |
| | Gag R 1884.1 | 62.1 | −3.14 | Not stable |
| | Gag R 1884.2 | 66.2 | −4.89 | 6.2 |
| | Gag R 1884.3 | 68.3 | −3.17 | Not stable |

Figure 18:
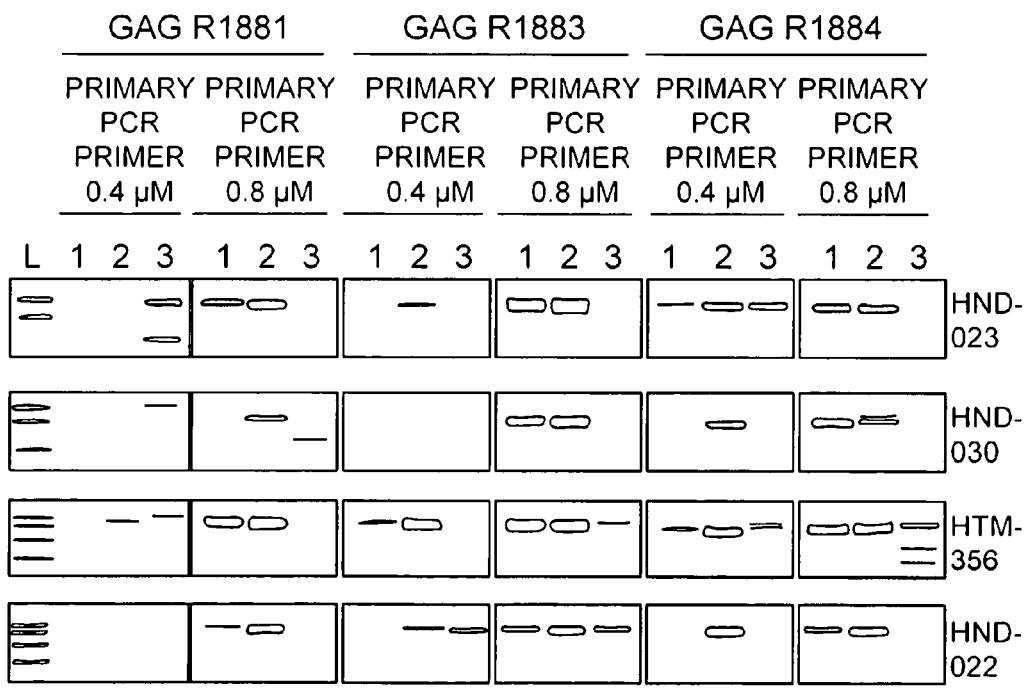
FIG. 18 shows 3% non-denaturing agarose gel resolution of secondary PCR products for Gag cDNA amplified from a primary amplicon made using the Gag R1881, Gag R1883 or Gag R1884 reverse primer groups together with the Gag forward primer groups Gag F124, Gag F304 or Gag 334. 1 μL of secondary screen PCR was loaded on. Data on four samples, FIND-023, HND-030, HTM-356, and HND-022 is shown. Primary PCR reverse primer groups used and the primary PCR primer concentration are indicated on the top. Each lane within the panel was amplified using the following combination of primary primers: Lane 1: F124/R1881 (or 1883 or 1884); Lane 2: F304/R1881 (or 1883 or 1884); Lane 3: F334/R1881 (or 1883 or 1884). Secondary PCR amplification used the Gag T7 F334 primer group (T7 Gag F334 (SEQ ID NO:59) and T7 Gag F334.1 (SEQ ID NO:60)) together with the Gag R1881 64T primer group (Gag R1881 64T (SEQ ID NO:61), Gag R1881.1 64T (SEQ ID NO:62) and Gag R1881.2 64T (SEQ ID NO:63). L: molecular weight marker, AmpliSize Molecular Ruler 50-2000 bp (BioRad).

Each of the newly designed reverse primer groups Gag R1883 and Gag R1884, together Gag forward primer groups Gag F124, Gag F304 or Gag F334, were tested for amplification of Gag cDNA from four HIV Clade B subjects' plasma in three primary PCRs. For each sample, the cDNA produced in the reverse transcription reaction was divided into six primary PCR reactions. The primary PCR reactions were conducted using three different primer groups (Gag R1881, Gag R1883, and Gag R1884) at two different primer concentrations (0.4 μM and 0.8 μM). As shown in FIG. 18, amplification using 0.8 μM primary PCR primer concentration produced more positive PCR products in comparison to the 0.4 μM primer concentration. At 0.4 μM primer concentrations, the Gag R1883 primer group, and more notably Gag R1884 primer group, produced more positive lanes compared to reactions performed with Gag R1881 primer group. The Gag R1884 primer group is preferred over the Gag R1883 primer because of slightly better performance in Clade B, more noticeable improvement in C subjects, and theoretical broader coverage of quasispecies.

Figure 19:
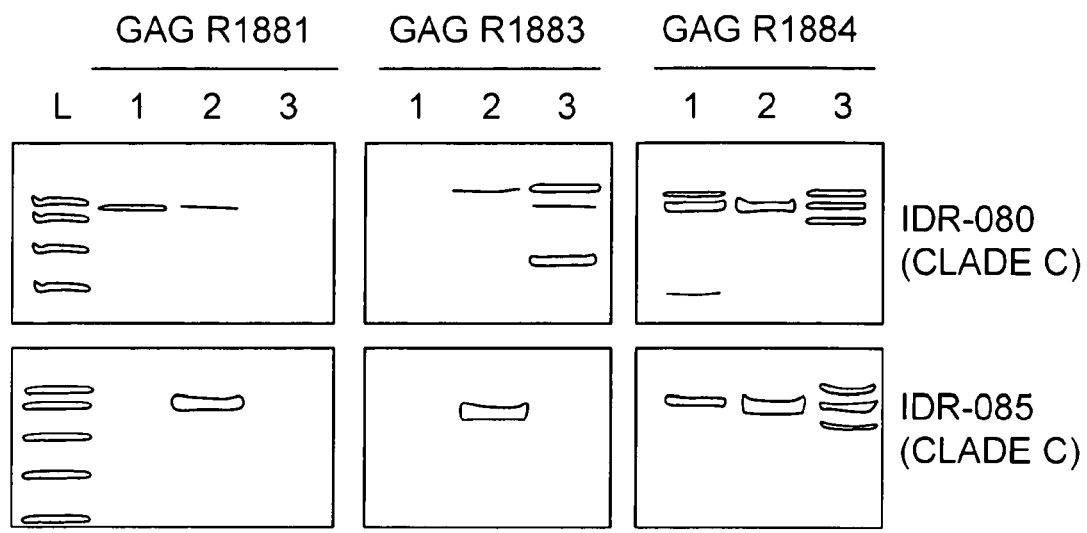
FIG. 19 shows 3% non-denaturing agarose gel resolution of secondary PCR products for Gag cDNA amplified with Gag R1881, Gag R1883, and Gag R1884 reverse primer groups. 1 μl, of secondary screen PCR was loaded on gel. Data on two Clade C samples, IDR-080 and IDR-085 is shown. Primary primer concentration is 0.8 μM. Primary PCR reverse primer groups used are indicated on the top. Each lane within the panel was amplified using the following combination of primary-primers: Lane 1: F124/R1881 (or 1883 or 1884); Lane 2: F304/R1881 (or 1883 or 1884); Lane 3: F334/R1881 (or 1883 or 1884). L: molecular weight marker, AmpliSize Molecular Ruler 50-2000 bp (BioRad).

Amplification of two Clade C patient samples (IDR-080 and IDR-085) using 0.8 μM primer concentrations of three Gag reverse primer groups (Gag R1881, R1883 and R1884) is shown in FIG. 19. Gag R1883 primer group performed slightly better than the GAG R1881 or Gag R184 primer groups, as evident by more prominent band in lane 2 of sample IDR-085. However, the reactions performed with primer group 1884 produce more positive amplified product in lanes 1 and 2 for both Clade C samples tested. This is consistent with our hypothesis that primer group Gag R1884 would enhance amplification of Clade C samples in comparison to primer group Gag R1883.

Figure 20:
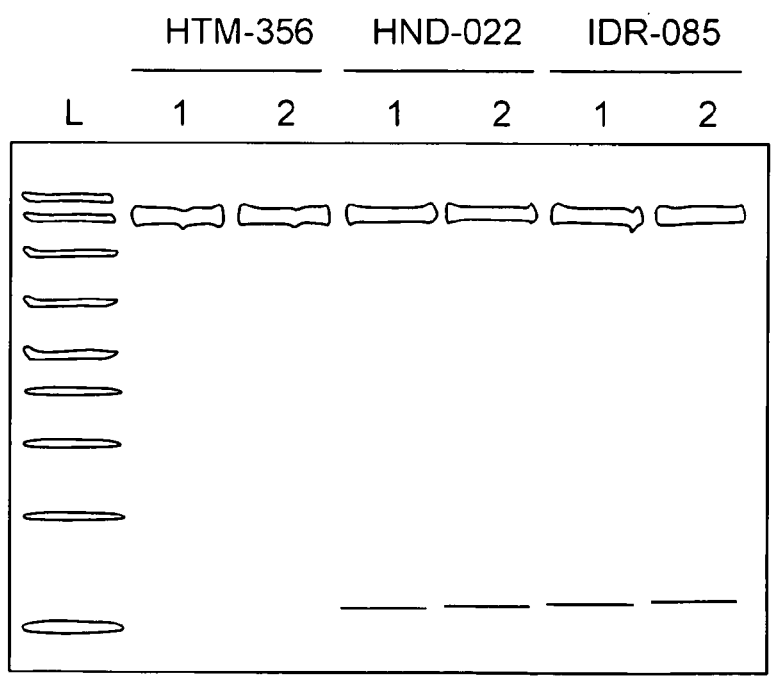
FIG. 20 shows 3% non-denaturing agarose gel resolution of 100 ng of purified secondary Gag amplicons from three subjects, HTM-356 (Clade B), HND-022 (Clade AG), and IDR-085 (Clade C). Within each subject, the primary amplification used the Gag R1881 or Gag R1913 primer group together with the Gag F124, Gag F304 or Gag F334 primer group. Primary reactions resulting in a positively amplified product(s) of expected size were amplified in secondary reaction using the Gag T7 F334 primer group together with the Gag R1881 64T primer group L: molecular weight ladder, AmpliSize Molecular Ruler 50-2000 bp (BioRad).

Primary PCR reactions were performed on the cDNA samples from three subjects (HTM-356 (Clade B), HND-022 (Clade AG), and IDR-085 (Clade C)) using 0.8 μM primer concentrations of Gag R1881 or Gag R1884. cDNA synthesis and secondary PCR amplification were performed as described above. Preparative cDNA yield and quality after were examined after reverse transcription and primary amplification using the Gag R1881 or Gag R1884 primer groups followed by secondary amplification. Yields were calculated by multiplying the concentration by the QIAquick column eluate. The yields of the secondary PCR fragments obtained in each condition are summarized in Table 10. The yields of Gag cDNA amplified using Gag R1884 primers was comparable with yields obtained with the Gag R1881 primers. The quality of the cDNA was assessed by non-denaturing gel electrophoresis 100 ng of Gag cDNA produced by the secondary PCR (FIG. 20). Molecular weight of Gag cDNAs were determined by alphaimager autoquery function and recorded in Table 10. No difference was observed in the quality of the cDNA obtained from all three samples using either the Gag R1881 or R1884 reverse primer groups.

TABLE 10

Yields of Gag cDNA Obtained Using Gag R1881 or Gag R1884 in Clade B, Clade AG or Clade C Subjects

| Samples | Initial Concentration (μg/μL) | Yield (μg) | MW |
|---|---|---|---|
| HTM-356 Gag amplified using Gag R1881 | 0.53 | 90 | 1411 |
| HTM-356 Gag amplified using Gag R1884 | 0.46 | 78 | 1411 |
| HND-022 Gag amplified using Gag R1881 | 0.33 | 56 | 1435 |
| HND-022 Gag amplified using Gag R1884 | 0.38 | 65 | 1435 |
| IDR-085 Gag amplified using Gag R1881 | 0.34 | 58 | 1411 |
| IDR-085 Gag amplified using Gag R1884 | 0.28 | 48 | 1411 |

Figures 21, 22A, 22B, 22C, 22D, 22E:
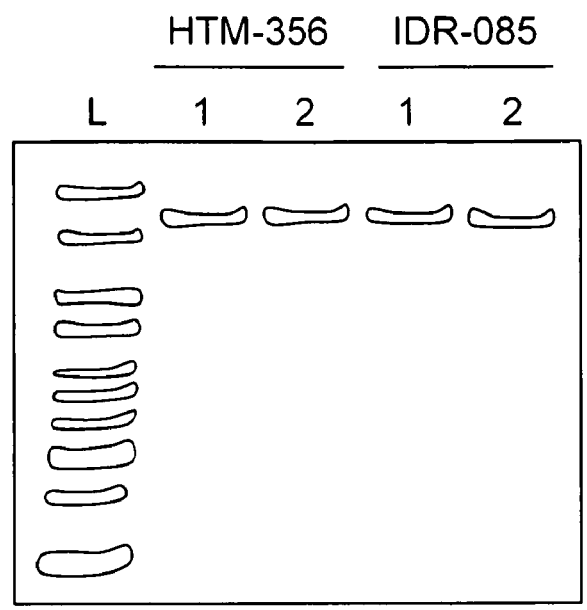
FIG. 21 shows 2% denaturing agarose gel resolution of 500 ng of purified Gag IVT RNA produced from in vitro transcription of secondary amplicons from subjects HTM-356 (Clade B) and IDR-085 (Clade C). Within each subject, the primary amplification used the Gag R1881 primer group together with the Gag F124, Gag F304 or Gag F334 primer groups (Lane 1); or the Gag R1884 primer group together with the Gag F124, Gag F304 or Gag F334 primer groups (Lane 2). The secondary amplification used the Gag T7 F334 primer group together with the Gag R1881 64T primer group L: molecular weight ladder, 0.1-2 kb RNA ladder (Invitrogen).

IVT RNA was produced as described above for four cDNA samples made using the Gag R1884 primer group for primary amplification. The concentrations and calculated yields are summarized in Table 11. The quality of each RNA sample was analyzed on denaturing gel electrophoresis (FIG. 21). The amplification factors (IVT RNA mass obtained/cDNA mass used in the reaction) were in the range of 27 to 37. The yield of RNA obtained from cDNA amplified using Gag R1884 primer group is comparable with that obtained using Gag R1881 primer group.

TABLE 11

Gag IVT RNA Yields

| Samples | Final Concentration (µg/µL) | Yield (µg) |
|---|---|---|
| HTM-356 Gag amplified using Gag R 1881 | 1.1 | 675 |
| HTM-356 Gag amplified using Gag R 1884 | 1.1 | 722 |
| IDR-085 Gag amplified using Gag R 1881 | 1.1 | 912 |
| IDR-085 Gag amplified using Gag R 1884 | 1.1 | 925 |

Example 3

Improved Primer and Primer Group for Amplification of HIV Clade B and Non-Clade B Nef Sequences A partial list of Nef primers and primer groups disclosed in PCT publication WO2006/031870 for the primary round of amplification of Nef cDNA is shown in Table 5, above. Applicants discovered that the addition of the novel primer Nef F8235.2 (SEQ ID NO:58) to the Nef F8235 primer group (SEQ ID Nos:49 and 50) enhanced amplification of HIV Nef sequences.

In order to test the Nef F8235.2 primer group containing the new Nef F8235.2 primer, HIV viral RNA was isolated from 2 to 3 mL archived frozen plasma of three HIV patients infected with Clade B virus (patient HTM 367), Clade C virus (patient IDR-085) and Clade AG virus (patient HND-022) using a NucliSens™ kit (BioMerieux), according to the manufacturer's instructions. The titers of these three samples were of 53,334, 53,703 and 154,882 copies/mL, respectively.

Nef cDNAs were synthesized by reverse transcription of the HIV RNA using oligo dT primers. The reverse transcription reaction contained 2.5 µL of each eluted viral RNA, 20 oligo dT$_{(20)}$ (Invitrogen), 2 units of RNAseout™ (Invitrogen), 0.5 mM of each dNTP (Clontech), and Superscript™ first strand buffer. After annealing at 65° C. for 5 minutes, 5 mM DTT and 10 units of Superscript III™ (Invitrogen) were added and the reaction was incubated at 55° C. for 1 hour.

2.5 µL of the reverse transcription reaction was used as a template in a primary PCR containing 5 units of PFU Ultra HS, PFU buffer (Stratagene), 0.2 mM of each dNTP (Stratagene), and the corresponding group primer groups at a final concentration of 0.4 µM in a final reaction volume of 50 µL. In two separate primary amplifications, the new Nef F8235 primer group (containing previously disclosed Nef F8235 and Nef F8235.1 primers and new Nef F8235.2 primer) or the Nef F8343 primer group were combined with the Nef R9089 reverse primer group (see Table 5). The reactions were heated at 95° C. for 2 minutes and then run for 40 cycles as follows: 95° C. for 30 seconds, 54° C. for 30 seconds, and 72° C. for 3 minutes. After the last cycle, an extension was performed at 72° C. for 10 minutes and the reaction was stopped by chilling to 4° C. The 54° C. annealing temperature in the primary and secondary PCR amplifications allowed for annealing of primers to templates with a limited degree of mismatch.

1 µL of each of the primary PCRs was then used as a template in a secondary PCR reaction containing 2.5 units of PFU Ultra HS, PFU buffer (Stratagene), 0.2 mM of each dNTP (Stratagene), and 5 µM Nef-specific T7 and 64T primer groups shown in Table 12, in a final reaction volume of 25 µL. This secondary PCR modified the cDNA products of the primary PCR reaction by inserting a T7 RNA polymerase binding site at the 5' end and a poly(T)$_{64}$ tail, which is transcribed into a poly(A)$_{64}$ tail on the synthesized RNAs. The cycling parameters were the same as in the primary PCR reaction. Products of the secondary PCR reaction were purified using a QIAQUICK purification column (QIAGEN) prior to in vitro transcription. The expected size of the amplified Nef secondary PCR product calculated from the position of primers used in the secondary round of PCR and adding sequence for T7 promoter and 64T stretch is 836 bp. PCR resulted in a productive amplification of DNA fragments with expected size from all of three patient samples (FIG. 22A-C).

TABLE 12

Nef T7 and 64T Primers and Primer Groups disclosed in WO2006/031870

| Primer Group (PG)/Primer Name | Sequence 5' to 3' | ID NO: |
|---|---|---|
| PG: Nef T7 8343 | | |
| Nef T7 8343 | TAATACGACTCACTATAGGGAGACCAC CATGGGTGGCAAGTGGTCAAAAAG | 64 |
| Nef T7 8343.1 | TAATACGACTCACTATAGGGAGACCAC CATGGGTGGCAAGTGGTCAAAACG | 65 |
| PG: Nef 9069 64T | | |
| Nef 9069 64T | (T)$_{64}$CCAGTACAGGCAAAAAGC | 66 |
| Nef 9069.1 64T | (T)$_{64}$CAGTACAGGCGAAAAGC | 67 |
| Nef 9069.2 64T | (T)$_{64}$CCAGTACAGGCAAGAAGC | 68 |

The products from the primary PCR that also resulted in a successful amplification during secondary PCR were mixed and used to populate the secondary PCR on a preparative scale. The reactions were performed as described above, but in several identical tubes in order to generate sufficient mass of cDNA to be used as a template in an in vitro transcription reaction. Agarose gel analysis of preparative scale purified secondary PCR products is shown in FIG. 22D. Sequence analysis of these fragments confirmed that the amplified cDNA correspond to Nef (data not shown). Products from the nested PCR reactions were transcribed in vitro to generate Nef IVT RNA, which was analyzed by agarose gel electrophoresis (FIG. 22E).

Because of the diversity of the HIV and the presence of deletion and insertions within the open reading frames of interest, the molecular weight for cDNA and in vitro-transcribed RNA is expected to vary. We performed a detailed analysis of the molecular weight of Nef cDNA and in vitro-transcribed RNA amplified from 10 distinct infectious plasma samples. The size of cDNA band was measured by migration on the agarose gel relative to the molecular weight markers. The observed size distribution of the Nef cDNA analyzed by non-denaturing agarose gel electrophoresis was 841±50 bp. The observed size distribution for amplified Nef IVT RNA analyzed by denaturing agarose gel electrophoresis was 801±52 nucleotides. The range of molecular weights for each antigen observed with these 10 samples is indicative of the high degree of subject-to-subject virus diversity.

A summary of successful amplification of Nef, Gag, Rev and Vpr from plasma samples of 30 patients is shown FIG. 23. Viral load varied greatly from sample to sample. Whenever possible, a larger volume of viral plasma was used (up to 3 mL) for HIV RNA extraction to achieve higher yield of viral RNA. The sample with the lowest copy number resulting in successful amplification was sample 10 where the concentration of HIV RNA in the final eluate was 444 copy/4 vRNA (viral genome RNA). The calculation of final recovered HIV RNA concentration assumes no loss of RNA occurs during the extraction procedure. With losses, the absolute copy requirement would be even lower. Overall these data demonstrates consistently successful amplification of Nef nucleic acids from plasma samples with diverse viral load.

An advantage of our method for antigen generation is its ability to capture HIV mutations that evolve under dynamic host CTL pressure. The multiplex RT-PCR strategy for capture of HIV antigens was designed to be broadly applicable to the general HIV-infected population irrespective of Clade designation, but also anticipates that it would capture various quasispecies present in a given subject. This is the cornerstone of our novel therapeutic paradigm that enables targeting, not only of dominant viruses, but also newly emerging virus populations that evolve as a result of immune pressure.

Figure 24A:
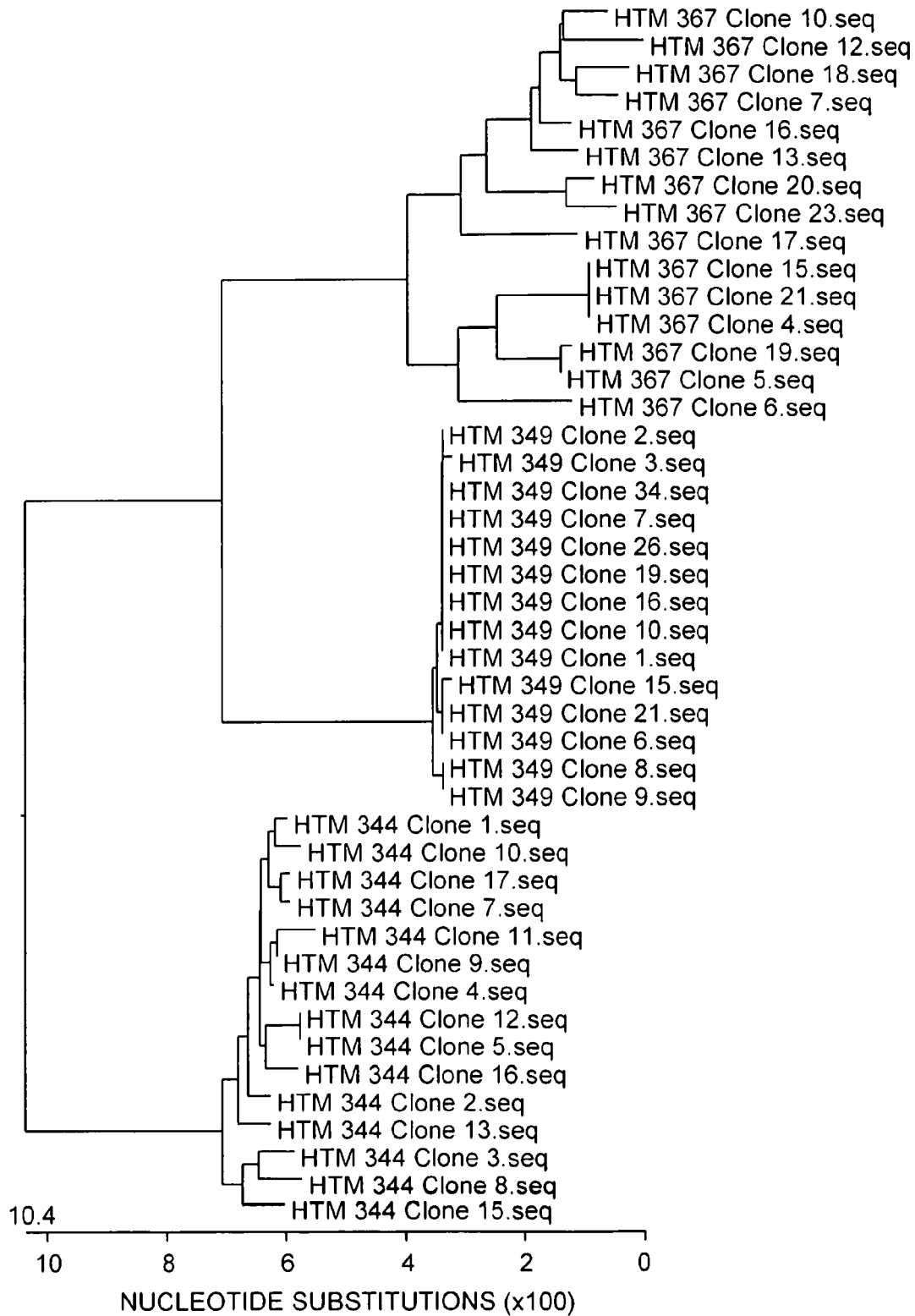
FIG. 24 shows the amplification of HIV Nef quasispesies using the RT-PCR approach disclosed herein. Panel A: Phylogenetic relationships of cDNA sequences of isolated full-length Nef clones obtained from the plasma of three subjects with HIV infection. Products of a secondary PCR reaction for Nef were cloned, screened for the presence of an insert and sequenced. Sequences of the clones were aligned using Clustal V software and a phylogenetic tree was built using the MegAlign module of the Lasergene software. Panel B: Phylogenetic relationships of Nef proteins obtained from nucleotide sequences. Horizontal scale indicates the number of nucleotide mutations or amino acid substitutions on each clone relative to neighbor clones.
Figure 24B:
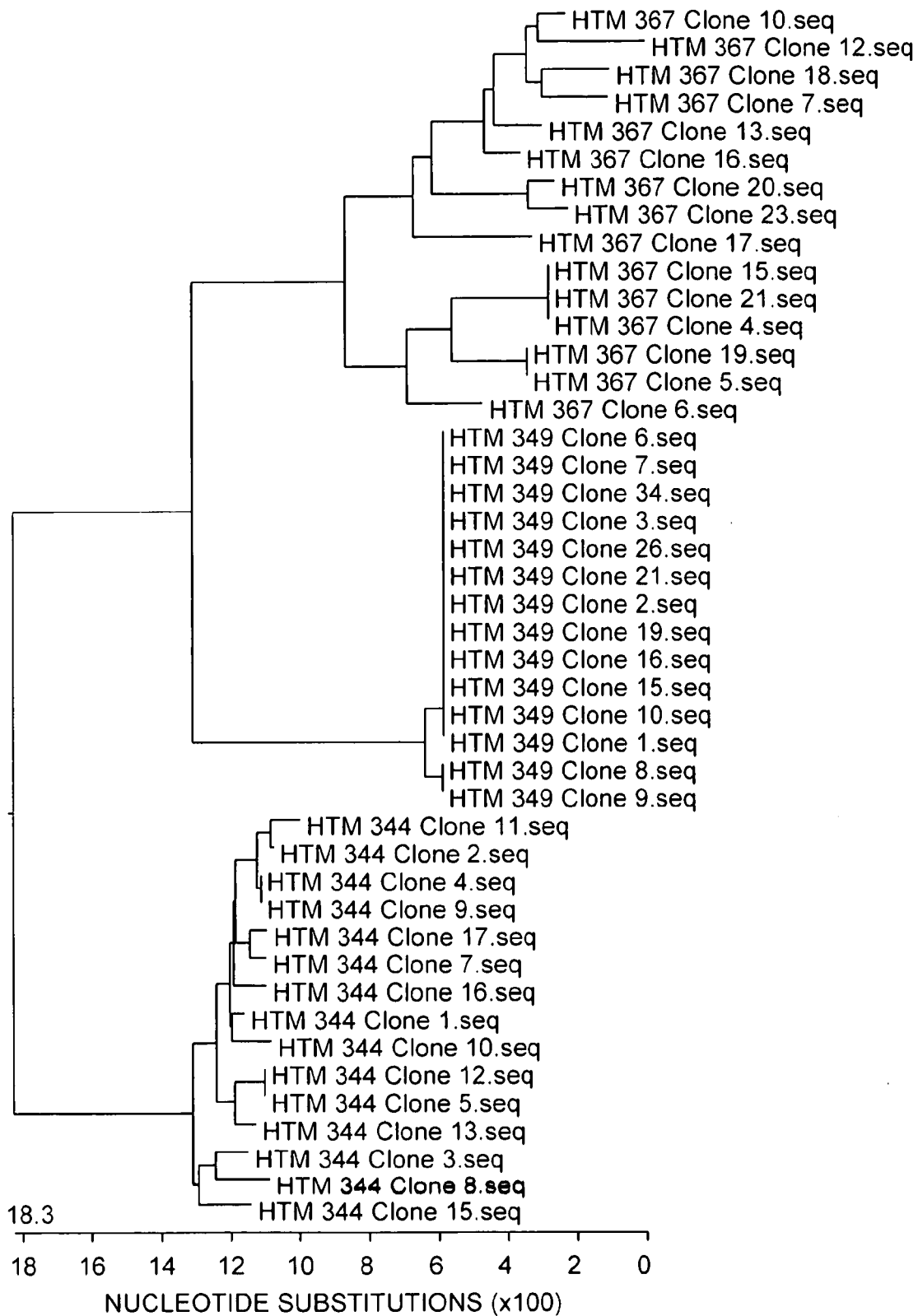

To test our hypothesis that multiple quasispecies are co-amplified from a given subject, PCR fragments encoding full length Nef cDNA amplified from samples HTM-349, HTM-367 and HTM-344 were cloned, sequenced and analyzed using phylogenetic tree analysis. Nucleotide sequence analysis and identity verification was performed using Lasergene software (DNAStar), the Los Alamos HIV Sequence Database (http://www.hiv.lanl.gov), and BLAST analysis. Nucleotide sequences of Nef cDNA clones were aligned using Clustal V module of Lasergene (DNAstar). Phylogenetic trees were constructed using the MegAlign module of the Lasergene software (DNAstar). A total of 15 clones were analyzed for each subject. The results are shown in FIG. 24. The analysis demonstrated that the cDNA population did indeed capture genes encoded by various HIV quasispecies. Phylogenetic tree analysis demonstrated that each subjects' Nef sequences grouped within other sequences from that subject and were distinct from another subjects' sequences. More interestingly however is the observation that the number of the Nef variable sequences was different in each subject. On the nucleotide level (FIG. 24, panel A) the subject HTM 344 displayed greater diversity where out of 15 clones analyzed 14 clones were unique, followed by subject HTM 367 with 13 unique clones and for subject HTM 349 only 6 unique clones. Not every nucleotide mutation leads to amino acid substitution, so the diversity is lower on the level of amino acid sequence (FIG. 24 Panel B) with the same order of diversity trend for the three subjects. These data indicate that, as predicted, the multiplex RT-PCR is capable of capturing various quasispecies within each individual subject.

We next performed further analysis of the Nef sequences and scored individual primers on the level of the secondary PCR reactions that were productive in the reaction. The Nef cDNA sequences were analyzed in the regions corresponding to the regions defined by the primers and identity of the primers was identifies by sequence. A total of 15 Nef clones were analyzed for each subject. Utilization of both forward and reverse primers was performed and the analysis is summarized in Table 13. The numbers in Table 13 represent how many clones contained the identified primer.

TABLE 13

Selective utilization of primers by RT-PCR from various HIV subjects

| Primer name | Primer sequence 5'-3' | SEQ ID NO: | Utilization in RT-PCR in Various subjects | | |
|---|---|---|---|---|---|
| | | | HTM 344 | HTM 349 | HTM 367 |
| Nef T7 8343 | TAATACGACTCACTATAGGGAGACCACCATGGGTGG CAAGTGGTCAAAAAG | 64 | 1 | 0 | 10 |
| Nef T7 8343.1 | TAATACGACTCACTATAGGGAGACCACCATGGGTGG CAAGTGGTCAAAACG | 65 | 12 | 0 | 0 |
| New | TAATACGACTCACTATAGGGAGACCACCATGGGTGG CAAGTGGTCAAAAGG | 76 | 2 | | 5 |
| | TAATACGACTCACTATAGGGAGACCACCATGGGTGG CAAGTGGTCAAAAAT | 77 | | 15 | |
| Nef 9069 64T | (T)$_{64}$CCAGTACAGGCAAAAAGC | 66 | 7 | 8 | 11 |
| Nef 9069.1 64T | (T)$_{64}$CAGTACAGGCGAAAAGC | 67 | 6 | 2 | 4 |
| Nef 9069.1 64T | (T)$_{64}$CCAGTACAGGCAAGAAGC | 68 | 2 | 5 | 0 |

The forward primer utilization of sample HTM 344 demonstrated that 12 out of 15 clones analyzed were formed by primer F8343.1, however in sample HTM 367 a different primer, F8343 formed majority of clones. Most interestingly, a novel sequence was identified within one of the primer annealing regions. The sequence was termed "new" and was different from either F8343 or F8343.1 primer sequence by 2 nucleotides in a most 3' end position of the primer. We believe that this sequence is formed due to a proof reading activity of the enzyme used in a PCR reaction: that is, if a mismatch between primer and template is located at the most 3' end of the primer the mismatch is repaired by the 3' exonuclease proofreading activity of the Pfu enzyme. Similar analyses were performed for the utilization of the reverse primers. Primer R 9069 was preferentially used in all three samples, primer Nef R9060.1 was the second most productive primer for sample HTM 344 and primer Nef R9060.2 was the second most productive primer for sample HTM 349. No new reverse primers were identified in all three groups analyzed. The 3' end of the PCR fragment is defined by the cDNA synthesis step during the RT reaction. The lack of "repaired" primers is most likely due to lack of proofreading activity in the RT enzyme. These data support the proposed design and demonstrates that in multiplex PCR the productive annealing of various primers to template is defined by the actual sequence of the HIV genome in the primer annealing sequence. Since the sequence within this region varies from patient to patient, the preferred utilization of the primers in the PCR reactions differ as well.

While the expression of each individual RNA encoding each of the four antigens was studied in the DC as described below, we were not able to devise a universal method of detection or identify an antibody that could cross-react with all subject-specific amplified material (data not shown). Detection of HIV proteins using the most common established techniques like Western blot or intracellular staining is complicated by the lack of widely available commercial reagents which cross-react with proteins amplified from various subjects. Also, the sensitivity of these methods of detection is not sufficient to detect protein expression when a relatively low amount of RNA (1 µg or less) is delivered to the DC. Instead, we elected to study presentation of antigens by RNA-electroporated DC with detection of induced T-cell responses as a surrogate assay for protein expression using PBMCs derived from a successfully HAART-treated HIV-infected donor.

Figure 25A:
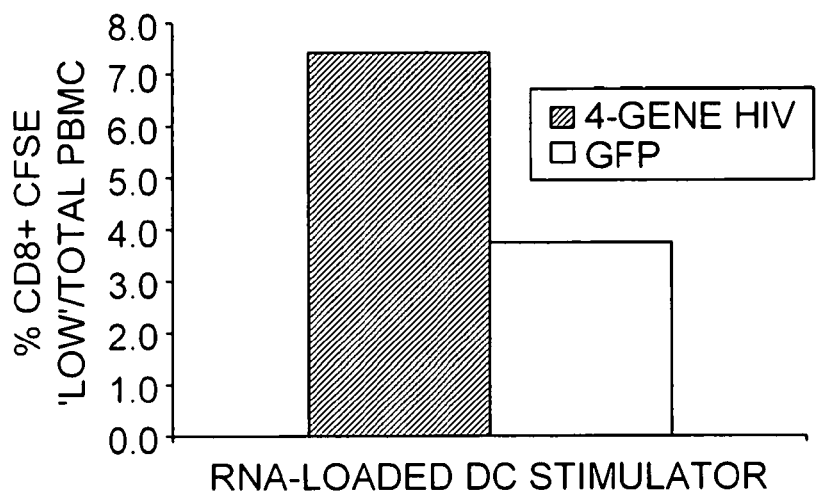
FIG. 25 shows flow cytometry analysis of T cell subsets stimulated by DCs electroporated with IVT RNA encoding HIV antigens Gag, Rev, Nef and Vpr. Panel A: CFSE-low cells expressed as a percentage of total PBMCs. DCs electroporated with 4 HIV antigen-encoding RNAs or eGFP were cultured with CFSE-labeled PBMCs for 6 days. Frequency of CD8+ CFSE-low cells determined by flow cytometry. Panel B: CD28/CD45RA phenotype of CD8+ cells induced to proliferate (CFSE-low) by DC electroporated with 4 HIV antigen-encoding RNAs, as compared to the frequency of CD8+ CFSE-low cells induced by eGFP-RNA loaded control DC; as determined by flow cytometry. Phenotype of CD8+ CFSE 'low' cells induced with HIV-DC (left) and phenotype of CD8+ CFSE 'low' cells induced with eGFP-DC (right). Panel C: Frequency of IFN-γ positive cells within the CD8+ CFSE-low subset induced by 4 hr re-stimulation with DC expressing individual HIV antigen-encoding RNAs, or eGFP control RNA, as determined by intracellular staining and flow cytometry.
Figure 25B:
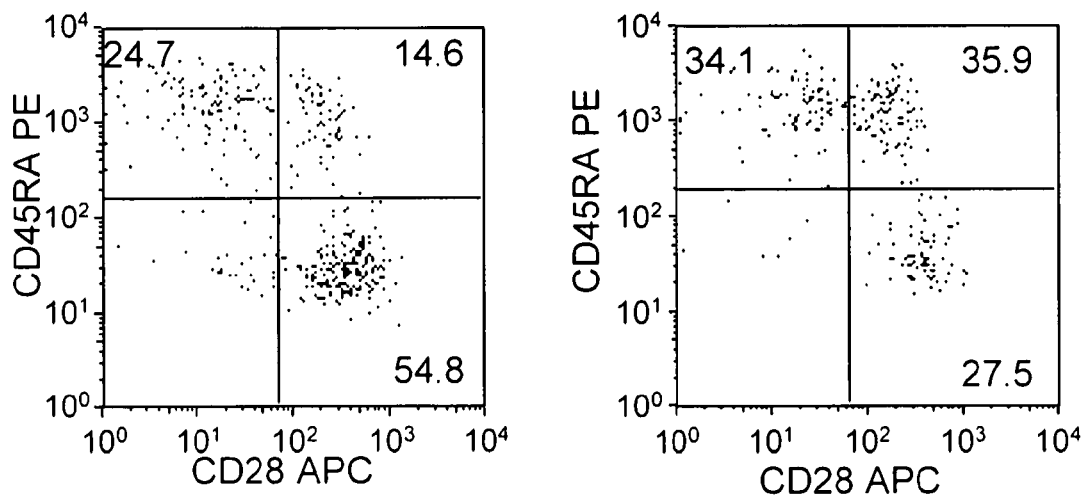
Figure 25C:
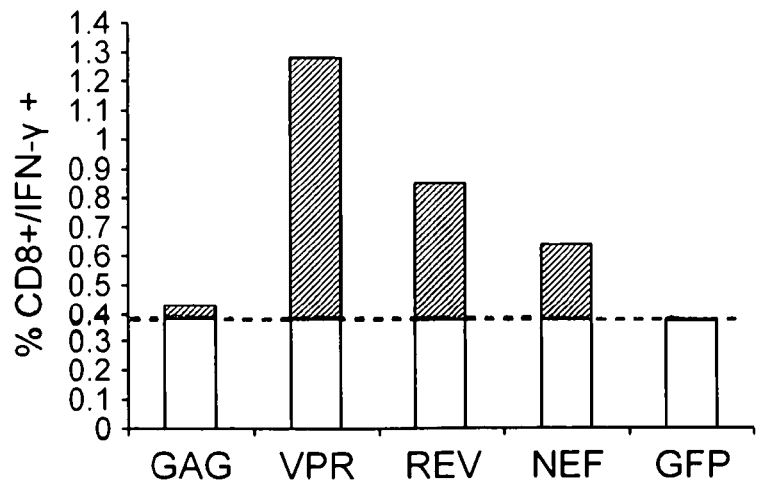

To determine whether HIV RNAs generated by the described method could encode antigens that are expressed, processed, and presented by DC and induce CD8+ T-cell immunity, a single DC preparation was electroporated with four HIV genes (Gag, Rev, Vpr and Nef) encoded as RNAs, and the cells co-cultured with autologous PBMCS pre-labeled with CFSE. After 6 days of co-culture, the frequency and phenotype of proliferating cells was determined by detecting residual CFSE fluorescence within the CD8+ T cell population with 'effector' versus 'effector/memory' functional subsets defined by expression of CD45RA and CD28. After the 6 day co-culture CD8 T-cell population with an eGFP RNA transfected DC control population the frequency of CFSE 'low' was 3.75%, however in experimental arm where CD8 T-cell population when driven by HIV-RNA electroporated DC the frequency of CFSE 'low' cells was 7.41% (FIG. 25A). No specific activity above background was recorded within the CD4+ subset, with all DC populations inducing 1% CD4+ CFSE-low cells within total PBMCs. Within the proliferating CFSE low CD8+ T cell subset, driven by the HIV RNA-loaded DC, 44% of cells had a fully differentiated effector phenotype (CD45RA+/CD28−) versus 32.3% of cells having an effector/memory phenotype (CD45RA−/CD28+) (FIG. 25B). Subsequent re-stimulation for 4 hours with DC populations bearing one of the four HIV genes, or RNA encoding eGFP (negative control), CFSE low CD8+ T cells were tested for IFN-γ expression by intracellular staining. Immunity to all four antigens was detected above the negative control background, as defined by the frequency of CD8+ CFSE-low cells expressing IFN-γ induced by DC loaded with individual HIV antigen RNAs, as compared to IFN-γ induced by re-stimulation in the presence of DC bearing eGFP negative control RNA (FIG. 25C). Co-cultures that were originally established on negative control eGFP-electroporated DC for 6 days, and then underwent re-stimulation with individual HIV antigen-encoding RNA-electroporated DC for detection of induced IFN-γ, all expressed less than 0.15% IFN-γ activity within the CD8+ CFSE-low subset.

In summary, flow cytometric follow up of T cell-DC co-cultures revealed that DCs electroporated with a the four HIV antigen-encoding RNAs successfully induced proliferation and effector function (IFN-γ activity) to all four antigens within the responder CD8+ T cell subset, providing conclusive evidence that HIV antigens encoded by RNA can be translated and presented by DC to invoke a poly-antigen response. Such activity is presumed to be an essential aspect of an immunotherapeutic designed to control HIV viral escape. In addition, cell surface phenotyping showed that a subset of the responder population had a CD28+/CD45RA− 'effector/memory' phenotype which has been linked to long-term non-progression (5) (6). No specific activity was recorded within the CD4+ subset, consistent with the inability of antigen encoded by RNA to efficiently target the endosomal (MHC class II) pathway (28).

We claim:

1. A composition comprising at least one or a combination of Rev T7 promoter primers selected from the group consisting of:

(SEQ ID NO: 24)
$N_1N_2N_3N_4N_5$TAATACGACTCACTATAGG$N_6$AGACCACCATGGACCCACCTCCCAACC, (SEQ ID NO: 25)
$N_1N_2N_3N_4N_5$TAATACGACTCACTATAGG$N_6$AGACCACCATGGACCCACCTCCCAGCC, (SEQ ID NO: 26)
$N_1N_2N_3N_4N_5$TAATACGACTCACTATAGG$N_6$AGACCACCATGGACCCACCTCCCAGTT, (SEQ ID NO: 27)
$N_1N_2N_3N_4N_5$TAATACGACTCACTATAGG$N_6$AGACCACCATGGACCCTTACCCCAACC, (SEQ ID NO: 28)
$N_1N_2N_3N_4N_5$TAATACGACTCACTATAGG$N_6$AGACCACCATGGACCCTTACCCCAAAC,

-continued (SEQ ID NO: 29)
N₁N₂N₃N₄N₅TAATACGACTCACTATAGGN₆AGACCACCATGGACCCTTACCCCAAGC, (SEQ ID NO: 17)
N₁N₂N₃N₄N₅TAATACGACTCACTATAGGN₆AGACCACCATGTCAGACCCACCT, (SEQ ID NO: 18)
N₁N₂N₃N₄N₅TAATACGACTCACTATAGGN₆AGACCACCATGTCAGACCCGCCT, (SEQ ID NO: 19)
N₁N₂N₃N₄N₅TAATACGACTCACTATAGGN₆AGACCACCATGTCAGACCCTCCT, (SEQ ID NO: 20)
N₁N₂N₃N₄N₅TAATACGACTCACTATAGGN₆AGACCACCATGTCAGACCCATAC, (SEQ ID NO: 21)
N₁N₂N₃N₄N₅TAATACGACTCACTATAGGN₆AGACCACCATGTCAGATCCATAC, (SEQ ID NO: 22)
N₁N₂N₃N₄N₅TAATACGACTCACTATAGGN₆AGACCACCATGTCAGACCCTTAC, and (SEQ ID NO: 23)
N₁N₂N₃N₄N₅TAATACGACTCACTATAGGN₆AGACCACCATGTCAGACCCCTAC;

wherein N₆ is G, A, C or T; and either N₁ is G, N₂ is A, N₃ is A and N₄ and N₅ are T or each of N₁ through N₅ are absent.

2. The composition of claim 1, wherein N₁ is G, N₂ is A, N₃ is A and N₄ and N₅ are T.

3. The composition of claim 1, wherein each of N₁ through N₅ are absent.

4. The composition of claim 1, wherein N₆ is A, C or T.

5. The composition of claim 1, wherein N₆ is G.

6. The composition of claim 1, which comprises at least two primers selected from the group consisting of SEQ ID NO:24; SEQ ID NO:25, SEQ ID NO:26, SEQ ID NO:27, SEQ ID NO:28 and SEQ ID NO:29.

7. The composition of claim 6, which comprises SEQ ID NO:24; SEQ ID NO:25, SEQ ID NO:26, SEQ ID NO:27, SEQ ID NO:28 and SEQ ID NO:29.

8. The composition of claim 6, further comprising a Rev 64T reverse primer selected from the group consisting of SEQ ID NO:14, SEQ ID NO:15 and SEQ ID NO:16, or any combination thereof.

9. The composition of claim 1, which comprises at least two primers selected from the group consisting of SEQ ID NO:17, SEQ ID NO:18, SEQ ID NO:19, SEQ ID NO:20, SEQ ID NO:21, SEQ ID NO:22 and SEQ ID NO:23.

10. The composition of claim 9, which comprises SEQ ID NO:17, SEQ ID NO:18, SEQ ID NO:19, SEQ ID NO:20, SEQ ID NO:21, SEQ ID NO:22 and SEQ ID NO:23.

11. The composition of claim 9, further comprising a Rev 64T reverse primer selected from the group consisting of SEQ ID NO:14, SEQ ID NO:15 and SEQ ID NO:16, or any combination thereof.

12. A method for amplifying an HIV Rev nucleic acid, comprising carrying out a polymerase chain reaction using at least one or a combination of Rev T7 7912 forward primers selected from the group consisting of SEQ ID NO:17, SEQ ID NO:18, SEQ ID NO:19, SEQ ID NO:20, SEQ ID NO:21, SEQ CD NO:22, SEQ ID NO:23, SEQ ID NO:24, SEQ ID NO:25, SEQ ID NO:26, SEQ ID NO:27, SEQ ID NO:28 and SEQ ID NO:29; and at least one or a combination of Rev R8300 64T reverse primers selected from the group consisting of SEQ ID NO:14, SEQ ID NO:15 and SEQ ID NO: 16.

* * * * *